US00RE45128E

(19) United States
(12) Reissued Patent
Robin et al.

(10) Patent Number: US RE45,128 E
(45) Date of Reissued Patent: Sep. 9, 2014

(54) CEPHALOTAXANE DERIVATIVES AND THEIR PROCESSES OF PREPARATION AND PURIFICATION

(71) Applicant: IVAX International GmbH, Rapperswil (CH)

(72) Inventors: Jean-Pierre Robin, Geneva (CH); Julie Blanchard, Puyricard (FR); Jean-Pierre Marie, Sevres (FR); Nina Radosevic, Geneva (CH)

(73) Assignee: IVAX International GmbH, Rapperswil (CH)

(21) Appl. No.: 13/661,677

(22) Filed: Oct. 26, 2012

Related U.S. Patent Documents

Reissue of:
(64) Patent No.: 7,842,687
Issued: Nov. 30, 2010
Appl. No.: 11/440,648
Filed: May 25, 2006

U.S. Applications:
(63) Continuation of application No. 10/877,067, filed on Jun. 25, 2004, now Pat. No. 7,169,774, which is a continuation-in-part of application No. 09/270,006, filed on Mar. 16, 1999, now Pat. No. 6,831,180.

(30) Foreign Application Priority Data

Mar. 20, 1998 (FR) ..... 98 03492

(51) Int. Cl.
*A61K 31/56* (2006.01)
*C07D 491/12* (2006.01)

(52) U.S. Cl.
USPC ..... 514/214.01; 540/543

(58) Field of Classification Search
USPC ..... 514/214.01; 540/543, 581
See application file for complete search history.

(56) References Cited

U.S. PATENT DOCUMENTS

| | | | |
|---|---|---|---|
| 2,889,339 | A | 6/1959 | Levy et al. |
| 2,889,340 | A | 6/1959 | Levy et al. |
| 3,246,038 | A | 4/1966 | Eiter et al. |
| 3,725,437 | A | 4/1973 | Nagoya et al. |
| 3,793,454 | A | 2/1974 | Powell et al. |
| 3,855,245 | A | 12/1974 | Koyama et al. |
| 3,870,727 | A | 3/1975 | Powell et al. |
| 3,959,312 | A | 5/1976 | Mikolajczak et al. |
| 4,042,617 | A | 8/1977 | Kogure et al. |
| 4,131,747 | A | 12/1978 | Kurono et al. |
| 4,132,720 | A | 1/1979 | Mohrbacher et al. |
| 4,152,214 | A | 5/1979 | Delfel et al. |
| 4,152,333 | A | 5/1979 | Mikolajczak et al. |
| 4,154,840 | A | 5/1979 | Ondetti et al. |
| 4,178,286 | A | 12/1979 | Wasserman et al. |
| 4,203,996 | A | 5/1980 | Mikolajczak et al. |
| 4,252,728 | A | 2/1981 | Delay |
| 4,409,236 | A | 10/1983 | Bosies et al. |
| 4,430,339 | A | 2/1984 | Eistetter et al. |
| 4,619,888 | A | 10/1986 | Kawata et al. |
| H271 | H | 5/1987 | Whaun |
| 4,675,318 | A | 6/1987 | Liu |
| 4,783,454 | A | 11/1988 | Liu |
| 4,808,629 | A | 2/1989 | Liu |
| 4,849,524 | A | 7/1989 | Henning et al. |
| 4,870,208 | A | 9/1989 | Chan et al. |
| 5,081,240 | A | 1/1992 | Bousquet et al. |
| 5,084,582 | A | 1/1992 | Genet et al. |
| 5,256,803 | A | 10/1993 | Duchesne et al. |
| 5,334,730 | A | 8/1994 | Fritz-Langhals |
| 5,502,221 | A | 3/1996 | Sayo et al. |
| 5,677,470 | A | 10/1997 | Tsujihara et al. |

(Continued)

FOREIGN PATENT DOCUMENTS

| | | |
|---|---|---|
| CA | 2324895 | 3/1999 |
| FR | 98 03492 | 3/1998 |

(Continued)

OTHER PUBLICATIONS

U.S. Appl. No. 60/278,673, filed Mar. 21, 2001, Robin et al.

(Continued)

*Primary Examiner* — Brenda Coleman
(74) *Attorney, Agent, or Firm* — Rona Nardone

(57) ABSTRACT

The present invention concerns a new general process for asymmetric hemisynthesis of harringtonines and their analogs, that are alkaloids used in chemotherapy. This process comprises direct esterification of a natural cephalotaxine with an acylating compound constituted of a side chain precursor which backbone and functionalization are entirely preformed. The invention also concerns a natural, synthetic or semi-synthetic harringtonines including their tautomeric forms and their salts of the following formula:

wherein n=2 (i.e. harringtonine) or n=3 (i.e. homoharringtonine), in which the total content of impurities, possibly including enantiomeric forms, is lower than 1%, and/or the content of the major impurity is lower than 0.9%, and/or the chromatographic assay exhibits a harringtonines content higher than 97.5%.

16 Claims, 13 Drawing Sheets

(56) References Cited

U.S. PATENT DOCUMENTS

| | | | |
|---|---|---|---|
| 5,834,467 | A | 11/1998 | Kalish et al. |
| 6,107,291 | A | 8/2000 | Russo-Rodriguez et al. |
| 6,613,900 | B2 | 9/2003 | Robin et al. |
| 6,831,180 | B1 | 12/2004 | Robin et al. |
| 7,683,050 | B2 | 3/2010 | Brown |

FOREIGN PATENT DOCUMENTS

| | | | |
|---|---|---|---|
| FR | 2 776 292 | | 9/1999 |
| FR | 2776292 | A | 9/1999 |
| FR | 2 818 970 | | 7/2002 |
| JP | 58-32880 | | 2/1983 |
| JP | 58032880 | | 2/1983 |
| WO | 92/01696 | A1 | 1/1992 |

OTHER PUBLICATIONS

Abraham et al., Single Crystal X-Ray Structures of Chemotherapeutic Agents II, Tetrahedron Letters (1969), No. 46, pp. 4085-4086. Pregman Press, Great Britain.

Studies on Alkaloids of Cephlotaxus Sinensis (Rehd. et Will.) Li, Alkaloids Group, Laboratory of Plant Chemistry, Institute of Botany, Academia Botanica Sinica (1980), 22(2).

Ancliff et al., Synthesis of the ester side chains of some potently antileukemic harringtonia alkaloids from chiral citrates, Chem. Commun. (2006), pp. 3243-3245.

Arora et al., Crystal and Molecular Structure of Cephalotaxine, J. Org. Chem. (1976), 43(3), pp. 551-554.

Auerbach et al., The Total Synthesis of Cephalotaxine, J. Amer. Chem. Soc. (1972), pp. 7172-7173.

Berhal et al., Stereoselective Synthesis of Enantiopure Analogues of (−)-Cephalotaxine, Tetrahedron: Asymmetry (2010), 21, pp. 325-332.

Eckelbarger et al., Synthesis of Antiproliferative Cephalotaxus Esters and Their Evaluation against Several Human Hematopoietic and Solid Tumor Cell Lines: Uncovering Differential Susceptibilities to Multidrug Resistance, Chemistry Eur. J. (2008), 14(14), pp. 4293-4306.

Eckelbarger, et al., Strain-Release Rearrangement of N-Vinyl-2-Arylaziridines. Total Synthesis of the Anti-Leukemia Alkaloid (−)-Deoxyharringtonine, J. Am. Chem. Soc. (2006), 128, pp. 10370-10371.

Guanghong et al., The Crystal Structures of Harringtonine and Homoharringtonine, Acta Acad. Med. Sinica (1988), 10(4), pp. 283-287 (with Engl. Translation).

He et al., Stability-indicating LC assay of and impurity identification in homoharringtonine samples, J. Pharma. and Biomedical Analysis (2000), vol. 22, pp . 541-554.

Hiranuma et al.; Studies in Cephalotaxus Alkaloids. Stereospecific Total Synthesis of Homoharringtonine, J. Org. Chem. (1983), 48, pp. 5321-5326.

Hiranuma et al., Synthesis of homoharringtonine and Its Derivative by Partial Esterification of Cephalotaxine, Tetrahedron Lett. (1982), 23(34), pp. 3431-3434.

Huang et al., Chapter 3: Cephalotaxus Alkaloids, The Alkaloids (1988), vol. XXIII, pp. 157-226.

Hudlicky et al., Chapter 5: Synthesis of Cephalotaxine Alkaloids, pp. 639-691, 1998.

Isono et al., Total Synthesis (−)-Cephalotaxine, J. Org. Chem. (1995), 60, pp. 115-119.

Kantarjian et al., Homoharringtonine History, Current Research, and Future Directions, American Cancer Society (2001), 92(6), pp. 1591-1605.

Keng et al., Synthesis of Homoharringtonine and Separation of its Stereoisomers, Asta Chimica Sinica (1985), 43, pp. 161-167.

Kexue Tongbao, The Partial Synthesis of Harringtonine, Study the Theory of the Dictatorship of the Proletariat, vol. 20, No. 9, 1975 (with English Translation).

Kim et al., Characterization of solvent induced crystalline and amorphous homoharringtonine, Korean J. Chem. Eng. (2009), 26(4), pp. 1090-1093.

Leroux, Preparation of Tetrahydrofuran and Tetrahydropyran Nitriles by the Action of CuCN on γ-and 8-Halogenated Ketones, Laboratoire de Synthese Organicque, pp. 1-22, 1967.

Leroux, "Obtention de nitriles tetrahydrfuranniques et tetrahydropyranniques par action du CuCN surlesc'etones gamma et delta halogenees", Bulletin De La Societe Chimique De France, No. 1, 1968, pp. 344-351, XP002087586, Paris, France, Translator's Reports/Comments, 2011, (with English Translation).

Li et al.; Concise Total Synthesis of (±)-Cephalotaxine via a Transannulation Strategy: Development of a Facile Reductive oxy-Nazarov Cyclization, Organic Letters American Chemical Society, 2011.

Liang et al., Partial Synthesis of Harringtonine, Scientia Sinica (1979), 22(11), pp. 1335-1345.

Miah et al., Chapter 2: Cephalotaxus Alkaloids, The Alkaloids, vol. 51, pp. 199-269, 1998.

Mikolajczak et al., Deoxyharringtonine, A New Antitumor Alkaloid from Cephalotaxus: Structure and Synthetic Studies, Tetrahedron (1971), vol. 28, pp. 1995-2001.

Nagasaka et al.; 1-Azaspiro[4.4]nonane-2,6-dione and the Separation and Absolute Configurations of its Enantiomers, Tetrahedron: Asymmetry (1997), 8(2), pp. 191-194.

O'Dwyer et al., Homoharringtonine-Perspectives on an Active New Natural Product, Journal of Clinical Oncology (1986), 4(10), pp. 1563-1568.

Paudler et al., The Alkaloids of Cephalotaxus Drupacea and Cephalotaxus Fortunei, Department of Chemistry, Ohio University (1963), vol. 28, pp. 2194-2197.

Planas et al., Stereoselective Synthesis of (−)-Cephalotaxine and C-7 Alkylated Analogues, J. Org. Chem. (2004), vol. 69, pp. 3087-3092.

Powell et al., Antitumor Alkaloids from Cephalotaxus Harringtonia: Structure and Activity (1972), 61(8), pp. 1227-1230.

Powell, Structures of Homoerythrina Alkaloids from Cephalotaxus Harringtonia, Phytochemistry (1972), vol. 11, pp. 1467-1972.

Robin et al., The First Semi-Synthesis of Enantiopure Homoharringtonine via Anhydrohomoharringtonine from a Preformed Chiral Acyl Moiety, Tetrahedron Lett. (1999), 40, pp. 2931-2934.

Shu-Wen et al., A Study on the Deoxyharringtonine and its Analogues, Acta Chimica Sinica, Shanghai Institute of Mayeria Medica (1975), pp. 75-78 (with English Translation).

Smith et al., The Genus Cephalotaxus: Source of Homoharringtonine and Related Anticancer Alkaloids, Cancer Treatment Reports 1976), 60(8), pp. 1157-1170.

Suffness et al., Chapter 1: Antitumor Alkaloids, The Alkaloids (1985),vol. XXV, pp. 57-69 and 295-298.

Takeda et al. Antitumor Activities of Harringtonine and Homoharringtonine, Cephalotaxus Alkaloids Which Are Active Principles From Plant by Intraperitoneal and Oral Administration, J. Pharm. Dyn. (1982), 5, pp. 841-847.

Taniguchi et al., Short Synthesis of (--)-Cephalotaxine Using a Radical Cascade, Organic Letters (2008), 10(18), pp. 4129-4131.

Wang et al., Studies on Alkaloids of Cephlotaxus, VII Structures and Semi-Synthesis of Two Anticancer Cephalotaxine Esters, Acta Pharma. Sinica (1992), 27(3), pp. 173-177 (with Engl. Translation).

Wang et al., Studies on the Alkaloids of Cephalotaxus IX. Semi-Synthesis of Cephalotaxine Esters and Their Anti-Leukemic Activity, Acta Pharma. Sinica (1992), 23(3), pp. 178-184 (with Engl. Translation).

Wenkui et al., Synthesis of Deoxyharringtonine and Separation of its Steromers, Scientia Sinica (1980), 23(7), pp. 835-846.

Wilmot, Complex Botanical Natural Products: Synthesis of Cephalotaxus Esters and of the C19-Diterpenoid Skeleton of Aconitunm and Delphinium Alkaloids, 2010.

Yongji et al., Experimental Studies on the Toxicity of Harringtonine and homoharringtonine, Chinese Med. Journal (1979), 92(3), pp. 175-180.

H.A. Bates, "Decarbonylation of tetrahydrofuran-2-carboxylic acids and tetrahydropyran-2-carboxylic acids in concentrated sulfuric acid: formation of oxonium ions", Journal of the American Chemical Society, vol. 104, No. 9, 1982, pp. 2490-2493, XP002087583.

(56) References Cited

OTHER PUBLICATIONS

P.G.M. Wuts et al, "An electrochemical ketal synthesis from 2-carboxy-2-allyl-tetrahydropyrans", Tetrahedron Letters, vol. 23, No. 39, 1982, pp. 3987-3990, XP002087584, Oxford, GB.
M. Nagai et al, "The stereochemistry of protopanaxadiol. The absolute configuration of C(20) of dammarenediol-I- and -II", Tetrahedron Letters, No. 40, 1966, pp. 4797-4801, XP002087585, Oxford, GB.
K.L. Mikolajczack et al, "Preparation and Antitumor Activity of a Rearranged Ester of Cephalotaxine", J. Med. Chem., vol. 18, No. 1, pp. 63-66, (1975).
D.Z. Wang et al, Yaoxue Xuebao, vol. 27, p. 178 (1992).
D.Z. Wang et al, Yaoxue Xuebao, vol. 27, p. 173 (1992).
Thomas Hudlicky et al., "Synthesis of Cephalotaxine Alkaloids", *The Alkaloids,* vol. 51, Chapter 5, pp. 639-691, 1998, Academic Press, Burlington, MA, USA.
M.A. Miah et al., "Cephalotaxine Alkaloids", *The Alkaloids,* vol. 51, Chapter 2, pp. 199-264, 1998, Academic Press, Burlington, MA, USA.
Cecil R. Smith, Jr. et al., "*Harringtonine and Related Cephalotaxine Esters",* Anticancer Agents based on Natural Product Models, Chapter II, vol. 16, pp. 391-416, 1980, Academic Press, New York, New York, USA.
Wen-Kui Huang et al., "Synthesis of Deoxyharringtonine and Separation of its Stereomers", *Sci. Sin.,* vol. 23, No. 7, pp. 835-846,1980, Chinese Academy of Sciences, Beijing, China.
Liang Huang et al., "Cephalotaxus Alkaloids", *The Alkaloids,* vol. 51, Chapter 3, pp. 157-227, 1999, Academic Press, Burlington, MA, USA.
Anonymous, *Acta Bot. Sin.22:*156 (1980) cited by Huang, L, et al., "Cephalotaxus Alkaloids", *The Alkaloids* vol. XXII, pp. 157 (1988).
International Search Report from PCT/IB02/02054 issued Nov. 18, 2002.
French Preliminary Search Report from FR 9803492, issued Dec. 14, 1998.
Ciurdaru et al., PL 103334, CA 121:255399, 1994.
Reich et al., Biorg. Med. Chem. Lett. "Derivatives of D-Penicillamine as Potential Antiarthritic Agents", 4(0):1167-70 1994.
Lemmens et al., Journal of Organic Chemistry, "Synthesis of α, β-Epoxyacyl Azides and Their Rearrangement to Epoxy Isocyanates and 3- and 4-Oxazolin-2-ones", 49:2231-2235 (1984).
Johnson et al., "Dianions Derived from α-Halo Acids. The Darzens Condensation Revisited", Journal of Organic Chemsitry, 47:1205-1212 (1982).
Newman, M.S., et al., "The Darzens Glycidic Ester Condensation", *Organic Reactions,* vol. V, Chapter 10, pp. 413-440 (1949), John Wiley & Sons, New York, NY, USA.
Kulesza et al., PL 85803, CA 90: 121390 (1979).

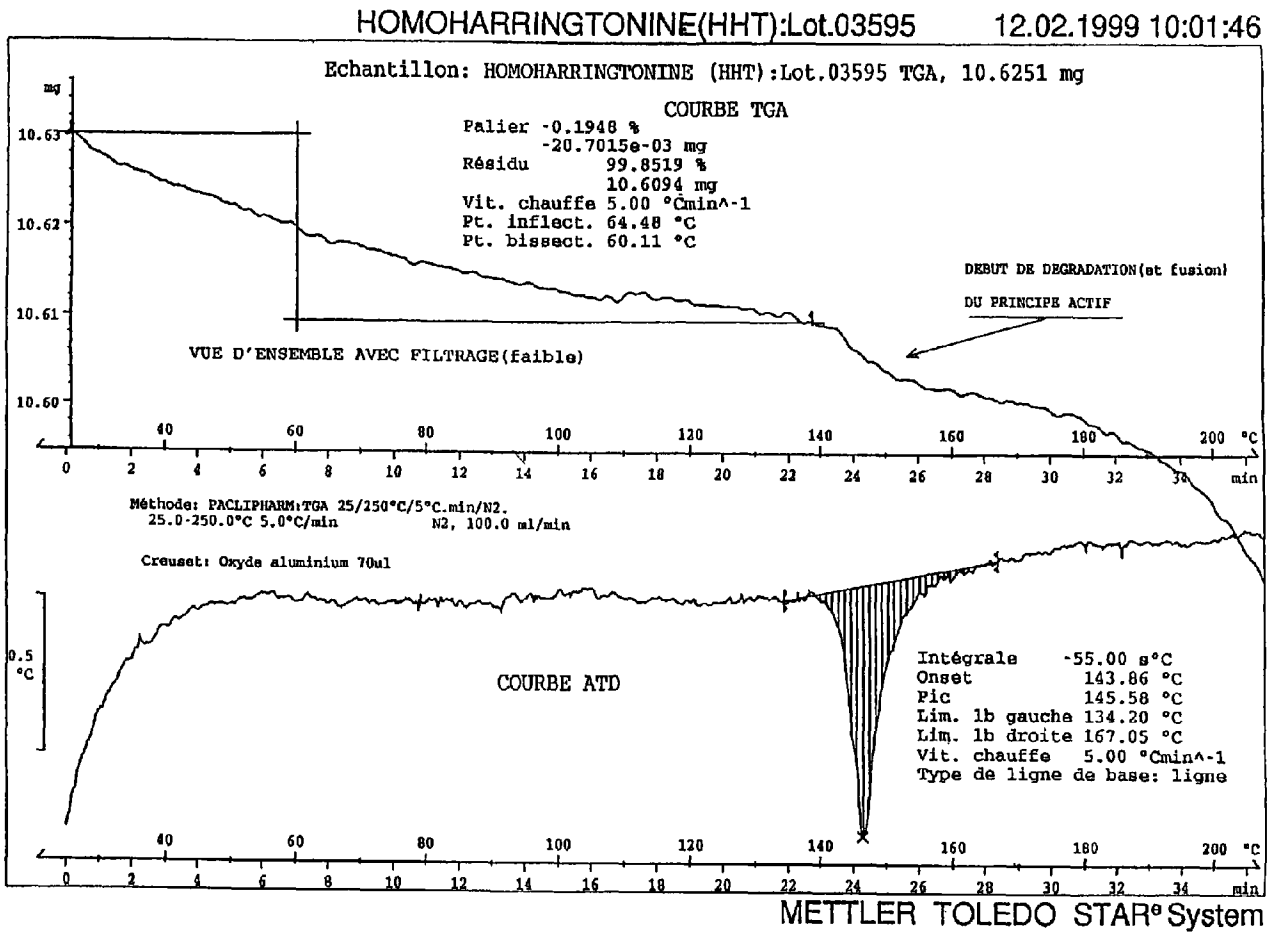
FIGURE 3: TYPICAL DSC THERMOGRAM FOR IDENTIFICATION OF CRYSTALLINE HOMOHARRINGTONINE

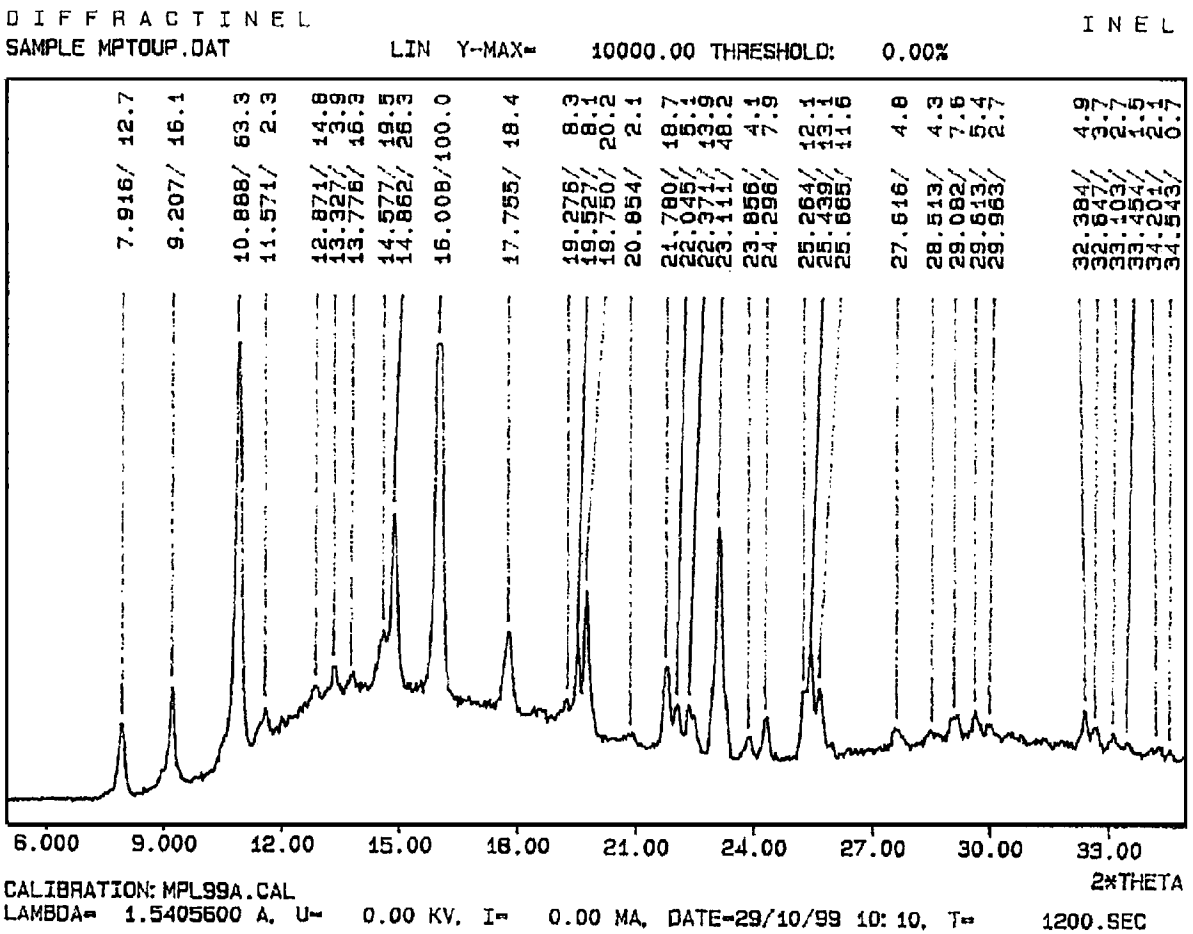
FIGURE 4: TYPICAL POWDER X-RAY DIFFRACTOGRAM FOR IDENTIFICATION OF CRYSTALLINE HOMOHARRINGTONINE

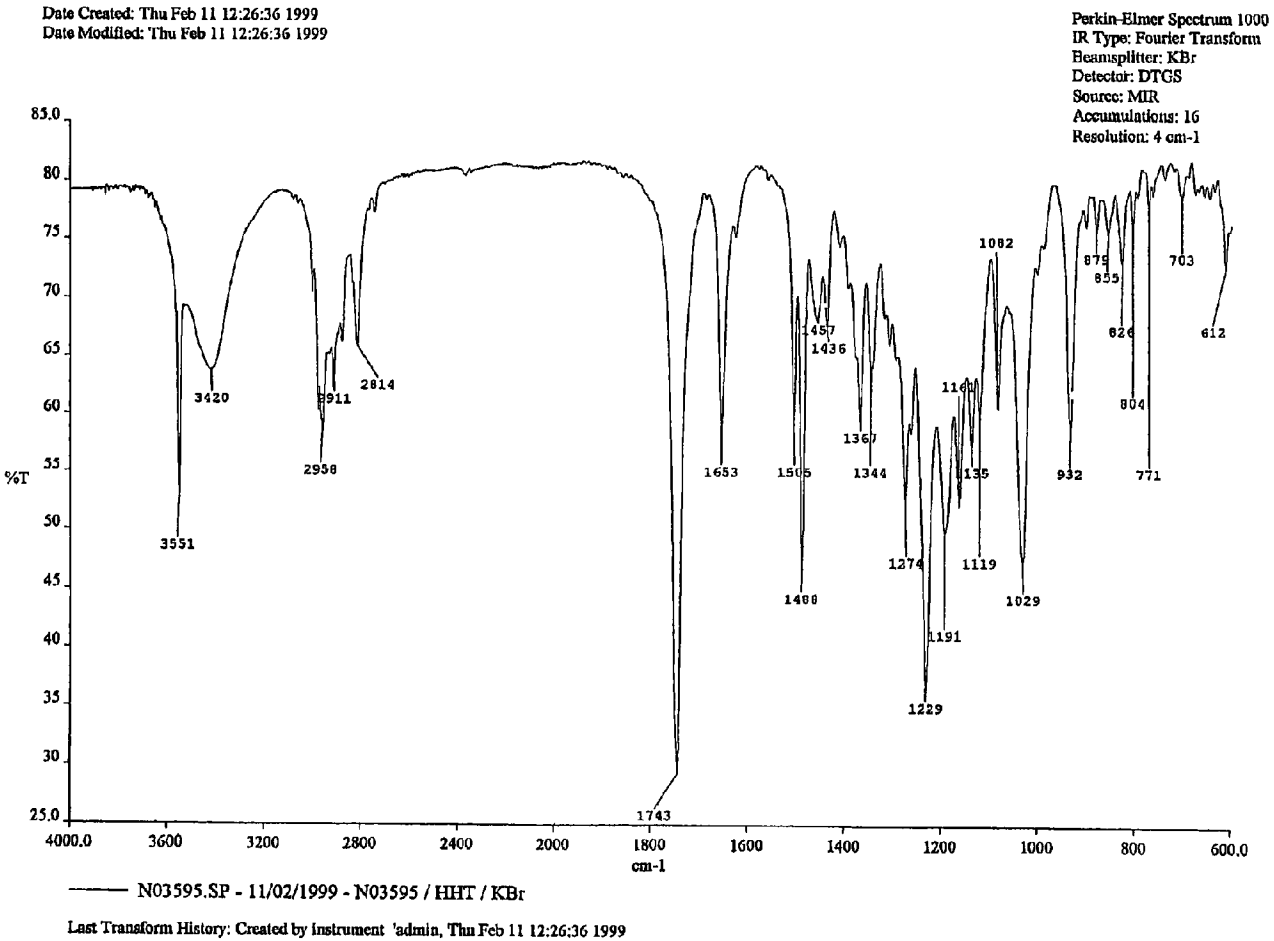
FIGURE 5 : INFRARED R SPECTRUM (KBr)
FOR IDENTIFICATION OF CRYSTALLINE HOMOHARRINGTONINE

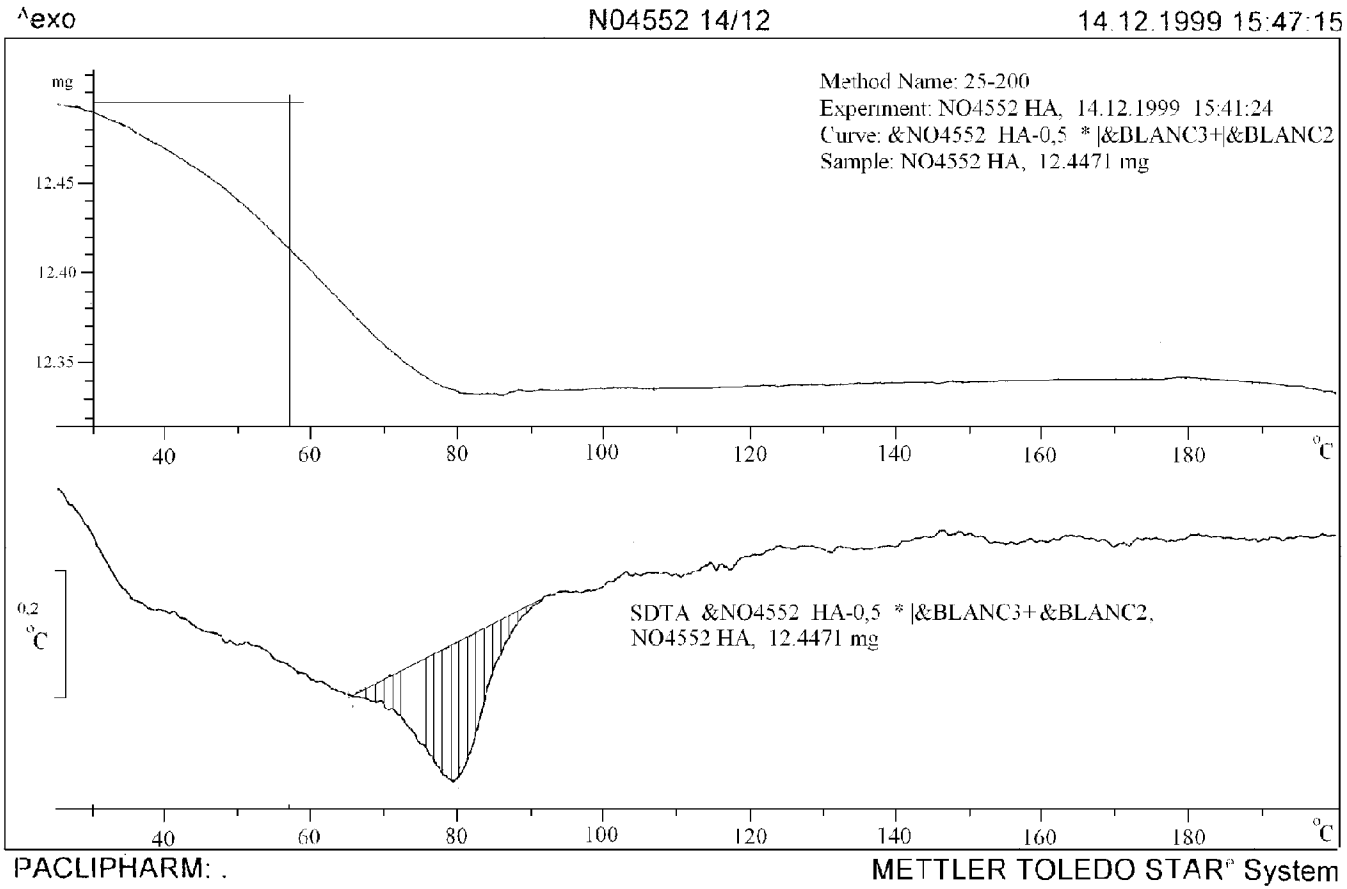
FIGURE 6 : TYPICAL DSC DIAGRAM FOR IDENTIFICATION OF CRYSTALLINE HARRINGTONINE

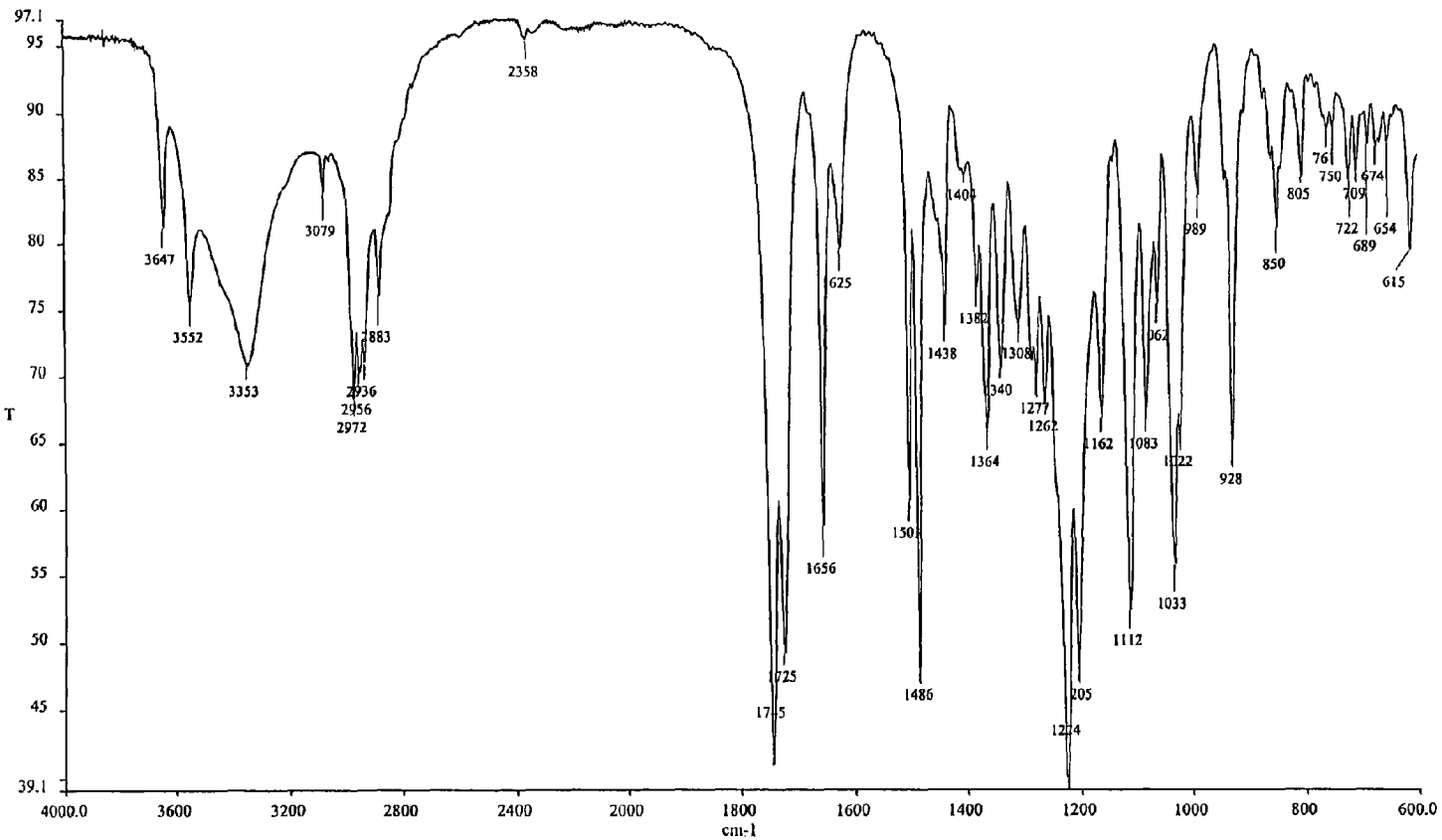
FIGURE 7: TYPICAL INFRARED SPECTRUM (KBr) FOR IDENTIFICATION OF CRYSTALLINE HARRINGTONINE

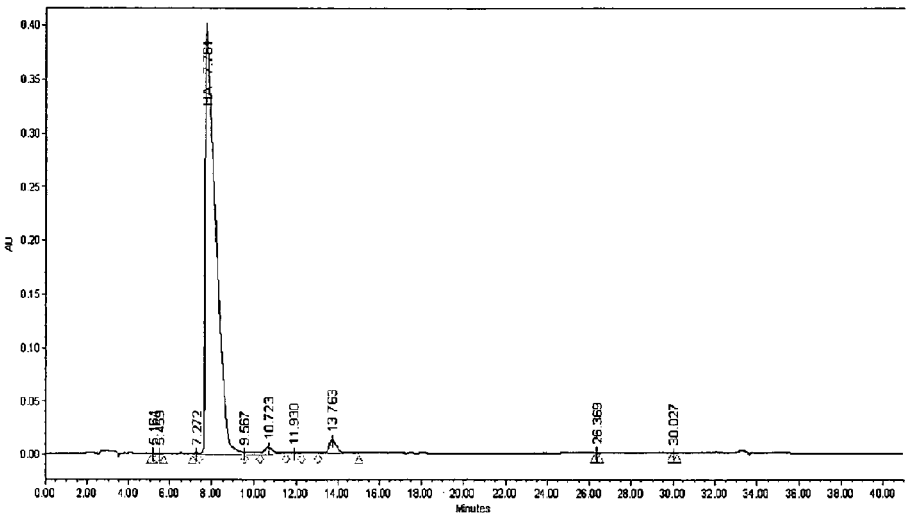
Figure 8: HPLC chromatogram of commercial natural harringtonine using UV detection
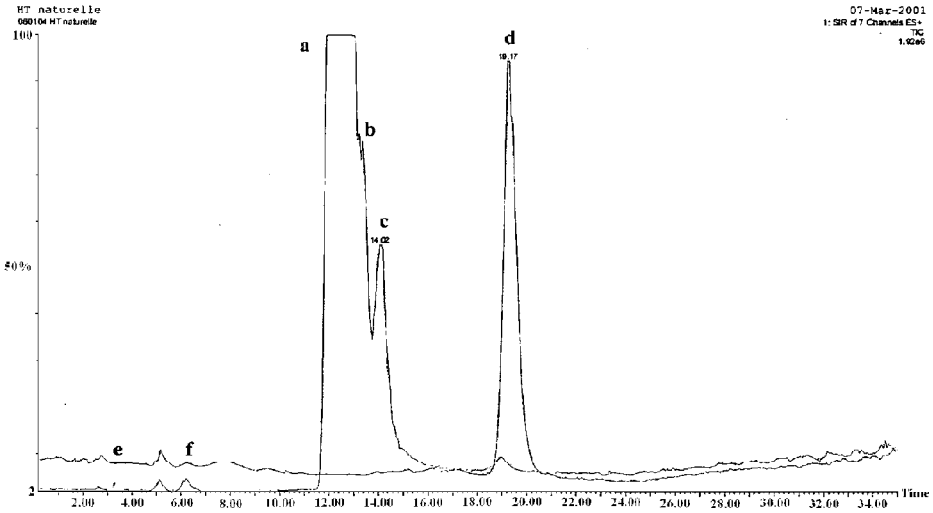
Figure 9: Enlarged chromatogram of commercial natural harringtonine using liquid chromatography coupled with mass spectrometry and UV detector

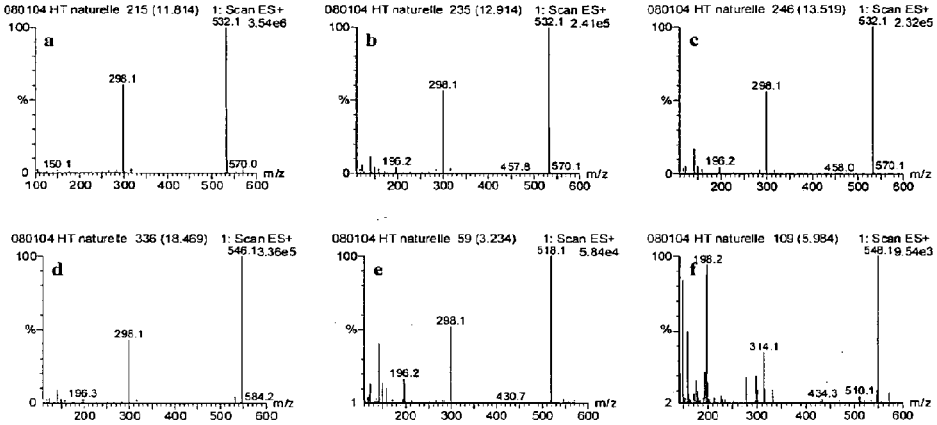

a: harringtonine; b,c: position isomer of harringtonine; d: homoharringtonine; e: 4'-demethyl harringtonine; f: drupacine derivative

Figure 10: Identification of major impurities of commercial natural harringtonine using liquid chromatography coupled with mass spectrometry and UV detector

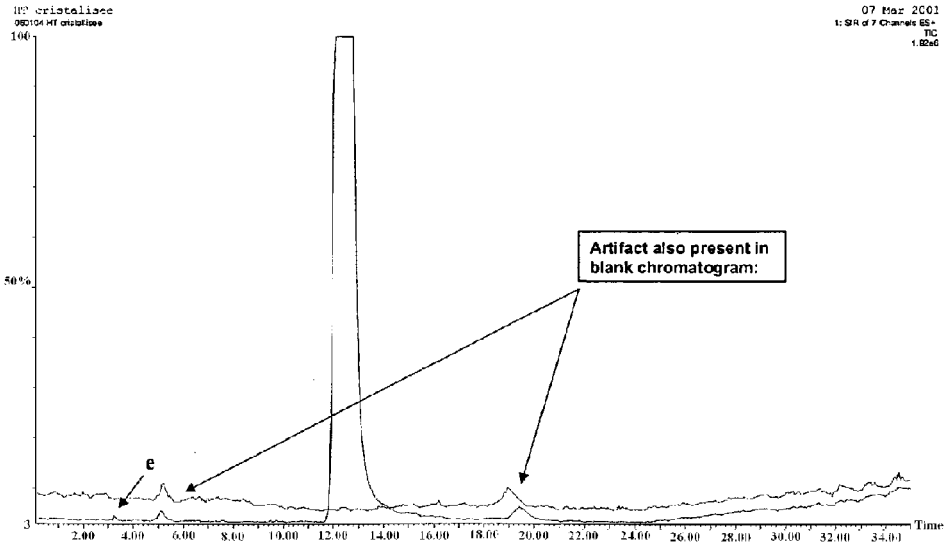

Figure 11: Enlarged chromatogram of highly purified natural harringtonine using liquid chromatography coupled with mass spectrometry and UV detector

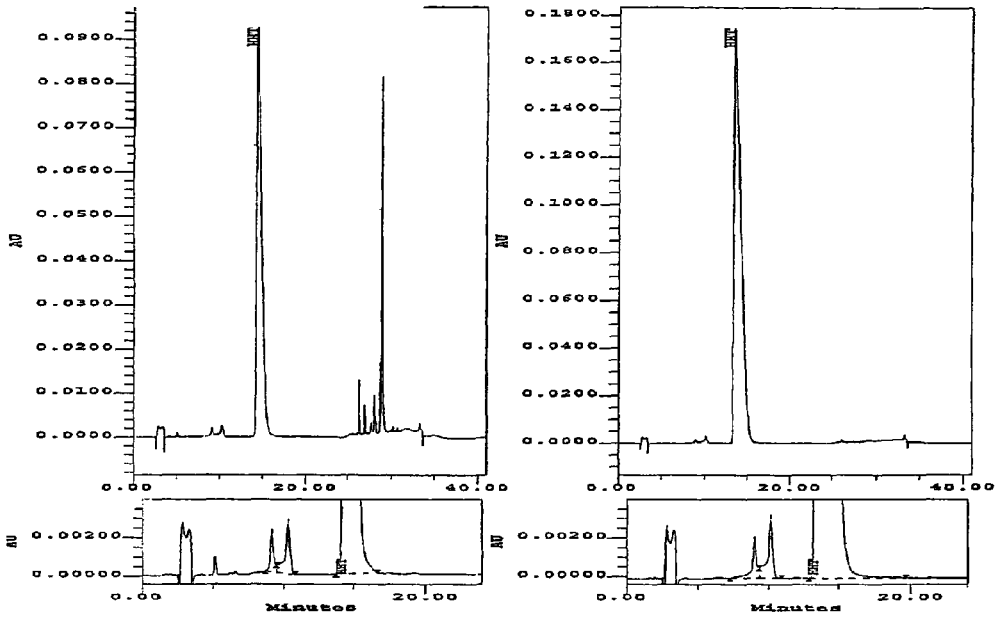
Figure 12: HPLC chromatogram showing the progression of purity between raw and chromatographied semi-synthetic homoharringtonine DS
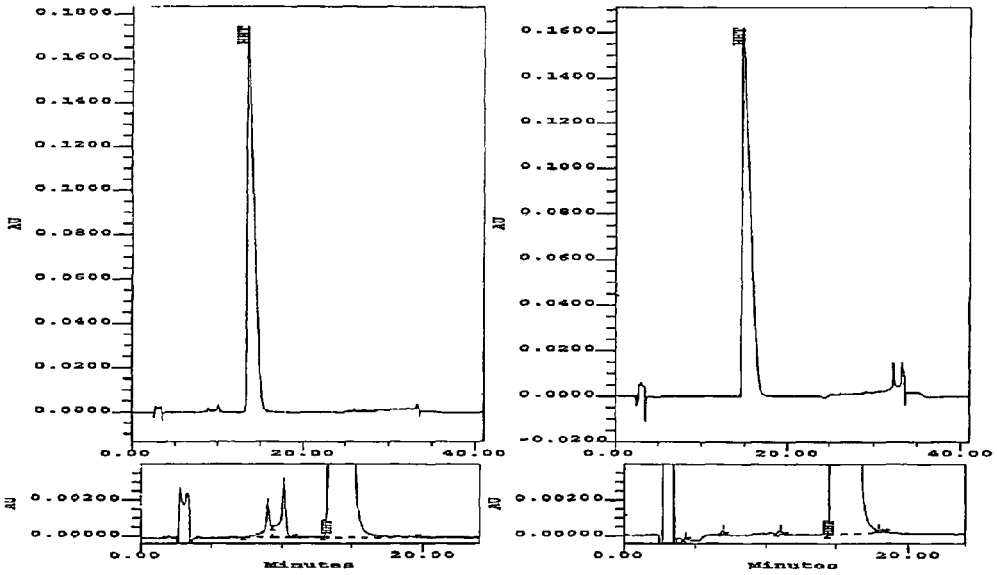
Figure 13 : HPLC chromatogram showing the progression of purity between chromatographied and crystallized semi-synthetic homoharringtonine DS

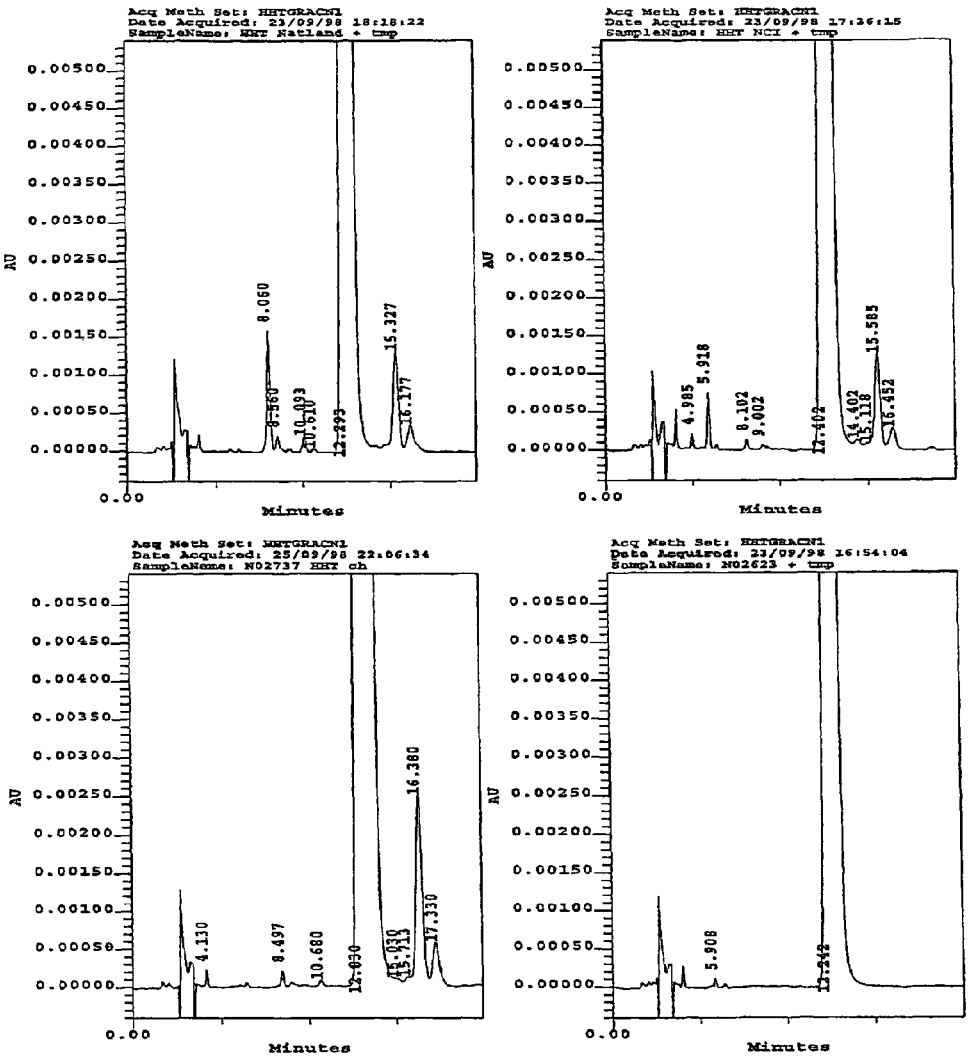

Figure 14: HPLC profiles of 3 samples of different natural sources

Top left — Natland sample (a U.S. distributor of Chinese material): main impurity content is at 0.8-1%;

Top right — NCI HHT Drug Substance purified: main impurity content is at 0.8-1%;

Bottom left — China National Pharmaceutical sample: main impurity content is at 1-1.2%;

Bottom Right — Purified Homoharringtonine: main impurity content is at 0.05 %

CEPHALOTAXANE DERIVATIVES AND THEIR PROCESSES OF PREPARATION AND PURIFICATION

Matter enclosed in heavy brackets [ ] appears in the original patent but forms no part of this reissue specification; matter printed in italics indicates the additions made by reissue.

This application, *13/661,677 is a reissue of U.S. patent application Ser. No. 11/440,648 filed May 25, 2006, which* is a continuation of U.S. patent application Ser. No. 10/877,067, [pending] *now U.S. Pat. No. 7,169,774*, which was filed Jun. 25, [1004] *2004*, which was a continuation-in-part of U.S. patent application Ser. No. 09/270,006, now U.S. Pat. No. 6,831,180, which was filed Mar. 16, 1999 and claims the benefit of French Appln. No. 98 03492 under 35 U.S.C. §119(a), which was filed Mar. 20, 1998. It further is a continuation-in-part of U.S. patent application Ser. No. 10/472,299, now abandoned, a filing under 35 U.S.C. §371 having an international filing date of Mar. 21, 2002 and claiming priority to U.S. Provisional Patent Appln. No. 60/278,673 which was filed Mar. 21, 2001[, and is now abandoned]. The priority documents are hereby incorporated by reference for all purposes.

The present invention relates to a process for preparing cephalotaxane derivatives bearing a side chain. It further relates to highly purified and crystalline forms of harringtonines and their process of preparation by purification of crude alkaloids from natural, synthetic or semi-synthetic sources. The acquisition of highly purified and crystalline forms of harringtonines allows their use for blending in pharmaceutical compositions, especially as directed to the treatment of cancer through oral administration.

The term "cephalotaxanes" refers to compounds or salts thereof which have a basic skeleton of formula

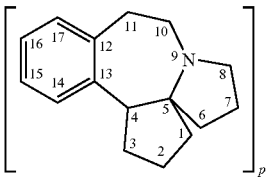

where p is equal to 1 or 2 (it being possible for the two units to be identical or different and linked via a single bond or an oxygen atom), which can contain various oxygenated substituents (aliphatic or aromatic ethers, free or esterified alcohols, substituted or free enols and/or phenols, bridged ethers, and more generally any substituent usually encountered in the natural state on compounds of this type).

Harringtonines are alkaloids which are of high interest in anticancer chemotherapy, in particular on certain haematosarcomas which are multi-resistant to the existing therapies. The selectivity of harringtonines, which is based on a novel mechanism of action relating to protein synthesis, is such that this series is favoured with a great future in anticancer therapy.

Several literature compilations give a seemingly exhaustive review of all of the knowledge relating to cephalotaxanes, these compilations being, chronologically: [C. R. Smith, Jr, R. G. Powell and K. L. Mikolajczack, Cancer Treat. Rep., Vol. 60, 1157 (1976); C. R. Smith, Jr, L. Kenneth, K. L. Mikolajczack and R. G. Powell in "Anticancer Agent Based on Natural Product Model", 391 (1980); Liang Huang and Zhi Xue in "The Alkaloids", Vol. XXIII (A. Brossi Ed.), 157 (1984); M. Suffness and G. A. Cordell in "The Alkaloids, Chemistry and Pharmacology" (A. Brossi Ed.), Vol. 25, 57-69, 295-298 (1987); P. J. O'Dwyer, S. A. King, D. F. Hoth, M. Suffness and B. Leyland-Jones, Journal of Clinical Oncology 1563 (1986); T. Hudlicky, L. D. Kwart and J. W. Reed, in "Alkaloid: Chemical and Biological Perspectives" (S. W. Pelletier Ed.), Vol. 5, 639 (1987); M. A. Miah, T. Hudlicky and J. Reed in "The Alkaloids", Vol. 51, 199 (1998)].

Antiparasitic activities, in particular on the haematozoon of malaria, have also been recognized [J. M. Whaun and N. D. Brown, Ann. Trop. Med. Par., Vol. 84, 229 (1990)].

Homo-harringtonine (HHT), the most active member of the series, is active at and above daily doses of 2.5 mg/m$^2$ of body area per 24 hours, i.e., as a guide, at doses twenty times lower than that for Taxol. HHT has already undergone fourteen phase I and II clinical trials and it is the only known product capable of a 70% reinduction of full haematological remissions in patients suffering from chronic myeloid leukaemias that have become resistant to alpha-interferon [S. O'Brien, H. Kantarjian, M. Keating, M. Beran, C. Koler, L. E. Robertson, J. Hester, M. Rios, M. Andreeff and M. Talpaz, Blood, 332 (1995); Leukemia Insights, Vol. 3, No. 1 (1998)].

Harringtonines were extracted over 35 years ago from an exclusively Asiatic cephalotaxacea known as Cephalotaxus harringtonia, following the programme of research into novel anticancer agents in the plant kingdom developed by the National Cancer Institute. In fact, the Cephalotaxus alkaloids consist essentially (at least 50%) of cephalotaxine, a biosynthetic precursor of the harringtonines, the latter individually representing only a few percent of the total alkaloids.

Besides their low concentration in the natural state in plant starting material, harringtonines are mixed with many congeners which have very similar chemical structures. Thus, in a high resolution high performance liquid chromatography (HPLC) chromatogram of a semi-purified alkaloid extract, no less than several tens of cephalotaxine esters are counted.

If we consider that:

on the one hand, harringtonines are generally relatively non-crystallogenic, as is suggested by the flexibility of their side chains, which are generally branched and aliphatic, on the other hand, these esters, in particular harringtonine and homo-harringtonine, are contaminated with congeners which are themselves biologically active and very difficult to separate out, even by high resolution analytical HPLC, the current state of the art does not allow these compounds to be produced viably on the industrial scale as regards the purity required for pharmaceutical active principles.

Although biosynthetically similar to the alkaloids of the genus Erythrina, cephalotaxanes are alkaloids which have a unique structure in nature, encountered only in the genus Cephalotaxus, which is the only genus of the Cephalotaxacea family. On the other hand, the side chains of the various harringtonine congeners are all derived from the methyl hemiester of the primary carboxyl of (2R) citramalic acid 3a (see table p 156) by substitution of the tertiary methyl using alkyl or aralkyl radicals which may themselves be unsubstituted or substituted with tertiary hydroxyls, it then being possible for the latter to form a cyclic ether with a tertiary alcohol (anhydro derivatives).

The table p 156 shows the main examples of harringtonine congeners, which all have significant cytostatic activity to different degrees. None of the artificial analogous table p 156) and lack significant cytostatic activity.

It is worthwhile pointing out that, although botanically very similar to the Cephalotaxaceas, Taxaceas contain triterpene alkaloids (taxines), accompanied by non-alkaloid triterpenes, taxanes, which are also of unique structure in nature. Although they are completely different from taxanes in terms of chemical structures and anticancer mechanism of activity, the harringtonines have analogy with taxanes in more than one respect:

they have cytostatic properties, they consist of a polycyclic skeleton, an inactive biosynthetic precursor of the complete structure, onto which is grafted a side chain containing a similar combination of hydrophilic and hydrophobic substituents, the polycyclic part of the taxanes (baccatins in the broad sense) and of the harringtonines (cephalotaxines) is relatively abundant in renewable parts of the plant, whereas the active molecules (harringtonines and taxanes) are ten to one hundred times less abundant therein, the plum yew (Cephalotaxus) is a rare tree, even rarer than the yew (Taxus), and is much less ubiquitous than the latter.

It results from the above facts that, following the manner of the semi-synthesis of taxanes by adding a synthetic chain to a 10-deacetylbaccatin III of extracted origin, the asymmetric semi-synthesis of harringtonines by esterification of a cephalotaxine of natural origin is of considerable medical and economic value. Furthermore, the current population of Cephalotaxus is relatively reduced even in their original habitat. Thus, during its importation into Europe for ornamental purposes last century, Cephalotaxus harringtonia was already no longer present in spontaneous form in eastern China and in northern Japan. The use of a precursor present in a renewable part of the tree (the leaf) in order to prepare homo-harringtonine semi-synthetically is thus of considerable environmental interest, all the more so since the total synthesis of optically active cephalotaxine has not been achieved hitherto, despite the extensive synthetic studies carried out in this respect (a certain number of laborious syntheses of racemic cephalotaxine containing 10 to 15 steps have, however, been carried out: see bibliographic review above).

Consider that several hundred tonnes per year of this rare and very slow-growing tree (even slower growing than Taxus sp.) need to be extracted to satisfy the current market needs for homo-harringtonine (several kilograms per year), whereas the semi-synthesis would consume only a few tonnes of renewable parts of the tree (leaves). Furthermore, homo-harringtonine (HHT) of natural origin currently available on the active principles market is contaminated with its congeners, which, on account of their structural similarity, are very difficult to separate, even by "preparative" high performance liquid chromatography.

First of all, it should be noted that since the use of cephalotaxine itself as a source for semi-synthesis has not yet been economically justified, no process for selectively extracting this substance has been described hitherto. Moreover, among the active compounds, only harringtonine and isoharringtonine have been the subject of American patent applications for their preparation by extraction [R. G. Powell et al., U.S. Pat. No. 3,793,454 and U.S. Pat. No. 3,870,727]. Harringtonine has been the subject of a Japanese patent [JP 58-032,880] and deoxyharringtonine has been the subject of an American patent [U.S. Pat. No. 3,959,312]. As regards the preparation of homo-harringtonine itself, it has been the subject of only a few semi-synthetic studies [T. Hudlicky, L. D. Kwart and J. W. Reed in "Alkaloid: Chemical and Biological Perspectives" (S. W. Pelletier Ed.), Vol. 5, 639 (1987); M. A. Miah, T. Hudlicky and J. Reed in "The Alkaloids", Vol. 51, 199 (1998)], but no patent application has been made regarding a semi-synthesis process or even an extraction process.

Another aspect which gives the present invention an even greater advantage is that cephalotaxine can serve as a springboard for the synthesis of cephalotaxoids and harringtoids which are useful for antitumour (cancerous and non-cancerous tumours), antiparasitic, antifungal, antiviral and antibacterial chemotherapies.

Harringtonines consist of a complex alkaloid polycyclic alcohol (cephalotaxine), esterified with a side chain, in isolation having no more biological activity than cephalotaxine, but essential for the biological activity of the whole. Saponification of the side chain under harsh conditions leads to the cephalotaxine free base and to harringtonic acids. The attachment of the side chains takes place at the end of the biosynthesis. It has been demonstrated that catabolism leading to this reaction could be triggered in vivo under the influence of environmental or physiological stress exerted on the plant [N. E. Delfel, Phytochemistry, 403 (1980)].

Cephalotaxine, the polycyclic part consisting of 5 fused rings, has a novel arrangement which is unique in nature, i.e. a benzodioxoazepine onto which is fused a spiropyrrolidinopentenediol system. Cephalotaxane contains four asymmetric centres: three "asymmetric carbons" and a heterocyclic tertiary aminic nitrogen. The only reactive function is a secondary alcohol located in position 3, the methyl enol ether located in position 2 being potentially sensitive to proton attack. The whole forms a pseudohelical structure encaging the hydroxyl in the tube formed by the tetrahydrazepine. The base cephalotaxine readily forms highly crystallogenic stable salts (for example hydrochlorides and perhydrochlorides).

This alkaloid is relatively insensitive to basic media. On the other hand, several authors describe a certain level of sensitivity to acids and to quaternization of the nitrogen with methyl iodide, leading to a racemization by simultaneous inversion of the 3 asymmetric centres and of the nitrogen [D. J. Abraham, R. D. Rosensten and E. L. McGandy, Tetrahedron Letters, 4085 (1969)]. However, a period of several days in solution at pH 1-4 at 20° C. leaves this structure intact (personal observation).

This compound and its congeners which are not O-acylated in position 3 are biologically inactive.

All the side chains for harringtonines which have significant biological activity contain in common the 2-alkyl-2-carbomethoxymethyl-2-hydroxyacetyl unit. The alkyl chain, of variable length, has at the end either branching constituting an isopropyl bearing (harringtonine HT and homo-harringtonine HHT) or not bearing (deoxy-homo-harringtonine DHT) a tertiary alcohol, or a phenyl radical (for example the neo-harringtonine series most recently isolated). In the case of the anhydroharringtonines, the chain can be closed by dehydration between its two tertiary alcohols, for example forming a substituted tetrahydropyran ring. The tertiary carboxyl of this complex diester is borne by the single hydroxyl of the cephalotaxine. The only chiral centre on the side chain is located (to the ester junction. It contains, besides the first secondary chain, a hydroxyl which, on account of its tertiary nature, does not have the possibility of epimerizing.

The table p 157 shows synthetically the known processes for preparing harringtonines.

Several semi-syntheses of natural cephalotaxine esters and several series of analogues, which have simplified chains but give these analogues reduced cytotoxic activity, have been described hitherto, in particular those of deoxyharringtonine and of isoharringtonine. Most of them relate to simpler and less functionalized esters than those constituting HT and HHT, the esters which are most useful in chemotherapy [for example, deoxyharringtonine, isoharringtonine, T. Hudlicky, L. D. Kwart and J. W. Reed in "Alkaloid: Chemical and Biological Perspectives" (S. W. Pelletier Ed.), Vol. 5, 639 (1987)].

All the literature from 1972 to the present date [Mikolajczack et al., Tetrahedron, 1995 (1972); T. Hudlicky, L. D. Kwart and J. W. Reed in "Alkaloid: Chemical and Biological Perspectives" (S. W. Pelletier Ed.), Vol. 5, 639 (1987); M. A. Miah, T. Hudlicky and J. Reed in "The Alkaloids", Vol. 51, p. 236 (1998)] mention the impossibility hitherto of esterifying the highly sterically hindered secondary hydroxyl of cephalotaxane 2a with the tertiary carboxyl of the alkanoyl chain of harringtonic acid 3e totally preformed to give a harringtonine 4b, i.e. the conversion 2a+3e (4b as described in the example featured in the scheme below

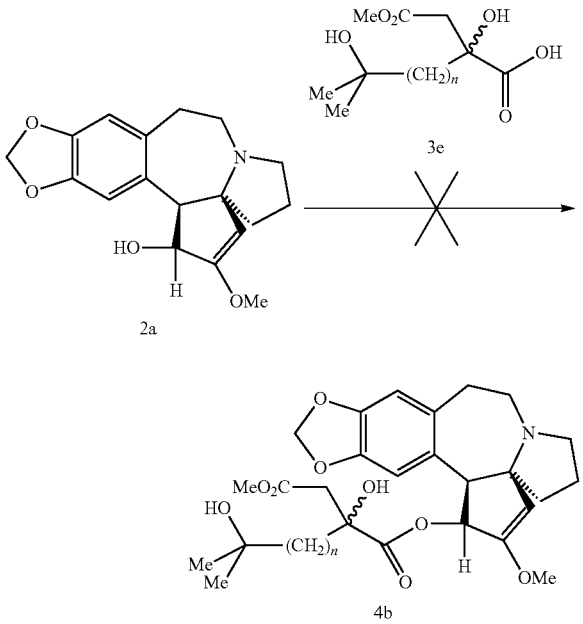

Most of the syntheses described hitherto thus involve binding of the secondary side chain —$CH_2CO_2Me$, i.e.: 1st) by the Reformatsky reaction between methyl bromoacetate and the carbonyl (real or potential) on the side chain prebound to cephalotaxine, in the presence of zinc, or 2nd) by prior formation of an organolithium reagent.

All the syntheses described thus consist in esterifying cephalotaxine using the (-keto alkanoyl chloride 7 lacking the end hydroxyl and containing neither the secondary chain located (to the tertiary carboxyl, nor the tertiary hydroxyl (to the carboxyl, to give 8 which is then converted into a harringtonine 4a, according to the reaction described below.

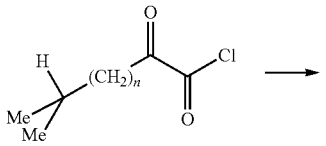

7

-continued

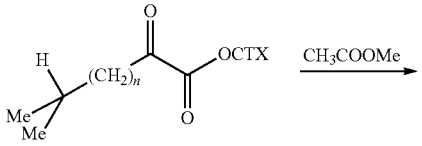

8

In formula 8, CTX—represents the cephalotaxyl radical of formula:

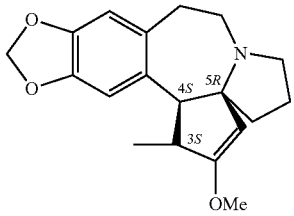

It should be noted that this (-hydroxyalkylation, which at the same time creates the chiral centre on the side chain, has never been achieved asymmetrically.

A few synthetic routes involve an esterification of cephalotaxine with a substituted hemisuccinyl chloride, optionally followed by subsequent introduction of the tertiary hydroxyl(s).

No O-acylation of cephalotaxine, using totally preformed and functionalized chiral chain precursors (to the tertiary carboxyl, has thus been achieved hitherto [T. Hudlicky, L. D. Kwart and J. W. Reed in "Alkaloid: Chemical and Biological Perspectives" (S. W. Pelletier Ed.), Vol. 5, pages 661 to 675 (1987); M. A. Miah, T. Hudlicky and J. Reed in "The Alkaloids", Vol. 51, pages 224 to 236 (1998)].

Consequently, the methods for preparing harringtonines by semi-synthesis, which have been described to date in the existing art, have the following drawbacks:

absence of stereoselectivity, poor convergence, mediocre yields, functionalization and construction of the chain on a rare and expensive substrate, chiral homo-harringtonine not obtained to date.

Since cephalotaxine is present in nature in partially racemized form [personal observation; Huang et al., Scientia Sinica, Vol. XXIII, 835 (1980)], the processes of the prior art which use a natural cephalotaxine as starting material can only theoretically result in partially racemized harringtonines.

A BRIEF DESCRIPTION OF THE FIGURES

FIGS. 1A and 1B gives the sequence of synthesis of homo-harringtonine corresponding to the Example 25, where A represents a 2,4,6-trichlorophenyl group, R represents a methyl and R' represents a cephalotaxyl moiety.

FIG. 3 shows a *typical* DSC curve for [a] *crystalline* homo-harringtonine.

FIG. 4 shows [an] *a typical* X-ray diffractogram for [a] *crystalline* homoharringtonine.

FIG. 5 shows an IR spectrum, in [KBR] *KBr* for [a] *crystalline* homoharringtonine.

FIG. 6 shows a *typical* DSC curve for [a homoarringtonine] *crystalline harringtonine*.

FIG. 7 shows [an] *a typical* IR spectrum, in [KBR] *KBr* for [a homoharringtonine] *crystalline harringtonine*.

FIG. 8 shows an HPLC chromatogram of commercial, natural harringtonine using UV detection.

FIG. 9 shows an enlarged chromatogram of commercial, natural harringtonine using liquid chromatography coupled with mass spectrometry and a UV detector.

FIG. 10 shows identification of major impurities of commercial natural harringtonine using liquid chromatography coupled with mass spectrometry and a UV detector.

FIG. 11 shows an enlarged chromatogram of highly purified natural harringtonine using liquid chromatography coupled with mass spectrometry and a UV detector.

FIG. 12 shows an HPLC chromatogram showing the progression of purity between raw and chromatographed semi-synthetic homoharringonine DS.

FIG. 13 shows an HPLC chromatogram showing the progression of purity between chromatographed and crystallized semi-synthetic homoharringtonine DS.

FIG. 14 shows HPLC profiles of three samples of different natural sources.

DEFINITIONS

Figure 1A:
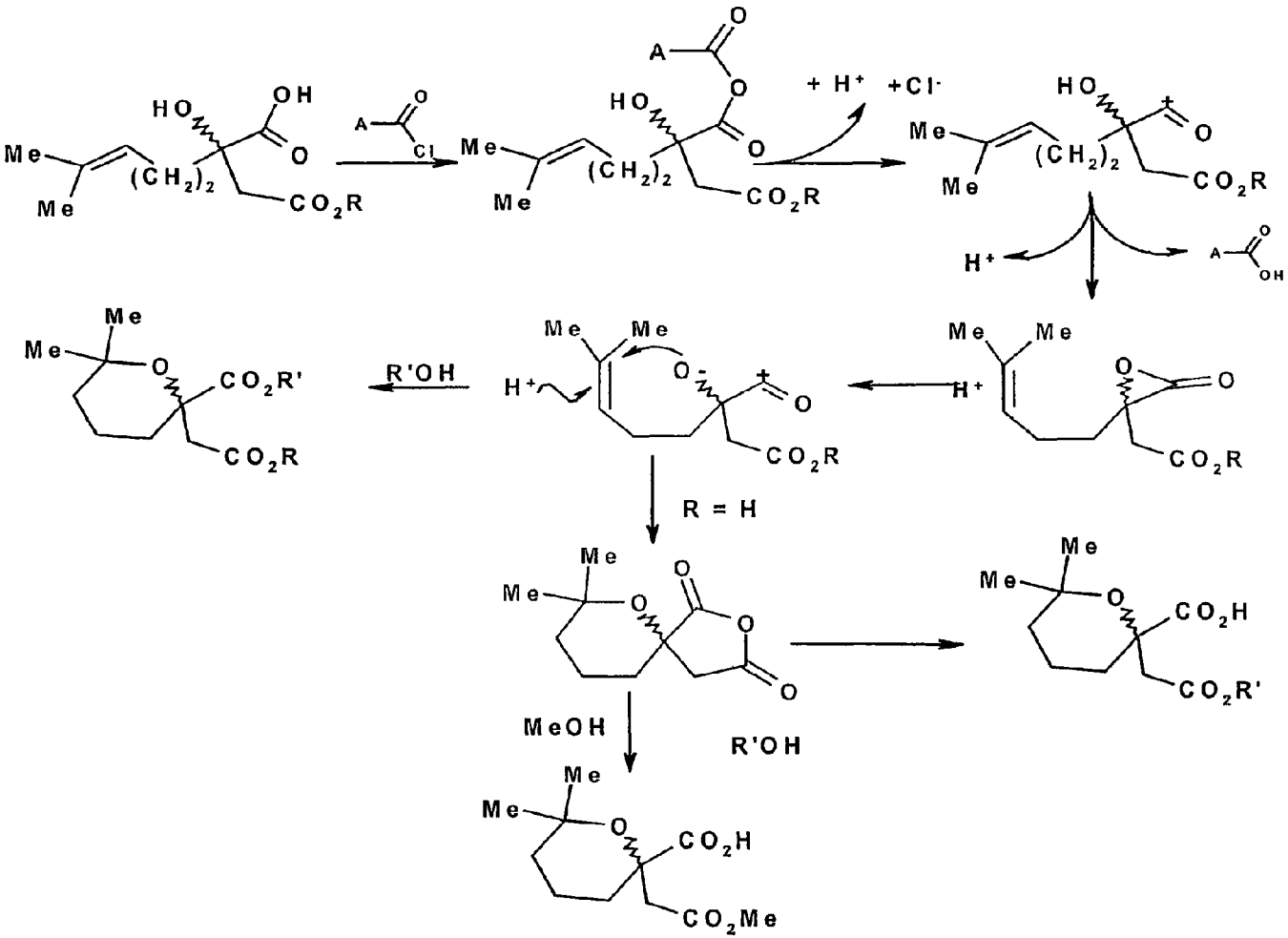

Alkaloids: natural substances present in the vegetal kingdom allowing at least a cyclic or acyclic basic nitrogen (allowed extensions: animal kingdom, primary amine; refused extensions: amidic nitrogen, because non basic, ex: taxanes) and showing frequently pronounced pharmacological properties.

Basic or free Alkaloid: alkaloid showing a tertiary amine in a non-ionized form generally existing at alkaline pH and soluble in aprotic organic solvents.

Salt of alkaloid or just <<salt>>: ionized form of alkaloid with amine function showing a positive formal charge and a negative counter-ion, actually more soluble in water and protic solvents and less soluble in aprotic solvents.

Cephalotaxanes 1 (see table p. 134): this generic term indicates the basic framework, showing diverse oxygenated substitutes (aliphatic or aromatic ether, free or esterified alcohol, enol and/or free or substituted phenol, bridged ether, more generally all substitute usually founded at natural state for this kind of compounds). Cephalotaxanes are particular alkaloids today only extracted from the Cephalotaxaceae family which exhibiting the structural formula 1 (Scheme 1). Several substituants may be encountered on this core structure: hydroxyl, ether, acyloxy etc. The eventual presence of some additional double bound or intramolecular bridge achieve to definite cephalotaxanes. Cephalotaxines 2 and harringtonines 3, are examples of cephalotaxanes. Several dozen of cephalotaxanes have been isolated from various Cephalotaxus species.

Cephalotaxines 2: this generic term indicates cephalotaxanes possibly showing at least one of the substitutes described above, a sidechain excepted. Cephalotaxines 2 (Scheme 1) are cephalotaxanes without acyloxy side-chain. Cephalotaxine 2a and drupacine 2b are example of cephalotaxines.

Cephalotaxine 2: a cephalotaxine in majority present in the genus Cephalotaxus

Cephalotaxoids: this generic term indicates a non-natural cephalotaxine.

Harringtonines: this generic term indicates cephalotaxane showing at least an alcohol group, a phenol or an enol, esterified by a sidechain and possibly by one of the substitutes described above. Harringtonines 3 (Scheme 1) are particular cephalotaxanes formed by attachment of a branched hydroxyacyloxy side-chain at the 3-position of various cephalotaxines moieties. Harringtonines are natural esters of cephalotaxines exhibiting generally a strong cytotoxic activity. However the lost only one atom of this minimal structure lead to a dramatic lost of activity (see below). Some example of harringtonines are harringtonine 3a, homoharringtonine 3b, drupangtonine 3c, anhydroharringtonine 3d and neoharringtonine 3e.

Harringtonine (the): one of the main alkaloids bearing a sidechain in position 3.

Harringtoids: this generic term indicates a non-natural harringtonine, where sidechain is an ester radical showing at least 3 carbon atoms.

Sidechain of the harringtoids: this generic term indicates an ester formed between one of the hydroxyl group and a carboxylic acid showing at least 3 carbon atoms allowing usually a tertiary alcohol [tertiaire] in [□] *the* α (*alpha*) position and an [hydrophobe substitute] *hydrophobic substituent* in [□] *the* ω position [relatively] *relative* to the carboxyl group.

Adaptation of the additive et subtractive empirical nomenclature suitable for céphalotaxanes.

Prefixes of common nomenclature are usually used in the literature to indicate structural variations of the sidechain of harringtonines (see Examples in the table p. 134). The sidechain of reference is this of harringtonine showed in formula 3b, n=2, R=H, $R^7$=H, $R^6$=2-hydroxyisopropyl.

Homo: 1 extra carbon.

Bishomo: 2 extra carbons.

Nor: a sidechain with 1 carbon less.

Iso: a sidechain with methylene bearing an hydroxyl group at the place of juxtaterminal carbon.

Deoxy: the hydroxyl group of juxtaterminal carbon is replaced par hydrogen.

Anhydro: the two tertiary hydroxyl groups lose a molecule of water to give the corresponding saturated oxygenated heterocycle.

neo: $R^6$ is a phenyl group at the place of 2-hydroxyisopropyl.

HPLC: High-Performance Liquid Chromatography.

NMR: Nuclear Magnetic Resonance.

DETAILED DESCRIPTION

The present invention thus has the advantage of obtaining enantiomerically pure harringtonines even from racemic cephalotaxine, since:

1st) the asymmetric centre on the side chain is created prior to the esterification step, i.e. the side chain precursor can be obtained in enantiomerically pure form prior to being attached, 2nd) the diastereoisomers obtained in the case of a racemic cephalotaxine can be separated by chromatography.

The present invention consists in:

esterifying the hindered free alcohol of a cephalotaxine or alternatively the corresponding metal alkoxide, using a chain in the form of a suitably substituted tertiary carboxylic oxacycloalkane acid which is totally preformed both in terms of the skeleton and in terms of the functionalization, in order to prepare anhydro-homo-harringtonic acids by semi-synthesis.

opening the cyclic side chains thus formed in order to obtain the corresponding diols, i.e. the harringtonines (defined above).

describing a new preparation for all of the diastereoisomers of the dihydroxylated side chains of the harringtonines in a dehydrated cyclic form (anhydroharringtonic acids) or in which the two hydroxyl groups are protected together by difunctional protecting groups forming a ring.

resolving all of the harringtonic and anhydroharringtonic acids, in order to couple them separately with the cephalotaxines.

One part of the present invention thus consists in synthesizing, in particular, anhydroharringtonine, harringtonine, anhydro-homo-harringtonine and homo-harringtonine.

The present invention also relates to esterifying cephalotaxines or metal alkoxides thereof with N-alkyl- and N-carbamoyl-2-alkylisoserine.

The hydroxyl of a cephalotaxane whose skeleton corresponds to the general formula 1 or, more particularly, a secondary alcohol located in position 3 of a cephalotaxine or metal alkoxides thereof, corresponding respectively to the general formulae CTX—O—H and CTX—O-M, M being a metal and CTX—the cephalotaxyl radical defined above, are esterified with the tertiary carboxylic acid function of a substituted cycloether corresponding to the general formula of the type 3k, or alternatively, preferably, with one of its activated forms, isolated or formed in situ, corresponding to the general formula of the type 3l to give 4c, according to the reaction below:

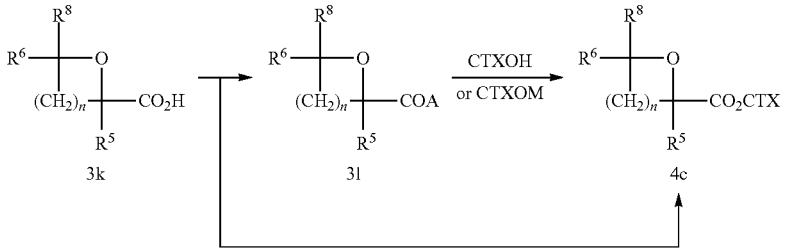

Following observations and comparative studies carried out in the taxane series, it was found that, despite a steric bulk which is still greater than that for the hydroxyl of the cephalotaxines, the hydroxyl located at position 13 on the taxane skeleton made it possible to receive acylation with a relatively bulky chain such as, for example, an N-benzoylphenylisoserine protected in position 2' (although the attempts to acylate baccatin protected with a chain bearing an (hydroxyl group protected with a benzoyl group all failed).

An experimental study of acylation with a very bulky chain, such as pivalic acid, demonstrated the impossibility of acylating the hydroxyl located at position 13 of a baccatin protected by the dialkyl carbodiimide method, whereas the same reaction performed on cephalotaxine showed easy coupling of the pivaloyl chain.

It has also been demonstrated, again in the taxane series, that the improvement in the dynamic compactness of the alkanoyl or aralkanoyl chain by a bifunctional cyclic protection greatly facilitated the coupling. Thus, for example, French patent applications [J. P. Robin et al., FR 95/12739 and FR 95/15557) indicate that the suitably protected, linear N-benzoylphenylisoserines react in several hours at 80° C. with formation of epimerization products, the oxazoline or oxazolidine cyclic precursors reacted in less than one hour at 25° C.

The use of the same conditions as above with a chain which has undergone a prior dehydrating cyclization, allowed us to acylate the cephalotaxine or its alkoxides in a few hours at room temperature.

The ease of this acylation was all the more surprising since many authors have designed syntheses which have the drawbacks mentioned above, on the basis of the observation of an impossibility of acylating, explained by the steric hindrance at the two sites: the hydroxyl of the cephalotaxine and the tertiary carboxyl of the side chain precursor [Mikolajczack et al., Tetrahedron, 1995 (1972)).

According to a preferred embodiment or process according to the invention, the hydroxyl function of a cephalotaxane is esterified with a 2-carboxyl-2-alkyl-1-oxacycloalkane derivative.

$R^5$, $R^6$ and $R^8$ are, independently of each other, a hydrogen, a linear or branched and/or cyclic, saturated, unsaturated or aromatic, hydrocarbon-based radical, in particular an alkyl, an alkenyl, an alkynyl, a cycloalkyl, a cycloalkenyl, an aryl, a heterocycloalkyl, the said hydrocarbon-based radical bearing or not bearing (a) heteroatom(s), it being possible for $R^5$ and $R^8$ to be linked together to form a ring an oxygenated ether bearing one of the above radicals.

n is between 0 and 8.

A is a leaving group capable of leaving behind a carbocation, 3l can thus be, in particular: an acid halide, an anhydride, a mixed anhydride or a cyclic anhydride (when $R^5$=—$CH_2CO$—).

The free acid of the type 3k or any activated form of the acids of the type 3l can be used to esterify the cephalotaxanes corresponding to the general formula 1 or, for example, the cephalotaxines of the type CTX—OH. Alternatively, the anhydride of 3l can be prepared separately and isolated, and then placed in contact with the alcohol. This is likewise the case for the cyclic anhydrides of the type 3p 3p

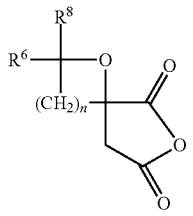

in which n, $R^6$ and $R^8$ have the same meaning as above, and which can be readily prepared from the corresponding diacids in order once again to give 3k by esterification of methanol or alternatively to become attached as above to the alcohol function of a cephalotaxine of the type 2 with, however, a poorer yield than that above, the primary acid function then being methylated conventionally using methanol in the presence of a protonic acid or a Lewis acid, or alternatively using the boron trifluoride etherate/methanol complex or diazomethane.

Although less effective and more laborious, the method using the acid chloride 3k gave the desired ester 4c.

All the reagents of the type 3k, 3l and 2, as well as the resulting esters of the type 4c, can be used alone in enantiomerically pure form, or in the form of a racemic mixture or in the form of diastereoisomeric mixtures. The intermediates can, in certain cases, not be isolated or formed in situ fleetingly.

The reaction can take place at between 0° C. and 140° C., with or without an organic solvent, it being possible for these solvents to be alone or as a mixture.

The esterification of the hydroxyl of cephalotaxane with a 2-carboxyl-2-alkyl-1-oxacycloalkane derivative can be carried out either by acyl transfer to the alcohol or by the carbodiimide method.

The esterification reaction by acyl transfer to the alcohol is advantageously carried out according to six specific modes:

(a) esterification of the free acid with the alcohol in acid catalysis, (b) esterification by acyl transfer via anhydrides or halides, (c) esterification by acyl transfer using activated esters, (d) esterification with scandium triflate, (e) esterification with boron trifluoride etherate, (f) esterification by the thioester method.

The esterification (a) takes place by placing the acid of the type 3k and the alcohol of the type 2 in contact in solution in a co-solvent and in the presence of an acid catalyst. The displacement of the equilibrium can be promoted by adding a dehydrating agent or by azeotropic entrainment or by partition between two immiscible solvents, one of which is miscible with the ester formed and the other with water. These various methods can be combined.

The acid catalyst can be a protonic acid such as, for example, sulphuric acid, hydrochloric acid, boric acid, preferably para-toluenesulphonic acid, or a Lewis acid which may or may not be supported on a polymer, such as, for example, aluminium chloride, chlorotrimethylsilane or, preferably, boron trifluoride etherate. Advantageously, an ion-exchange resin or bisulphate on graphite can also be used, for example.

The dehydrating agent can be, for example, a dehydrating agent consisting of an inorganic salt which is low in water and inert with respect to the reaction, such as magnesium sulphate, sodium sulphate, calcium chloride or, preferably, a molecular sieve.

The esterification (a) uses the same reaction conditions as above. However, in order to result in the formation of the acylium ion characteristic of this method, the ordinary acid catalysts are replaced, for example, with anhydrous sulphuric acid or superacids such as, for example, hydrofluoric acid and its derivatives or antimony pentafluoride.

The esterification (b) consists in using the same physical operating conditions as above, but using 3l, in which A represents a halogen (acid halide), another alkanoyl molecule which is identical (anhydride) or different (mixed anhydride), such as, for example, trifluoroacetyl, 2,4,6-trichlorobenzoyl, formyl, methoxyformyl, sulphonates, phosphates and chlorophosphate.

In a variant of the above method, and in the specific case in which $R^5$=$CH_2CO_2H$, a cyclic anhydride of the type 3p can be used 3p

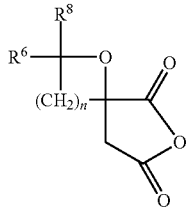

in which n, $R^6$ and $R^8$ have the same meaning as above, which can be prepared very simply by treating the corresponding diacid with acetic anhydride, for example under the general operating conditions for the preparation of the mixed anhydrides described below.

The catalysis can be acidic, as indicated in the above method, or, preferably, alkaline, for example a tertiary base such as pyridine and/or dimethylaminopyridine (DMAP), pyrrolidinopyridine (PPY), triethylamine, or a stronger base such as a hydride, for example calcium hydride. The solvent can preferably be an aprotic solvent, for example hexane, toluene, dichloromethane, tetrahydrofuran and/or pyridine.

The esterification (c) is a method similar to the esterification (b). These ester preparation methods can also be advantageously used and involve, for example, 1-acyloxy-1,2,3-triazole or formamidinium or silyl ester or 2-acyloxypyridinium intermediates.

The carbonyldiimidazole method, in which an N-acylimidazole intermediate is involved, can also be used.

The carbodiimide method uses a dehydrating coupling agent such as a carbodiimide, for example dicyclohexylcarbodiimide (DCC), 1,3-diisopropylcarbo-diimide (DIC) or 1-(3-dimethylaminopropyl)-3-ethyl-carbodiimide.

The reaction can be catalysed with a tertiary base such as, for example, pyridine and/or dimethylaminopyridine (DMAP), pyrrolidinopyridine (PPY), triethylamine, 4-morpholinopyridine or any other substituted base. N-Hydroxybenzotriazole (HOBt) or N-hydroxysuccinimide (HO-Su) can also be used, for example.

The molar ratio of 3l relative to 2 can be between 1/1 and 4/1.

The reaction can preferably be carried out under inert gas at a pressure close to atmospheric pressure, preferably at a temperature of between 0° C. and about 110° C.

The solvents preferably used are organic solvents such as, for example, toluene and/or dichloromethane and/or chloroform and/or tetrahydrofuran and/or pyridine and/or dimethylformamide.

The application of the methods described above, for the substituted carboxylic oxacycloalkanes, to the coupling of their synthetic precursors, the (linear) 1-hydroxy-1-methoxycarbonylmethylalkenecarboxylic acids, made it possible, against all expectation, to synthesize the esters of the type 4c in a single step from ethylenic tertiary (-hydroxy acids of the type 3f instead of the sequence 3f (3k (3l (4c.

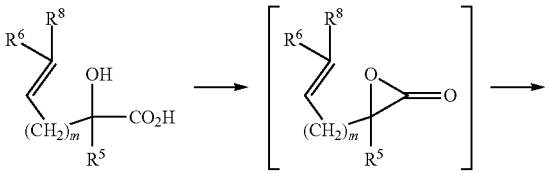

3f

-continued

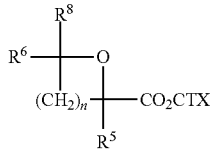

4c where m is between 0 and 3, in formula 4c, n, $R^5$, $R^6$, $R^8$ and CTX— have the same meaning as above.

Indeed, the ethylenic tertiary (-hydroxy acid 3f treated under conditions similar to those above directly gave the cyclic ester of cephalotaxines of the type 4c without isolation of an intermediate. In the case of the method involving a mixed anhydride 3l, the in situ formation of the corresponding (-lactone has been assumed on account of the presence of an infrared band at 1840 $cm^{-1}$.

These elements were confirmed by the formation and isolation of 3l, using 3f only under the activation conditions described above, i.e. to form the mixed anhydride, for example in the presence of 2,4,6-trichlorobenzoyl chloride, or alternatively, for example, in the so-called DCC method mentioned above.

The substituted carboxylic cycloethers of the type 3k, the substituted ethylenic tertiary (-hydroxy acids of the type 3f, their activated intermediates, and cyclic anhydrides of the type 3p, can be coupled with the cephalotaxines, either in the racemic series, or, more advantageously, in the optically active series.

In the case of coupling between one of the above types of acid, in the form of racemic mixtures, with a single enantiomer of a cephalotaxine, a relative stereo selectivity has been found due to the chirality and the major steric hindrance of the reaction site, in the sense that the ratio between each of the two diastereoisomers is generally other than 1.

The separation of the two diastereoisomers formed of the type 4c ($R^5$=$CH_2CO_2Me$), known as "anhydroharringtonine"

4c

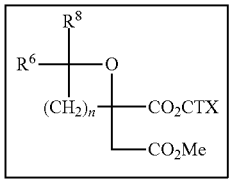

in which n, $R^6$, $R^8$ and CTX— have the same meaning as above, can be carried out by preparative chromatography either in a so-called normal phase, for example on native silica gel as stationary phase and a mixture of organic solvents as mobile phase, or, preferably, in a reverse phase, for example an inert silica grafted with apolar groups such as, for example, organosilyl, cyanoalkyl, phenylalkyl, preferably ocatadecylalkylsilane, chains and a mixture of aqueous solvents as mobile phase.

In the case of an enantiospecific coupling, no trace of epimerization is observed on any of the original parts, and the only diastereoisomer obtained can be crystallized. When this diastereoisomer is not crystalline, it is chromatographed by flash chromatography in order to remove the reagent residues, and is then precipitated by addition to a non-solvent, in order to be isolated in the form of amorphous powder.

The opening of the cephalotaxine carboxylate cycloethers of the type 4c to give the halo alcohol 4d is shown in the following scheme.

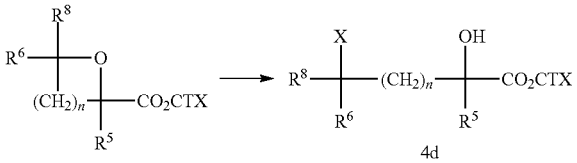

4c 4d

In these formulae n, $R^5$, $R^6$, $R^8$ and CTX— have the same meaning as above, X being a heteroatom such as a halogen.

The cyclic ethers of the type 4c can, in certain examples, have the particular feature of simultaneously containing a methyl enol ether, for example in position 2 of the cephalotaxines. Despite the usual inertia of true cyclic ethers (i.e. non-hemiacetal ethers), the placing in contact of a solution of 4c in an organic solvent, preferably a chlorinated solvent such as, for example, dichloromethane, dichloroethane or chloroform, under controlled conditions, i.e. in the presence, for example, of a dilute hydrohalic acid, preferably hydrobromic acid in acetic acid, at low temperature, or else in the presence of a halo-trialkylsilane or alternatively of a boron trihalide, for example boron tribromide at low temperature in an organic solvent, preferably a chlorinated solvent, such as, for example, dichloromethane, dichloroethane or chloroform, allowed it to be selectively opened to give a halo alcohol of the type 4d such that X=halogen, with a quantitative yield without any appreciable formation of the O-demethylation product, even in the case of cephalotaxines bearing enol ether(s) or other functions sensitive to ether-cleaving agents. In any case, in the event of an accidental demethylation, the enol can easily be selectively remethylated as described in the literature (for example by dissolution in methanol in the presence of para-toluenesulphonic acid).

The halo alcohols of the type 4d such that X=halogen are of great interest as substrates necessarily leading to heteroatomic analogues, on account of the very good reactivity towards the halogen substitution they bear.

Another variant consists in placing the product of type 4c in contact with an aqueous acid optionally in a miscible or immiscible co-solvent. The acid can be, for example, protonic, and in this case it is an organic or inorganic acid, preferably hydrochloric, tetrafluoroboric or formic acid. In this case, the diols of the type 4b can be isolated directly without passing through the halo alcohol stage described above.

The halo alcohols of the type 4d such that X halogen are hydrolysed according to the following scheme:

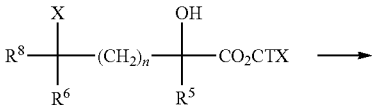

4d

-continued

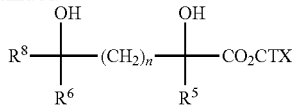

4b in which n, $R^6$, $R^8$, $R^5$, X and CTX— have the same meaning as above.

The halo alcohols of the type 4d are particularly suitable for controlled hydrolysis by placing in contact with an aqueous inorganic base such as, for example, dilute sodium hydroxide, sodium carbonate or, preferably, barium carbonate, at a temperature of between 0° C. and 30° C. with stirring, to give the diols of the type 4b.

One variant consists in carrying out the in situ hydrolysis of the intermediate halo alcohols of the type 4d at the end of the reaction, preferably carried out by treating the cyclic ether of the type 4c in dichloromethane in the presence of hydrobromic acid in acetic acid, and by directly adding the water or the hydrolysis solution to the reaction medium while cold and with vigorous stirring.

The process according to the invention is particularly suitable for the preparation of azaharringtonines, nitrogenous analogues of the harringtonines.

In order to demonstrate, for example, the flexibility of use of halo alcohols of the type 4d such that X=halogen as substrates, these materials were, for example, subjected to azidolysis by treatment using, for example, an alkaline azide in a solvent such as, for example, ethanol, methanol or dimethylformamide, which, by hydrogenolysis in solution in an organic solvent such as, for example, an alkanol or a lower ester, lead to the corresponding amino alcohol corresponding to the formula 4f (aminodeoxyharrington-ine). The amine can then be subjected to amidation under the Schotten-Baumann conditions, i.e. in aqueous media in the presence of an inorganic base as catalyst, to give an amido alcohol of the type 4$^e$

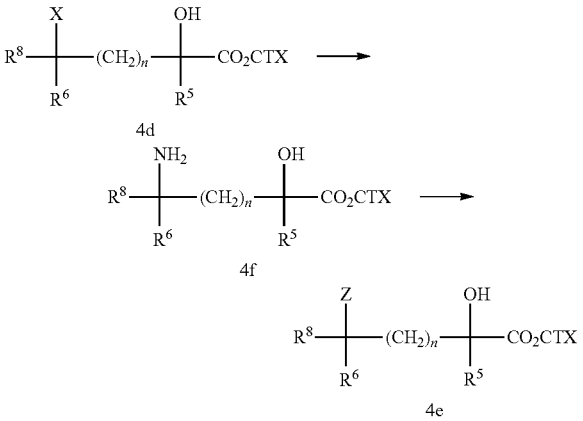

4d

4f

4e such that Z═NHCOR or NHCOAr, R and Ar being as defined above, more specifically alkyl or aryl groups, respectively, which may or may not be substituted. The amine 4f can also be sec-alkylated to give an alkylaminodeoxyharringtonine (Z═NHR or Z═NHAr or Z═$NR_2$ or Z═$NHAr_2$, it being possible for the two radicals R and Ar to be identical or independent), or acylated to give amides (Z═NHCOR or Z═NHCOAr) or carbamates (Z═NHCOOR) derived from the corresponding aminodeoxyharringtonine 4f, n, $R^5$, $R^6$, $R^8$, $R^9$, X and CTX— being defined as above.

Alternatively, the cyclic ethers of the type 4c can be suitable for the Ritter reaction in the presence of a nitrile (which can serve as solvent) at a low temperature of between −100° C. and +30° C. in the presence of an acid such as sulphuric acid, perchloric acid or, preferably, tetrafluoroboric acid, to give an acylaminodeoxyharringtonine (Z═NHCOR or Z═NHCOAr) derived from the corresponding aminodeoxyharringtonine 4f.

The extraction of the cephalotaxines of the type 2 is carried out according to the procedure indicated below.

The cephalotaxines of the type 2 can be prepared according to the methods described in the literature, either by synthesis or by extraction. In the latter case, since no method uses a direct placing in contact of the plant starting material with an aqueous acid, it has been found to be advantageous to describe this in the present invention. The fresh or dry plant starting material is placed in contact for 24 h with an acidified aqueous-organic mixture using a dilute inorganic acid or a weak organic acid, so as to bring the pH to between 1 and 4, preferably 3. The inorganic acid can be, for example, sulphuric acid or hydrochloric acid and the organic acid can be citric acid, lactic acid or tartaric acid, for example; the organic solvent can be, for example, a lower alkanol, a ketone, tetrahydrofuran or any other water-miscible solvent used in extraction by those skilled in the art. The water content is between 20 and 80%, preferably 50%. The solution obtained can be directly chromatographed or basified in order to be counter-extracted, since, in contrast with the methods described in the literature, it contains no chlorophyll and/or plant fat. The counter-extraction using a water-immiscible organic solvent such as a lower ester or, preferably, a lower halogenated hydrocarbon, more particularly dichloromethane, gives a mixture of total alkaloids isolated in the form of a white powder. Several methods for purifying Cephalotaxus alkaloids exist, but none, in particular in reverse phase, is specifically geared towards the purification of cephalotaxines and more particularly of the cephalotaxine of formula 2a.

The present process for purifying cephalotaxine, which forms an integral part of the novel process for the semi-synthesis of harringtonines, thus involves reverse-phase chromatography, which has never been used for this purpose.

This reverse-phase chromatography uses as stationary phase, for example, an inert silica grafted with apolar groups such as, for example, organosilyl, cyanoalkyl, phenylalkyl or, preferably, octadecylalkylsilane chains such as those encountered commercially, and a mixture of aqueous solvents as mobile phase, preferably water itself (without organic solvent); the pH is adjusted, i.e. to between 2 and 4, with an inorganic acid such as hydrochloric or phosphoric or sulphuric acid. It is also advantageous to add an additive such as, for example, aqueous ammonia or triethylamine. According to this process, which is economically very advantageous since it avoids the use of organic solvent and allows the reuse of the stationary phase for virtually hundreds of operations, the cephalotaxine is obtained in a quantitative recovery yield and with a purity of greater than 95%.

The above method makes it possible to obtain not only laevorotatory cephalotaxines naturally present in the plant material, but also racemic cephalotaxines also present in the natural state.

The metal alkoxides, corresponding to the general formula 1b (n=1 to 12) in which M is a metal, more particularly an alkali metal such as sodium, potassium or lithium, or a transition metal, for example zirconium, titanium or zinc, can be obtained by metallation of one or more of the hydroxyls in the mono- or polyhydroxycephalotaxanes corresponding to the general formula 1a (x=1 to 12) and in which M is more particularly an alkali metal or alkaline earth metal or any other metal which can conventionally give rise to the formation of an alkoxide.

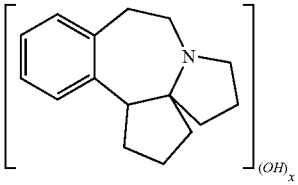

1a

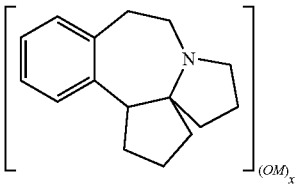

1b

This formation of alkoxide is of great value for acylating more readily in this form the hindered hydroxyls of the cephalotaxanes and most particularly for coupling this cephalotaxane with acylating precursors of the side chains, automatically leading to the harringtonines which are the subject of the present invention.

Several methods can be used to metallate the hydroxyl(s) of a cephalotaxane. For example, a metal hydride, an alkylmetal, an amide or, more generally, any agent capable of exchanging or of giving up a metal atom can be used.

The simple placing in contact of a hydroxylated cephalotaxane in organic solution, preferably under an inert gas, with a metal hydride such as, for example, potassium hydride, lithium hydride or, more particularly, sodium hydride, leads to a cephalotaxane metal alkoxide, which can, for example, serve as an in situ substrate in order to attach, for example, a suitably substituted alkyl, acyl or alkylsilyl group. The organic solvent can be a suitable aprotic solvent such as an ether, more particularly tetrahydrofuran, a liquid aromatic hydrocarbon, preferably toluene or, more generally, any organic solvent which is liquid under the temperature and pressure conditions used and which has no appreciable reactivity towards the reagent. The temperature of the reaction medium can be between −90° C. and +30° C.

The simple placing in contact of a hydroxylated cephalotaxane in organic solution, preferably under inert gas, with a metallated hydrocarbon such as, for example, a lithiated hydrocarbon, preferably butyllithium, leads to the same metal alkoxides as those above. The same solvents as above can be used, except that, since the reactivity of the metal hydrocarbons is generally greater than that of the metal hydrides, the temperature is between −100° C. and −20° C., preferably between −60° C. and −80° C.

The simple placing in contact of a hydroxylated cephalotaxane in organic solution, preferably under inert gas, with an amide, preferably an alkali metal amide, for example an alkali metal dialkylamide such as lithium dicyclohexylamide or lithium diisopropylamide or alkali metal (lithium, potassium or sodium) bis(trialkylsilyl)amide leads to the same metal alkoxides as above. The same solvents as above can be used.

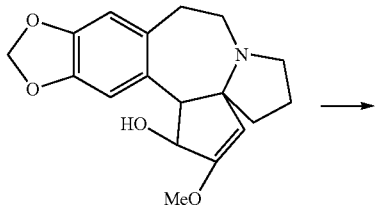

2a

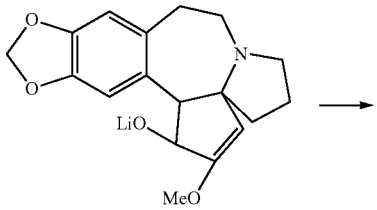

2h

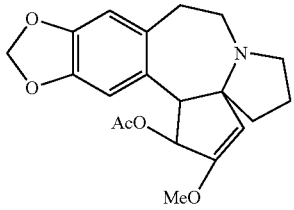

2b

As an example and without detracting from the generality of the present invention, the cephalotaxine 2a in solution stirred in tetrahydrofuran at −70° C., treated with one equivalent of butyllithium or lithium bis(trimethylsilyl)amide leads, in a few hours, to the lithium alkoxide 2h, which, when trapped in situ with acetic anhydride, gives the 3-O-acetylcephalotaxine 2b.

The preparation of the substituted racemic carboxylic cycloethers of the type 3k is detailed below.

According to a first variant, the preparation of these carboxylic cycloethers can be carried out by cyclization of the substituted ethylenic tertiary (-hydroxy acids of the type 3f according to the following scheme:

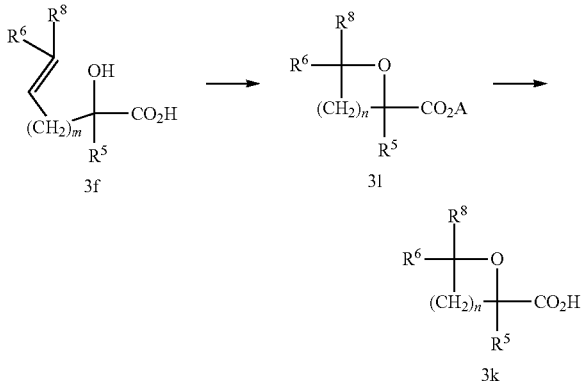

m, R, $R^5$, $R^6$, $R^8$ and A being defined as above.

The substituted carboxylic cycloethers of the type 3k such as, for example, A or B of formulae:

A

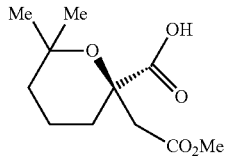

B

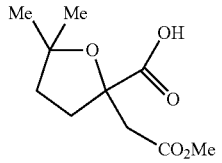

can be prepared from the substituted ethylenic tertiary (-hydroxy acids of the type 3f, by simple dissolution in an organic solvent in the presence of an acid.

According to a second variant, the preparation of these carboxylic cycloethers can be carried out by cyclization concomitant with the formation of the acylating species. As mentioned above, acids whose tertiary alcohol is free, such as 3f, cyclize spontaneously by the action of a dehydrating agent required for a certain technique for acylating a cephalotaxine alcohol mentioned above and then esterifying the latter to give 4c.

In the absence of an alcoholic substrate to receive it, the ethylenic tertiary alcohol of the 3f type leads, under anhydrous operating conditions, to the isolation of the acylating intermediate 3l, mentioned above, or, by hydrolysis, to the isolation of the acids of the type 3k.

In this case, the procedure used is strictly the one described for coupling involving the formation of an acylating species in situ but in the absence of a substrate of the cephalotaxine type.

According to a third variant, these substituted carboxylic cycloethers of the type 3k can be prepared by deprotecting the tertiary carboxyl of the suitably substituted precursor 3h,

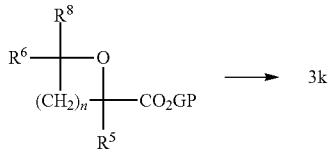

3h $R^5$, $R^8$, $R^6$ and n being defined as above and GP representing a protecting group for the acids, with, as a specific case, GP═R.

According to a fourth variant, in the specific case in which $R^5$═$CH_2CO_2R$, the suitably substituted carboxylic cycloethers of the type 3k such that $R^5$═$CH_2CO_2R$ below, 3k

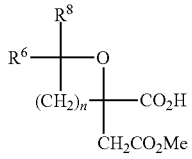

$R^8$, $R^6$ and n being defined as above,
can be prepared by total saponification of the corresponding diesters 3i such that $R^5$═$CH_2CO_2R$, followed by mild selective methylation of the intermediate diacid 3r such that $R^5$═$CH_2CO_2H$.

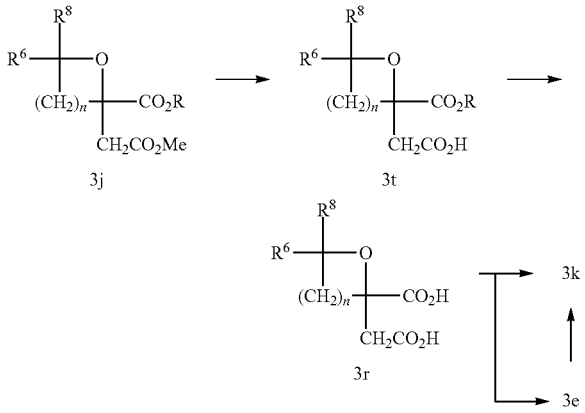

Incidentally, this process, carried out at room temperature and with rigorous monitoring of the reaction kinetics, leads to selective saponification of the above primary ester; it thus gives access to derivatives of the type 3t such that R=GP below, 3t

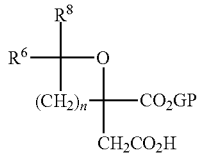

$R^8$, $R^6$, GP and n being defined as above,
which can be coupled with the cephalotaxines using the methods described above in order to ensure the absence of transesterification during the coupling of the tertiary acids which form the subject of the present invention.

According to a fifth variant, the preparation of these carboxylic cycloethers can be carried out by regioselective methanolysis of the corresponding cyclic anhydride.

As mentioned above, the diacid 3r leads, by self-dehydration, to the cyclic anhydride 3p, which is a good acylating agent for alcohols, such that by methanolysis 3k is also preferentially obtained such that $R^5$═$CH_2CO_2Me$, which constitutes an additional preparation method.

The preparation of the substituted ethylenic tertiary (-hydroxy acids of the type 3f is detailed below.

The substituted ethylenic tertiary (-hydroxy diacids which are the precursors of the monoacids of the type 3f can, like their cyclic analogues of the type 3k above, be obtained:

either by selective deprotection of their precursors of the type 3i

3i

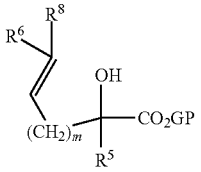

or, for example, in the case of the diacids of the type 3s such that $R^5{=}CH_2CO_2H$, 3s

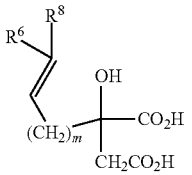

by selective methylation of the primary carboxyl in particular, by placing the reactants in prolonged contact in methanolic solution at room temperature or using the boron trifluoride/methanol complex.

The diacids of the type 3s such that $R^5{=}CH_2CO_2H$ can be obtained by saponification of the corresponding diesters of the type 3g such that $R^5{=}CH_2CO_2Me$ by placing the latter in contact with an excess of base in an aqueous or aqueous-alcoholic medium,

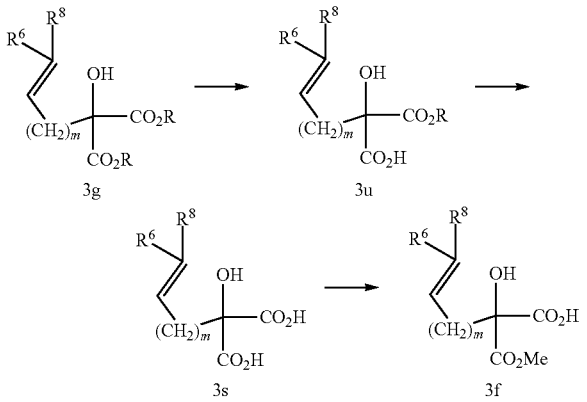

m, R, $R^8$ and $R^6$ being defined as above.

The alcohol can be a lower alcohol such as methanol, ethanol or, preferably, isopropanol, and the base can be, for example, an alkali metal or alkaline earth metal base or a rare earth metal hydroxide or aqueous ammonia. When the reaction takes place at a temperature of between 0° C. and 30° C. for 15 minutes to 1 hour, the regioselective saponification of the primary ester can be obtained without any resulting difficulty. By increasing the temperature to the boiling point of the solvent mixture and/or by lengthening the reaction time, the diacid is obtained in good yield and without formation of by-products.

The diacids of the type 3s such that $R^5{=}CH_2CO_2H$ can, on account of their crystallogenic properties, then generally be obtained in enantiomerically pure form by successive crystallizations of enantiomerically enriched mixtures until a constant optical rotation is obtained.

The diacids obtained above can then be converted into substituted ethylenic tertiary (-hydroxy acids of the type 3f such, that $R^5{=}CH_2CO_2Me$ by selective mono-esterification of their primary carboxyl, using methanol in the presence of a protonic acid or a Lewis acid or alternatively using the boron trifluoride etherate/methanol complex or diazomethane.

Incidentally, and as for the cyclic analogues of the type 3t such that $R^5{=}CH_2CO_2H$, above, this process carried out at room temperature and with rigorous monitoring of the reaction kinetics leads to selective saponification of the above primary ester; it thus gives access to derivatives of the type 3u such that $R^5{=}CH_2CO_2H$, which can be coupled to the cephalotaxines using the methods described above in order to ensure the absence of transesterification during the coupling of the tertiary acids which form the subject of the present invention.

The substituted ethylenic tertiary (-hydroxy esters of the type 3g can be prepared according to the scheme outlined below:

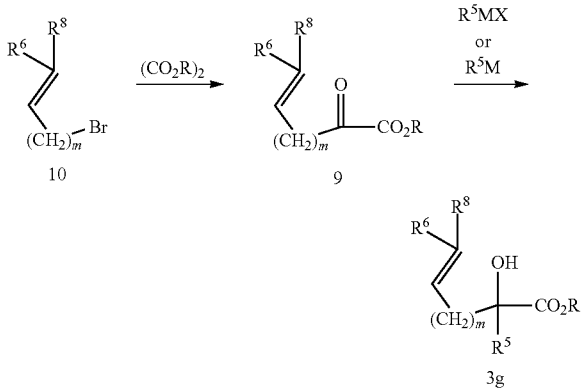

$R^6$, $R^8$, m and $R^5$ having the same meaning as above.

The ethylenic esters of the type 3g can be prepared according to the numerous methods described in the literature for similar cases such as, for example, (-hydroxyalkylation of the corresponding 1-alkyl- or 1-alkenyl-1-keto ester of the type 9.

As an example and without removing anything from the generality of the present invention, the (-hydroxyalkylation of the 1-alkenyl-1-keto ester of the type 9 with the lithium methoxycarbonylmethyl enolate ($R^5M{=}MeOCOCH_2Li$) or of the corresponding organozinc reagent (Réformatsky reaction, in which $R^5MX{=}MeOCOCH_2ZnBr$) leads to the diester a 3g such that $R^5{=}CH_2CO_2Me$.

The same reactions applied to a chiral ester (R=R*) lead to a mixture of separable diastereoisomers which, after deprotection of the tertiary acid function, each lead to the diastereoisomer of the pair.

Moreover, the (-hydroxyalkylation reaction of the 1-alkyl- or 1-alkenyl-1-keto ester of the type 9, conducted in the presence of a chiral inducing agent such as sparteine or quinine, can give a significant enantiomeric enrichment, which can be further enhanced by fractional crystallization.

The keto esters of the type 9 are themselves conventionally obtained by C-semi-acylation of the carbanion of the corresponding alkyl or alkenyl halides of the type 10 with a dialkyl oxalate.

One of the advantages over the prior art of the synthetic process which forms the subject of the present invention lies in the possibility of coupling an entirely preformed chain with the cephalotaxines. Thus, the preparation of the above anhydroharringtonic acids in enantiomerically pure form 3k is of considerable interest, since the post-coupling creation of the chiral centre in position 2' of the harringtonines during the attachment of the secondary chain as described in the prior art leads to an epimeric mixture, on the one hand, which is very difficult to separate, and, on the other hand, to a loss of about 50% of the very precious cephalotaxines (not recyclable in a process for manufacturing a medicinal substance using Good Manufacturing Practice).

Several methods have been used to achieve this aim. They all apply both to the cyclic monoacids of the type 3k or to their diacid precursors of the type 3r, and to their ethylenic linear precursors of the type 3f, it being possible for chiral chromatography methods also to be applied to the precursors which have no function capable of engaging a reversible chemical bond with a chiral species (in this instance free acid functions).

According to a first step of the process for the enantiospecific preparation of these acids, an epimeric mixture is formed by combination with a chiral alcohol or amine.

The reactions for esterifying a hindered secondary alcohol function of a cephalotaxine with oxacycloalkanecarboxylic acids of the type 3k above (including those formed in situ from ethylenic tertiary (-hydroxy acids of the type 3f) can also be applied to the esterification of another chiral alcohol in order to convert a racemic mixture, or one with partial enantiomeric enrichment of acids of the type 3k, into a diastereoisomeric mixture on which all of the non-chiral separation methods become applicable. The above methods are also applicable without modification to the amidation of chiral primary or secondary amines.

Thus, when the oxacycloalkanecarboxylic acids of the type 3k or their ethylenic linear precursors are reacted with a chiral alcohol, denoted by R*OH, or an amide R'*R*NH (it being possible for R'* to be replaced with a hydrogen), two chemical species are obtained in which the physicochemical properties are distinct (for example NMR, melting point, solubility, chromatographic properties, enzymatic or microbiological attack, etc.). The alcohol or the amide must preferably be hindered and bear their chiral centre at their site of binding with the tertiary carboxyl of the acid of the type 3k. The alcohol can be, for example, menthol, borneol, valinol or, preferably, quinine. The amine can be, for example, ephedrine; more generally, any commercial chiral alcohol or amide can be used.

the mixture of the two corresponding epimers 3v such that $R^5$=$CH_2CO_2Me$ and 3w such that $R^5$=$CH_2CO_2Me$:

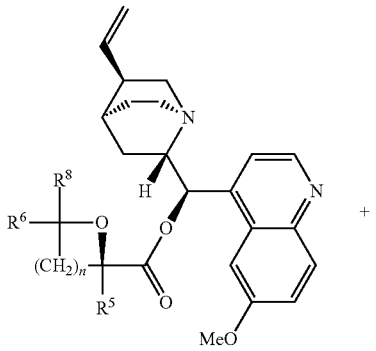

3v

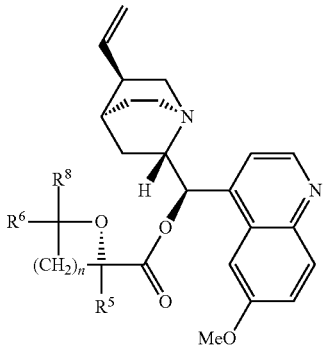

3w

The binary mixtures of epimers obtained by the combination with a chiral compound can be separated, for example, by fractional crystallization, by distillation, by counter-current liquid-liquid partition and, given the high added value of these intermediates, by any common preparative chromatography technique, for example normal phase chromatography, exclusion chromatography, preferably in reverse or normal grafted phase. Since these methods are synergistic, they can advantageously be combined in order to improve the diastereoisomeric purity.

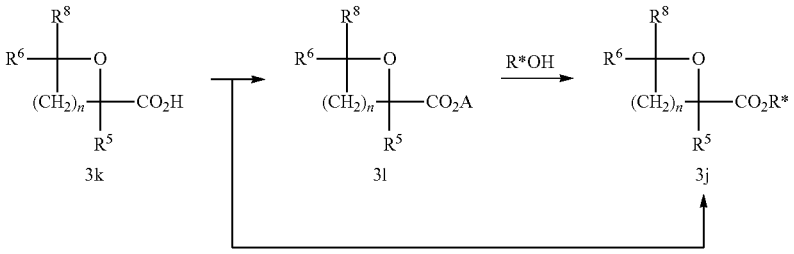

(R = R*)

n, $R^5$, $R^6$, $R^8$ and A having the same meaning as above, R* having the same meaning as R, but being chiral.

As an example, and without detracting at all from the generality of the present invention, (−)-quinine, which, like the cephalotaxines, is an alkaloid with a sterically hindered secondary alcohol function, reacts with the racemic mixture of the oxacycloalkanecarboxylic acids of the type 3k to give As an example and without detracting at all from the generality of the present invention, the mixture of the two epimers 3v (such that n=3; $R^6$=$R^8$=Me; $R^5$=$CH_2CO_2Me$) and (such that n=3; $R^6$=$R^8$=Me; $R^5$=$CH_2CO_2Me$), cited in the above example, can be separated without difficulty and in quantitative yield using a grafted phase of octadecylsilane type and a methanol/water mobile phase.

The regeneration of the oxacycloalkane-carboxylic acids of the type 3k in enantiomerically pure form can be carried out by total hydrolysis followed by selective remethylation of the primary carboxyl of the suitably selected diastereoisomer (see above sequence 3j (3k or, when it is an ester bond with an oxygen in the benzyl position (see for example quinine above), by simple hydrogenolysis. In the latter type of case, the drawback of the hydrogenolysis is largely offset by the economy of a step on an expensive product. As an example and without detracting at all from the generality of the present invention, (−)-quinine (2'R)-anhydroharringtonate 3v (such that n=3; $R^6$=$R^8$=Me; $R^5$=$CH_2CO_2$ a (2R)-anhydroharringtonic acid of the type 3k and dihydrodeoxyquinine which can thus not be recycled, but this is a minor drawback in view of the low cost of this alkaloid. Alternatively, the double saponification of 3v followed by selective remethylation gave a product which was entirely identical to the (2R)-anhydroharringtonic acid of the type 3k above.

The enantiomer of non-natural configuration (2S) can, after having undergone the same conversions as its (2R) enantiomer, be exploited, for example, for the purposes of structure-activity relationship studies.

According to a first step of the process for the enantiospecific preparation of these acids, the racemic mixtures are resolved by formation of salts with a chiral basic species.

The racemic mixtures of oxacycloalkane carboxylic acids of the type 3k (including those formed in situ from ethylenic tertiary (-hydroxy acids of the type 3f), can form a salt with a chiral amine by simple placing together in solution in an organic solvent. Although most of the methods described above for separating the esters and amides formed with 3k are applicable (for example chromatography), since the salts formed are generally highly crystallogenic, it is fractional crystallization which is preferably carried out to resolve the acids of the type 3k. The solvents used, alone or as a mixture, can preferably be polar organic solvents which may or may not be combined with water, such as, for example, ketones, alcohols and lower esters. The reaction to form the salt preferably takes place at a temperature of between 0 and 100° C. The recrystallization can be carried out by redissolving the salt in a mixture whose solvent power can be adjusted with precision by means of the use of the above combinations of solvents and by varying the temperature according to the standard techniques practised by those skilled in the art. When the diastereoisomeric enrichment is deemed to be sufficient, the salt is decomposed in the presence, for example, of a dilute aqueous acid such as hydrochloric acid or sulphuric acid. The extraction of the enantiomer of the regenerated acid can be carried out using a water-immiscible organic solvent such as, for example, a lower ester.

As an example and without detracting at all from the generality of the present invention, the racemic mixture of (2R or 2S)-anhydroharringtonic acids of the type 3k can be resolved, for example, by placing them in contact with (−)-ephedrine, followed by fractional recrystallization in an ethyl acetate/methanol mixture.

The 2R-anhydroharringtonic acid of the type 3k is then regenerated by placing the purified salt in contact with 2N hydrochloric acid and continuously extracting the acidic aqueous phase with ethyl acetate.

The oxacycloalkanecarboxylic acids of the type 3k described above can be subjected to preparative chiral chromatography.

The final products are purified by HPLC to give final products for pharmaceutical use.

Despite the performance levels of the modern methods of synthesis, of semi-synthesis and of isolation of natural substances, it is now established in the regulations issued by the health authorities in industrialized countries that impurity levels of greater than one per thousand (0.1% m/m) in a medicinal substance can be detrimental to the patient.

An identification followed by toxicology studies on any toxicologically unknown substance exceeding this threshold is, moreover, systematically demanded, in order to obtain pharmaceutical files for authorization to market the medicinal products.

The diastereoisomeric purity (with, as a specific case, the enantiomeric purity) can, moreover, lead to therapeutic aberrations; for example, it is well known that quinine (see above formula) is an antimalaria agent, whereas one of its diastereoisomers is a cardiac antifibrillant.

In the therapeutic field of the substances forming the subject of the present invention, it is common to encounter multiplications of from 10 to 100 of the active principle or of a side effect by minor changes (involuntary here) in the molecular structures.

Among the methods for achieving this level of purity, industrial high-resolution chromatography occupies a position of choice, its high cost being an argument which carries little weight compared with the very high added value of the sophisticated active principles, the robustness which it gives to the processes and the safety it offers to users.

As an example, and without detracting at all from the generality of the present invention, homo-harringtonine 4b such that n=3; $R^6$=$R^8$=Me; $R^5$=$CH_2CO_2Me$, CTX—=cephalotaxyl,

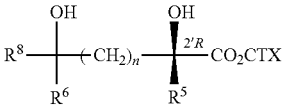

(2'R)-Homoharringtonine 4b

+

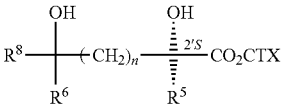

(2'S)-Epihomoharringtonine $R^6$, $R^8$, $R^5$, n and CTX— being defined as above, can be freed of its epimer at the same time as its other related impurities by preparative reverse-phase chromatography using a grafted reverse phase of octadecylsilane type as stationary phase and a suitably adjusted methanol/water mixture as mobile phase.

This process gives a product whose sum of related impurities is less than 0.5% and for which none of these impurities taken individually exceeds 0.1%.

The present invention concerns a process for the preparation of sidechain-bearing cephalotaxane of the following formula and/or a salt thereof

Ω-CO—O—CTX where

Ω ("omega") is a representative radical of the chain terminal moiety and —CO— is the carbonyl of the ester group bonded to cephalotaxane;

the Ω-CO— radical is corresponding:

either to the following substituted heterocycloalkane formula:

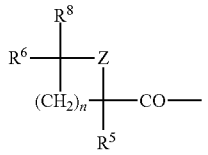

where n is included between 0 and 8;

Z is oxygen, nitrogen or sulfur heteroatom;

$R^5$, $R^6$ and $R^8$ are independently hydrogen;

hydrocarbon radical, saturated, insaturated or aromatic, linear or ramified and/or cyclic, especially alkyl, alkenyl, alkynyl, cycloalkyl, cycloalkenyl, aryl, heterocycloalkyl, of said radical including or not heteroatom(s); $R^6$ and $R^8$ may be included in a cycle;

oxygen ether bearing one of the former radicals;

or to the following linear alkene formula:

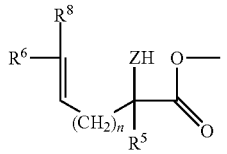

where m is included between 1 and 8, $R^5$, $R^6$ and $R^8$ are as defined above;

or to the following formula:

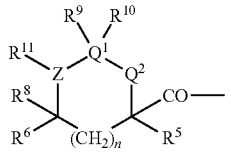

where n, $R^5$, $R^6$ and $R^8$ are as defined above;

Z and $Q^2$ are independently oxygen, nitrogen or sulfur heteroatom;

Q1 is carbon, silicium or phosphorus atom;

$R^9$ and $R^{10}$ are independently hydrogen, alkoxy, hydrocarbon radical, including or not heteroatom(s), saturated, unsaturated or aromatic, linear or ramified and/or cyclic, especially alkyl, alkenyl, alkynyl, cycloalkyl, cycloalkenyl, aryl, heterocycloalkyl;

$R^9$ and/or $R^{10}$ having the ability to be null or taken together to make an heteroatom and/or make a multiple bond with $Q^1$, $R^9$ and $R^{11}$ having the ability to be null to make a multiple bond between the two atoms of carbon bearing them; and $R^{11}$ is hydrogen, arylcarbonyl, alkoxycarbonyl, aryloxycarbonyl or alkylcarbonyl;

where

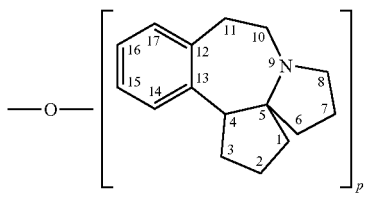

—O—CTX is cephalotaxine moiety of the following formula a salt thereof:

where p is equal to 1 or 2;

the two types of radicals -Ω and —CTX above-mentioned being bonded with an ester bond —CO—O— the said process bringing together:

either carboxylic acid with general formula Ω-CO—OH or a salt thereof;

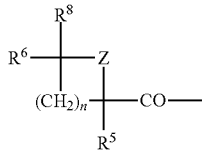

or an activated form of an acid with general formula Ω-CO-A or a salt thereof, with Ω-CO of the following formula:

where n, Z, $R^5$, $R^6$ and $R^8$ are as defined above;

where Ω-CO of the following formula:

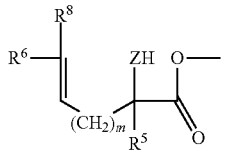

m is included between 1 and 8, Z, $R^5$, $R^6$ and $R^8$ are as defined above;

where Ω-CO of the following formula:

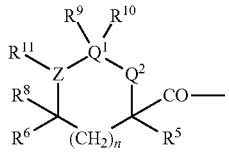

and where n, Z, $Q^1$, $Q^2$, $R^5$, $R^6$, $R^8$, $R^9$, $R^{10}$ and $R^{11}$ are as defined above A represents:

either cyclic anhydride of the following formula:

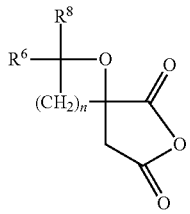

where n, $R^6$ and $R^8$ are as defined above;

the reaction has been completed by methylation of the primary carboxyl thus formed, with:

either a cephalotaxane or a salt thereof, bearing at least a free hydroxyl group, of the formula H—O—CTX, where CTX are as defined above;

or a metallic alcoxide of the formula M-O—CTX, where CTX are as defined above and M is a metal;

or an activated form of its hydroxyl group of the formula Y—O—CTX, where —O—CTX is as defined above and Y is, either a leaving group to allow a negative charge on oxygen atom by cleavage between Y— and —O—CTX, or to allow a carbocation by cleavage between Y—O— and —CTX;

with the possible presence of one or several reaction additives to form said sidechain-bearing cephalotaxane and/or a salt thereof.

Most preferably, Z is an oxygen atom and the cephalotaxane H—O—CTX is a cephalotaxine of the following formula, or a salt thereof:

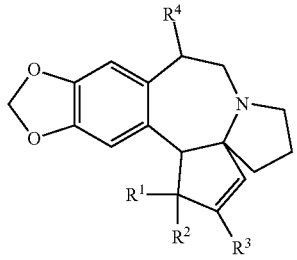

where $R^1$, $R^2$, $R^3$ and $R^4$ are independently hydrogen, hydroxyl group or alkoxide.

A cephalotaxane H—O—CTX, as defined above, is cephalotaxine, or a salt thereof, where $R^1$ is hydroxyl, $R^2$ is methoxyl, $R^3$ and $R^4$ are hydrogen.

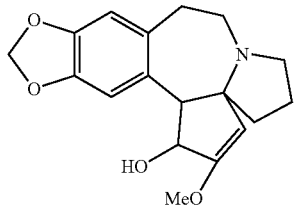

$R^5$ is preferably hydrogen or —$CH_2$—CO—O-Me.

The Ω-CO radical is preferably such as n=1 to 4, $R^6$ and $R^8$ are methyl.

The Ω-CO radical may be too such as n=1 or 2, $R^6$ is phenyl and $R^8$ is hydrogen.

When $R^5$ is —$CH_2$—CO—O-Me, $R^1$=OH, R2=OMe, $R^3$=$R^4$=H, the cephalotaxane is preferably such as n=0, Z is a nitrogen atom and $R^8$ is hydrogen.

A may be Ω-CO—CO where Ω is defined as above, or an halide.

A may also be a radical of compound Ω-CO-A having the ability to generate cleavage of the bond between carbonyl group and substituent A to provide Ω-$CO^+$ and $A^-$.

In addition, A is a radical selected from substituents:

Méthoxyformyloxy of formula MeOCOO—, trifluoroacétyloxy of formula $CF_3COO$—, alkylsulfonoxy of formula $RSO_3$—, phosphoxy of formula $(RO)_2PO$—, halophosphoxy of formula ROP(Cl)O—, trialkylsilyloxy of formula $R_3SiO$—, formulas wherein R is alkyl, diméthyl-formamidinium chloride of formula

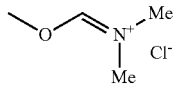

or acyloxy-pyridinium bromide of formula

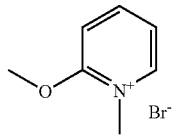

A may also be 2,4,6-trichlorobenzoyloxy or a radical corresponding to the following formula:

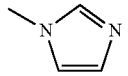

In the case where A is a carbonyl-diimidazole, where A is 2,4,6-trichlorobenzoyloxy, the reagent of formula Ω-CO-A is obtained by contacting an acid Ω-CO—OH, as defined above, with 2,4,6-trichlorobenzoyloxy carbonyl-diimidazole in presence of a strong base such as an alkoxide.

According carbodiimide method, the coupling additive is a substituted carbodiimide and/or a basic additive such as tertiary amine for example. For example, the substituted carbodiimide is selected from cyclohexylcarbodiimide (DCC), 1,3-diisopropylcarbodiimide (DIC) and chlorhydrate of 1-(3-dimethylaminopropyl)-3-ethyl-carbodiimide.

The cephalotaxine alcoxide, corresponding to the formula M-O—CTX where M and CTX are as defined above, may be obtained by contacting a cephalotaxine of formula H—O—CTX with metal himself, an amidure, a metallic hydride or an alkyl-metal.

M may be an alkaline metal such as lithium, potassium or sodium.

The aim of the present invention is also the preparation of new compounds such as:

the lithium alcoxide of cephalotaxine corresponding to the following formula:

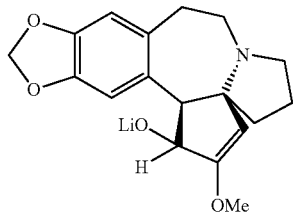

the sodium alcoxide of cephalotaxine corresponding to the following formula:

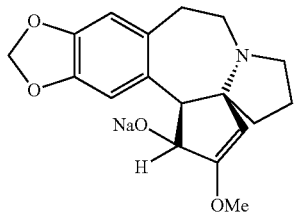

a sidechain-bearing cephalotaxane corresponding to the following formula and/or a salt thereof:

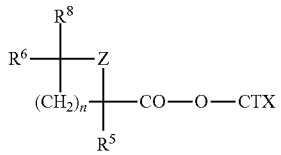

where n is included between 0 and 8;

Z is oxygen, nitrogen or sulfur heteroatom;

$R^5$, $R^6$ and $R^8$ are independently hydrogen;

hydrocarbon radical, saturated, insaturated or aromatic, linear or ramified and/or cyclic, especially alkyl, alkenyl, alkynyl, cycloalkyl, cycloalkenyl, aryl, heterocycloalkyl, of said radical including or not heteroatom(s);

oxygen ether bearing one of the former radicals;

CTX is as defined above;

except for compounds where Z is oxygen atom and,

1°) n=2 or 3, and simultaneously $R^6$=$R^8$=methyl and $R^5$=OMe or hydroxyl,

1°) n=2 and simultaneously $R^6$=$R^8$=methyl and $R^5$=OMe or hydroxyl;

3°) n=3 and simultaneously $R^6$ is hydroxyl, when $R^8$ is methyl and $R^5$ is —$CH_2CO_2CH_3$ radical.

a sidechain-bearing cephalotaxane corresponding to the following formula and/or a salt thereof:

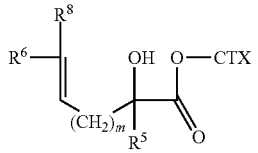

where m, $R^5$, $R^6$, $R^8$ and CTX are as defined above;

except compound where m=2, $R^5$=$CH_2CO_2CH_3$, $R^6$=$R^8$=methyl and CTX is as defined above.

$R^5$ is preferably the —$CH_2$—CO—O—$CH_3$ radical.

a sidechain-bearing cephalotaxane corresponding to the following formula and/or a salt thereof:

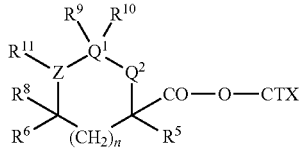

where n, Z, $Q^1$, $Q^2$, $R^5$, $R^6$, $R^8$, $R^9$, $R^{10}$, $R^{11}$ and CTX are as defined above.

Preferably, $Q^2$ is oxygen atom and/or Z is nitrogen atom and the cephalotaxane such as n=0.

a sidechain-bearing cephalotaxane corresponding to the following formula:

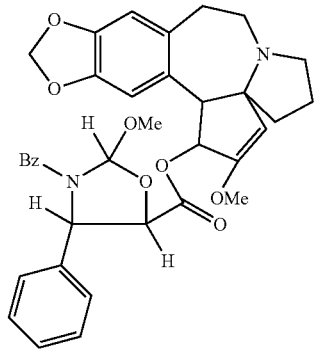

a sidechain-bearing cephalotaxane corresponding to the following formula:

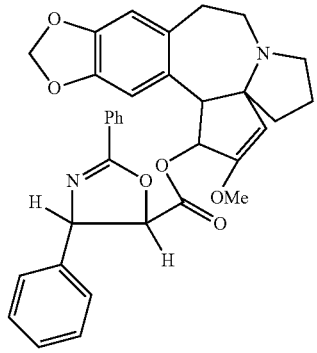

a sidechain-bearing cephalotaxane corresponding to the following formula:

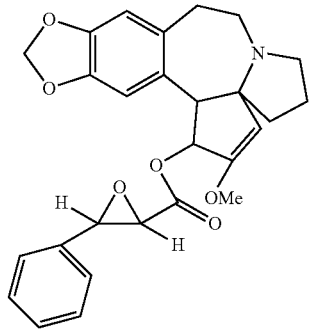

When the cyclic side-chain of sidechain-bearing cephalotaxane, and/or a salt thereof, presents the following formula:

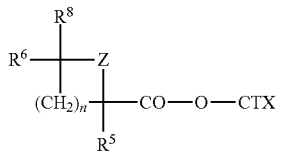

where n, $R^5$, $R^6$, $R^8$, CTX and Z are as defined above, the said chain is open with an agent and/or a protonic or not protonic electrophilic radical E in aqueous or not aqueous medium, to provide an intermediate compound of the following formula:

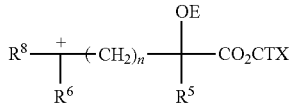

where n, CTX, $R^5$, $R^6$ and $R^8$ are as defined above, E is either hydrogen or the provisionally or definitively fixed eletrophilic radical;

the aforementioned intermediate compound may be attacked with an agent or a nucleophilic radical Z', deliberately added or possibly present in the medium, and when the cyclic side-chain of sidechain-bearing cephalotaxane, and/or a salt thereof, presents the following formula:

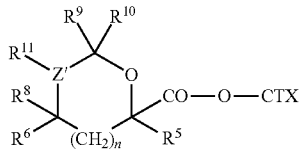

where n, $R^5$, $R^6$, $R^8$, $R^9$, $R^{10}$ and $R^{11}$ are as defined above, and Z' is an heteroatom;

the said chain is open by hydrolysis or carefully solvolysis with possibly presence of activation and/or opening additive.

In addition, to provide an open sidechain-bearing cephalotaxane of the following formula:

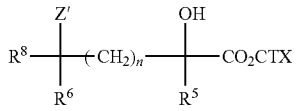

where n, CTX, $R^5$, $R^6$ and $R^8$ are as defined above;

Z' is:

either a halogen or an heteroatom bearing a hydrogen or a radical $R^{11}$ such as defined above;

or an hydrogen, hydrocarbon radical, the said radical bearing or not heteroatom(s), saturated, insaturated or aromatic, linear or ramified and/or cyclic, especially alkyl, alkenyl, alkynyl, cycloalkyl, cycloalkenyl, aryl, or heterocycloalkyl.

For example, cephalotaxine esters of the following formulas:

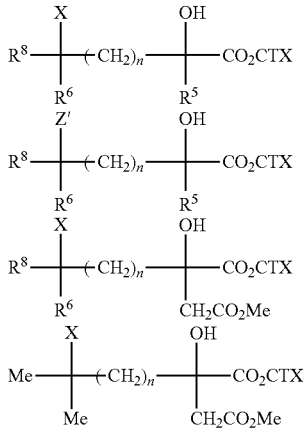

Where $R^5$, $R^6$, $R^8$, Z', X and CTX are as defined above;

bromodeoxyharrintonine (n=2) and bromodeoxyhomoharintonine (n=3)

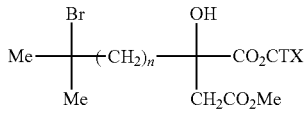

where CTX is as defined above;

aminodeoxyharrintonine (n=2) and aminodeoxyhomoharrintonine (n=3)

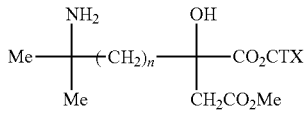

where CTX is as defined above;

In addition, when the cyclic side-chain of sidechain-bearing cephalotaxane, and/or a salt thereof, presents the following formula:

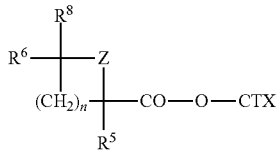

where n, $R^5$, $R^6$, $R^8$, CTX and Z are as defined above, the said chain is open by treatment with a solution of hydrobromic acid in acetic acid, in an halogenated solvent, preferably dichloromethane, followed by in situ hydrolysis to provide, without isolation of the intermediate, a sidechain-bearing cephalotaxane of the following formula:

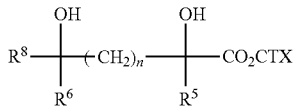

where n, CTX, $R^5$, $R^6$ et $R^8$ are defined above.

Acids corresponding to the following formula:

Ω-CO—OH where Ω radical is as defined according above;

the said formula equivalent to racemic mixture containing compounds of the formulas (+)-Ω-CO—OH and (−)-Ω-CO—OH such as (+)-Ω-CO—OH represents its dextrogyre enantiomer and (−)-Ω-CO—OH represent its levogyre enantiomer, were obtained a) by contacting of said racemic mixture or one of its activated form of the formula

Ω-CO-A which is as defined above;

the said racemic mixture or said activated form generating respectively:

either an anion corresponding to the formula $(\Omega\text{-CO—O})^-$;

or a cation corresponding to the formula $(\Omega\text{-CO})^+$;

with a pure enantiomeric form of chiral entity, said "resolution agent" symbolized by Δ*(delta stella), having the ability to form:

either a stable combination, by covalent bonding;

or an easily reversible labil combination, by hydrogen bonding or by hydrophobic interaction;

or intermediate lability bonding by electrostatic interaction;

to provide a diastereomeric mixture of Ω-CO—O-Δ* and de Ω-CO-Δ*;

b) then by physical separation of the mixture of two diastereomers or two complex compounds or more generally of two new entities physically and/or chemically different then obtained;

c) then by regeneration and finally separation of each one of enantiomers of the generic formula Ω*-CO—OH, where Ω* (<<oméga stella>>) represents the generic symbol of the same chiral radical in the either one or the other pure enantiomeric forms corresponding to the following formulas (+)-Ω-CO—OH and (−)-Ω-CO—OH which are as defined above.

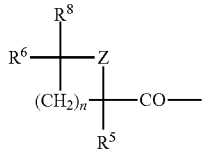

Preferably, Ω-CO— is:

either a radical corresponding to the following formula:

where n, Z, $R^6$, $R^8$, and $R^5$ are as defined above;

or a radical corresponding to the following formula:

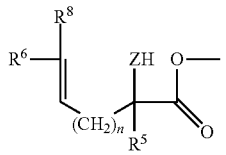

where m, Z, $R^6$, $R^8$, and $R^5$ are as defined above;

or a radical corresponding to the following formula:

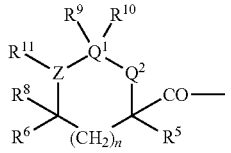

where n, $R^5$, $R^6$, $R^8$, Z, $Q^2$, $Q^1$, $R^9$, $R^{10}$ and $R^{11}$ are as defined above.

The stable combination may be represented by an ester of the following formula Ω-CO—O-Δ* such as Ω and Δ* are as defined above, the said stable combination is obtained by contacting acid with a chiral alcohol corresponding to the formula HO-Δ* such as Δ* is as defined above, according the process of invention.

The stable combination may be represented by an amide corresponding to the either one or the other formulas Ω-CO—NH-Δ* or Ω-CO—N-Δ* such as Ω and Δ* are as defined above, the said stable combination is obtained by contacting acid with primary or secondary chiral amine corresponding to formulas $H_2N$-Δ* or NN=Δ* such as Δ* is as defined above, according the process of the invention.

The stable combination may be represented by an thioester of the following formula Ω-CO—S-Δ* such as Ω and Δ* are as defined above, the said stable combination is obtained by contacting acid with a chiral thiol corresponding to the formula HS-Δ* such as Δ* is as defined above, according the process invention.

Finally, the ionic combination may be represented by a salt just prepared by contacting of acid with a chiral amine corresponding to the either one or the other of the three following formulas:

$\Omega\text{-CO—O}^-[\text{NH-}\Delta^*]^+$ $\Omega\text{-CO—O}^-[\text{NH}_2\text{-}\Delta^*]^+$ $\Omega\text{-CO—O}^-[\text{NH}_3\text{-}\Delta^*]^+$ where Ω and Δ*. are as defined above.

The bringing into play of a labil bonding based combination is achieved in the form of chromatography with the help of a chiral stationary phase.

The bringing into play of an interatomic or intermolecular labil bonding based combination, within crystalline lattice, is achieved in the form of fractionated crystallization initiated by a chiral precursor.

The chiral alcohol HO-Δ* is:

either (−)-quinine corresponding to the following formula:

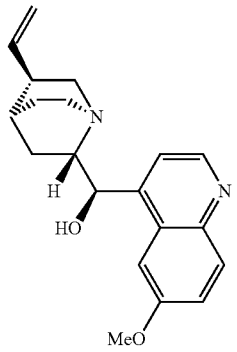

or (−)- or (+)-methyl mandelate corresponding to the following formulas:

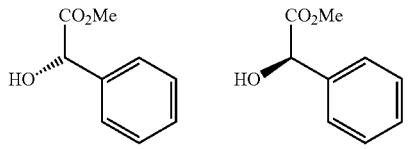

or (−)- or (+)-menthol corresponding to the following formulas:

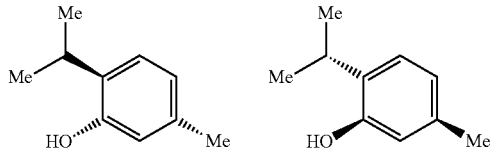

The chiral amine $H_2N$-Δ* is (−)- or (+)-ephedrine corresponding to the following formulas:

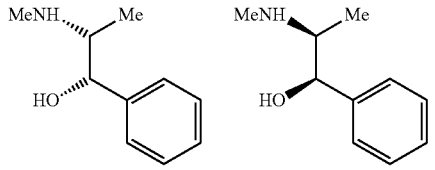

The present invention concerns the following new compounds:

the (−)-quinidyl (2'R)-(−)-anhydro-homoharringtonate and the (−)-quinidyl (2'S)-(−)-anhydro-homoharringtonate corresponding respectively to the two following formulas:

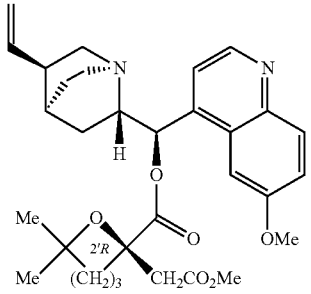

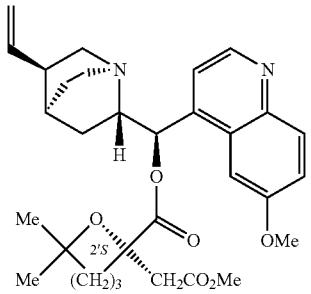

the (−)-menthyl (2'R)-(−)-anhydro-homoharringtonate and the (−)-menthyl (2'S)-(−)-anhydro-homoharringtonate corresponding respectively to the two following formulas:

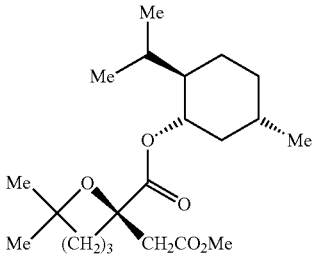

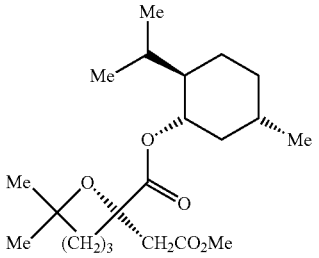

the (−)-methylmandelyl (2'R)-(−)-anhydro-homoharringtonate and the (−)-methylmandelyl (2'S)-(−)-anhydro-homoharringtonate corresponding respectively to the two following formulas:

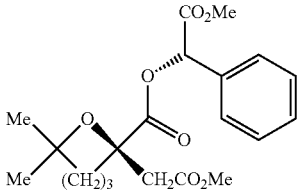

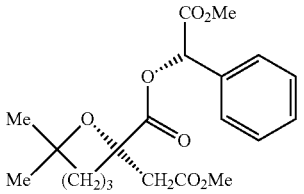

the (−)-ephedrinium (2'R)-(−)-anhydro-homoharringtonate and the (−)-ephedrinium (2'S)-(−)-anhydro-homoharringtonate corresponding respectively to the two following formulas:

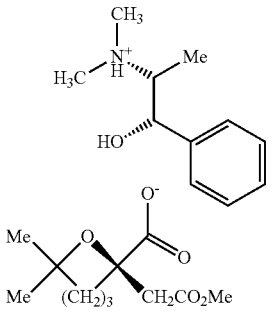

-continued

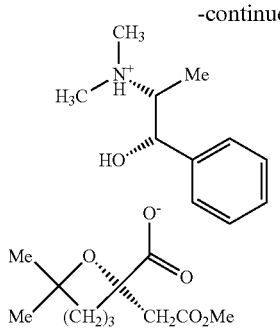

According the process of invention, when the carboxylic acid is the tertiary heterocycloalcane carboxylic acid corresponding to the following formula:

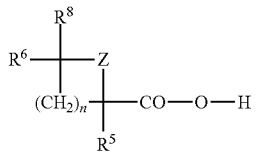

where n, Z, $R^5$, $R^6$ and $R^8$ are as defined above, the said acid is obtained by treatment in aprotic or protic solvant, eventually in the presence of cyclization additive and/or dehydrating agent, the said treatment eventually supported with physical carrying of the water formed.

or open tertiary ethylenic acid corresponding to the following formula:

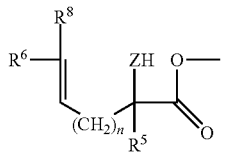

where m, Z, $R^5$, $R^6$ and $R^8$ are as defined above.

or open tertiary ethylenic acid corresponding to the following formula:

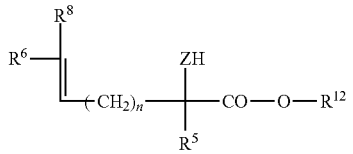

where m is included between 1 and 8, Z, $R^5$, $R^6$ and $R^8$ are as defined above, $R^{12}$ is not a CTX radical as defined above and represents $R^5$ and/or a protective group of acids and/or a chiral group;

then $R^{12}$ is removed later, either just by saponification, or by hydrogenolysis, or more generally by the method of the state of art to remove protective groups of acids.

In the absence of cyclization additive, the reaction of cyclization just take place by heating.

Preferably, the cyclization additive is a protic acid such as sulfonic or formic acid, or an aprotic acid, included in immobilized form.

In the step of preparation of the acid described above, Z is an oxygen atom.

The aim of the present invention is also the preparation of the following new compounds:

the tertiary heterocycloalcane carboxylic acid, included its salts and each one of its pure enantiomeric forms or in racemic mixture or in variable composition, corresponding to the following formula:

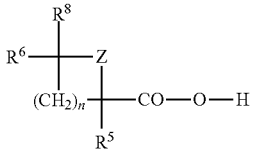

where n, Z, $R^5$, $R^6$ and $R^8$ are as defined above, and $R^5$ is not hydrogen;

except for compounds where Z is oxygen atom and,

1°) n=0 and $R^5$ is not —$CH_2CO_2H$ or —$CH_2CO_2CH_3$ radical;

2°) n=0 and $R^5$ is —$CH_2CO_2H$ or —$CH_2CO_2CH_3$ radical, and $R^6$=$R^8$=methyl or —$CH_2CO_2H$ or —$CH_2CO_2CH_3$ radical;

3[□]°) n=2 and simultaneously $R^6$=$R^8$=methyl, and $R^5$=OMe or hydroxyl;

4[□]°) n=2 and simultaneously $R^6$=$R^8$=methyl, and $R^5$ is —$CH_2CO_2H$ or —$CH_2CO_2CH_3$ radical; or methyl;

5°) n=3 and simultaneously $R^6$ is hydroxyl, and $R^8$ is methyl, and $R^5$ is —$CH_2CO_2CH_3$ radical;

6°) n=3 and simultaneously $R^6$=$R^8$=methyl and $R^5$=OH or methyl or ethyl.

the tertiary oxacycloalcane carboxylic acid, included its salts and each one of its pure enantiomeric forms or in racemic mixture or in variable composition, corresponding to the following formula:

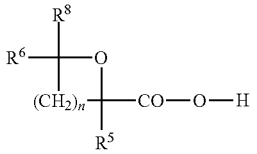

where n is included between 0 and 8, $R^5$, $R^6$ and $R^8$ are as defined above, but are not hydrogen simultaneously.

except for compounds corresponding to the exceptions 1 to 6 defined above.

the tertiary heterocycloalcane carboxylic acid, included its salts and each one of its pure enantiomeric forms or in racemic mixture or in variable composition, corresponding to the following formula:

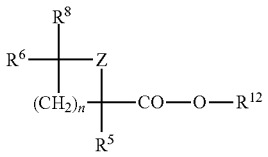

where n is included between 0 and 8, Z, $R^5$, $R^6$ and $R^8$ are as defined above, $R^5$ is not hydrogen, and $R^{12}$ is not a CTX radical defined above;

except for compounds where Z is oxygen atom and, corresponding to the exceptions 1 to 6 defined above.

the tertiary oxacycloalcane carboxylic hemiester, included its salts and each one of its pure enantiomeric forms or in racemic mixture or in variable composition, corresponding to the following formula:

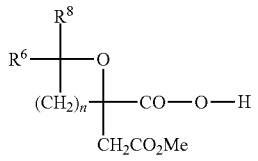

where n is included between 0 and 8, $R^6$ and $R^8$ are as defined above.

except for compounds corresponding to the exceptions 1 to 6 defined above.

the tertiary oxacycloalcane carboxylic hemiester, included its salts and each one of its pure enantiomeric forms or in racemic mixture or in variable composition, corresponding to the following formula:

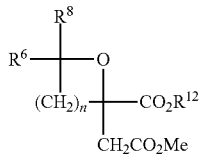

where n is included between 0 and 8, $R^6$ and $R^8$ are as defined above, $R^{12}$ is an hydrocarbon radical different from CTX as defined above.

except for compounds corresponding to the exceptions 1 to 6 defined above.

the tertiary oxacycloalcane carboxylic hemiester or anhydro-homoharringtonic acid, included its salts and each one of its pure enantiomeric forms or in racemic mixture or in variable composition, corresponding to the following formula:

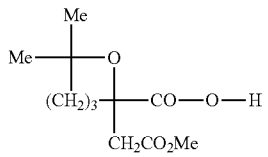

the tertiary oxacycloalcane carboxylic hemiester or anhydro-harringtonic acid, included its salts and each one of its pure enantiomeric forms or in racemic mixture or in variable composition, corresponding to the following formula:

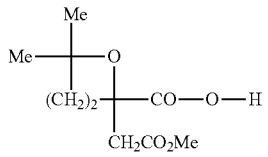

the tertiary oxacycloalcane carboxylic acid, included its salts and each one of its pure enantiomeric forms or in racemic mixture or in variable composition, corresponding to the following formula:

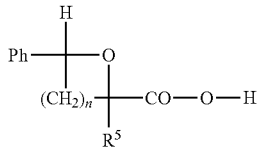

where n and $R^5$ are as defined above, except for compounds corresponding to the exceptions 1 to 6 defined above.

the tertiary oxacycloalcane carboxylic acid, included its salts and each one of its pure enantiomeric forms or in racemic mixture or in variable composition, corresponding to the following formula:

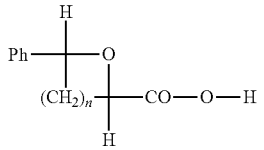

where n is included between 1 and 8.

the tertiary oxacycloalcane carboxylic acid, included its salts and each one of its pure enantiomeric forms or in racemic mixture or in variable composition, corresponding to the following formula:

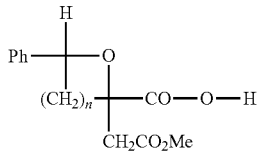

where n is included between 0 and 8.

the tertiary oxacycloalcane carboxylic acid or oxanhydroneoharringtonic acid, included its salts and each one of its pure enantiomeric forms or in racemic mixture or in variable composition, corresponding to the following formula:

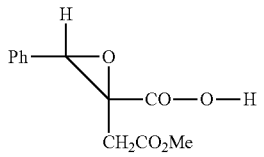

the tertiary oxacycloalcane carboxylic acid or oxanhydroneohomoharringtonic acid, included its salts and each one of its pure enantiomeric forms or in racemic mixture or in variable composition, corresponding to the following formula:

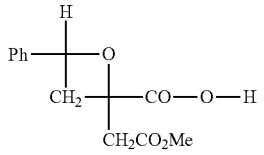

the tertiary oxacycloalcane carboxylic acid, included its salts and each one of its pure enantiomeric forms or in racemic mixture or in variable composition, corresponding to the following formula:

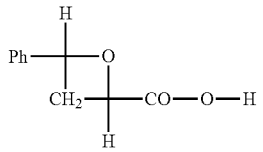

the tertiary alkene carboxylic acid, included its salts and each one of its pure enantiomeric forms or in racemic mixture or in variable composition, corresponding to the following formula:

where m is included between 1 and 8, $R^6$ and $R^8$ are as defined above, but are not hydrogen simultaneously, and $R^5$ is not hydrogen or heteroatom.

the tertiary alkene carboxylic acid, included its salts and each one of its pure enantiomeric

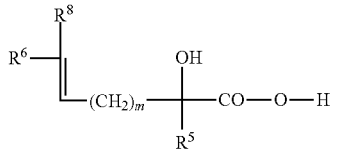

forms or in racemic mixture or in variable composition, corresponding to the following formula:

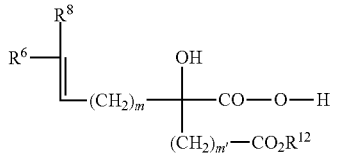

where m, $R^6$, $R^8$ and $R^{12}$ are as defined above, and m' is included between 1 and 8.

the tertiary alkene carboxylic acid, included its salts and each one of its pure enantiomeric forms or in racemic mixture or in variable composition, corresponding to the following formula:

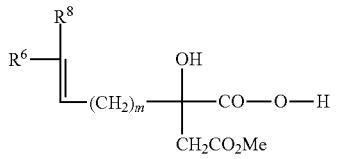

where m is included between 1 and 8, $R^6$ and $R^8$ are as defined above but are not hydrogen.

the tertiary alkene carboxylic acid, included its salts and each one of its pure enantiomeric forms or in racemic mixture or in variable composition, corresponding to the following formula:

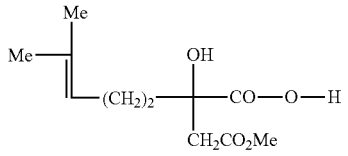

the tertiary alkene carboxylic acid, included its salts and each one of its pure enantiomeric forms or in racemic mixture or in variable composition, corresponding to the following formula:

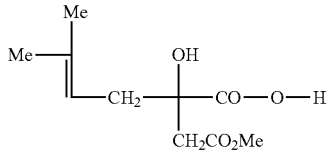

the tertiary alkene carboxylic acid, included its salts and each one of its pure enantiomeric forms or in racemic mixture or in variable composition, corresponding to the following formula:

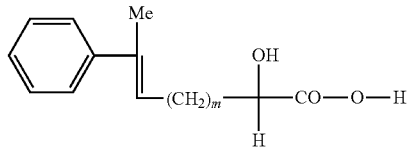

where m is included between 1 to 8, preferably m=1.

the anhydrides of acid of the general formula Ω-CO—O—CO-Ω where Ω is as defined above.

the mixed anhydrides of acid of the general formula Ω-CO-A where A is a radical selected from the following substituents:

méthoxyformyloxy of formula MeOCOO—, trifluoroacétyloxy of formula $CF_3COO$—, alkylsulfonoxy of formula $RSO_3$—, phosphoxy of formula $(RO)_2PO$—, halophosphoxy of formula ROP(Cl)O—, trialkylsilyloxy of formula $R_3SiO$—, formulas wherein R is alkyl.

diméthyl-formamidinium chloride of formula

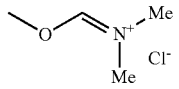

acyloxy-pyridinium bromide of formula

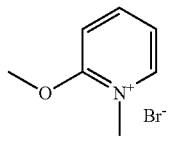

and 2,4,6-trichlorobenzoyloxy.

the mixed anhydride corresponding to the following formula:

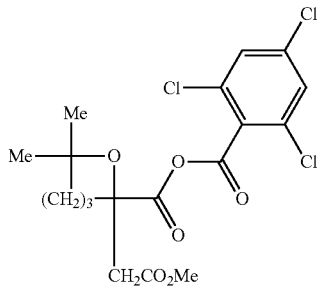

the acid chlorides defined above, corresponding to the general formula Ω-CO—X, where X is halogen.

the cyclic anhydrides corresponding to the following formula:

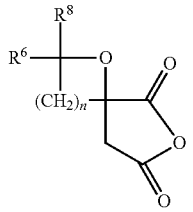

where n, $R^6$ and $R^8$ are as defined above.

the cyclic anhydride corresponding to the following formula:

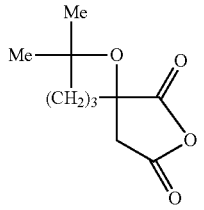

In the process according to the invention, the sidechain-bearing cephalotaxane was purified like a salt by chromatography using a hydrophobic reversed-phase like stationary phase, and a mobile phase without organic solvent like a solution adjusted to a pH 2 to 4.5 with a buffer prepared with an acid and an alkaline or ammonium salt and one or several additive like attenuator of silanol effect, the said cephalotaxine salt was generated from mineral acid under the form of chlorohydrate, sulfate, phosphate, nitrate, perchlorate, or from organic acid under the form of tartrate, malate, citrate or lactate.

In the process according to the invention, the sidechain-bearing cephalotaxane was purified by a step of chromatographic purification of a natural or semi-synthetic or synthetic homoharringtonine [as a] *for* pharmaceutical use, corresponding to the following formula *and having the chemical name, cephalotaxine, 4-methyl (2R)-2-hydroxy-2-(4-hydroxy-4-methylpentyl)butanedioate (ester)*:

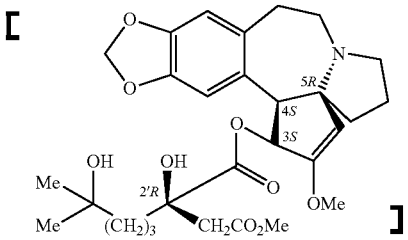

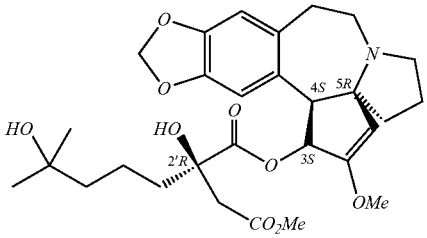

to remove the undesired related impurity named [2'-épi-homoharringtonine] *2'-epi-homoharringtonine* resulting:

a) either from a semi-synthetic process [with introduction of] *in the course of which* a synthetic homoharringtonic acid of inadequate enantiomeric purity *was introduced*, the generated impurity [showing] *having* the absolute configuration corresponding to the following formula:

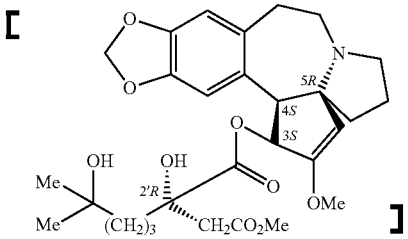

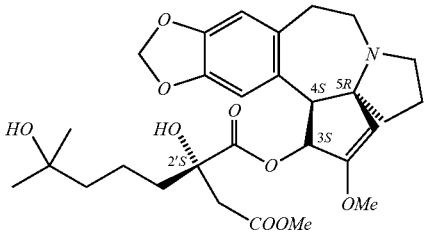

b) *or from a synthetic or semi-synthetic process,* or from the biosynthetic process in the plant, [where] *in the course of which* a cephalotaxine [with] *of* inadequate enantiomeric purity was introduced, or in the form of [artefact] *an artifact* by partial racemization of the cephalotaxine moiety, the generated impurity [showing] *having* strictly identical chromatographic properties [with] *in* a non-chiral system, [with] *and having* an absolute configuration opposite to the one above (enantiomer) [and] corresponding to the following formula:

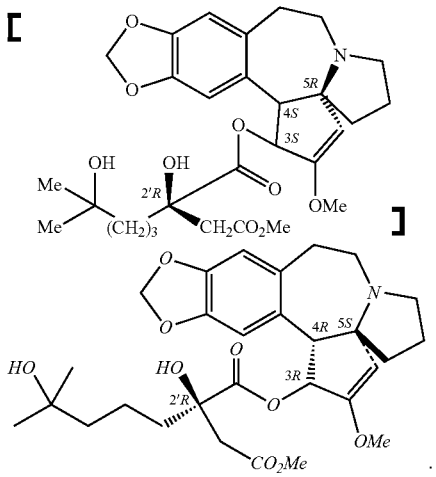

especially making use of one of the following chromatographic systems:

A) Stationary phase: alkyl- or phenyl- or alkylphenyl- or phenylalkyl-silane, preferably n-octadecylsilane, B) Mobile phase: water-tetrahydrofurane, water-methanol, water-acetonitrile or buffer pH 2 to 6.5 in replacement of water, or all other mobile phase with equivalent selectivity, This process of purification and chromatographic control of a natural or semi-synthetic or synthetic homoharringtonine, [allows to offset the double] *makes it possible to overcome the two fold* insufficiency of enantiomeric purity of the semi-precursors *thereof, i.e.*, both on the sidechain precursor ([said] *referred to as* homoharringtonic acid) and *the* cephalotaxine, *whether or not* the two [said-precursors] *semi-precursors* are each independently generated by total synthesis or semi-synthetic process or natural process [within of] *in* the plant (biosynthesis), [in fact the withdrawal] *i.e. the removal* of the non natural enantiomer of homoharringtonine [showing an] *having the* opposite absolute configuration, by using a chiral stationary phase [with] *on a* preparative scale.

The table [p. 156] *in columns 99-100* gives the definition and the formulas of *the* main harringtonines.

The table [p. 157 recapitulates process of preparation of] *in columns 99-102 summarizes the processes for preparing* harringtonines of *the* prior art.

Figure 1B:
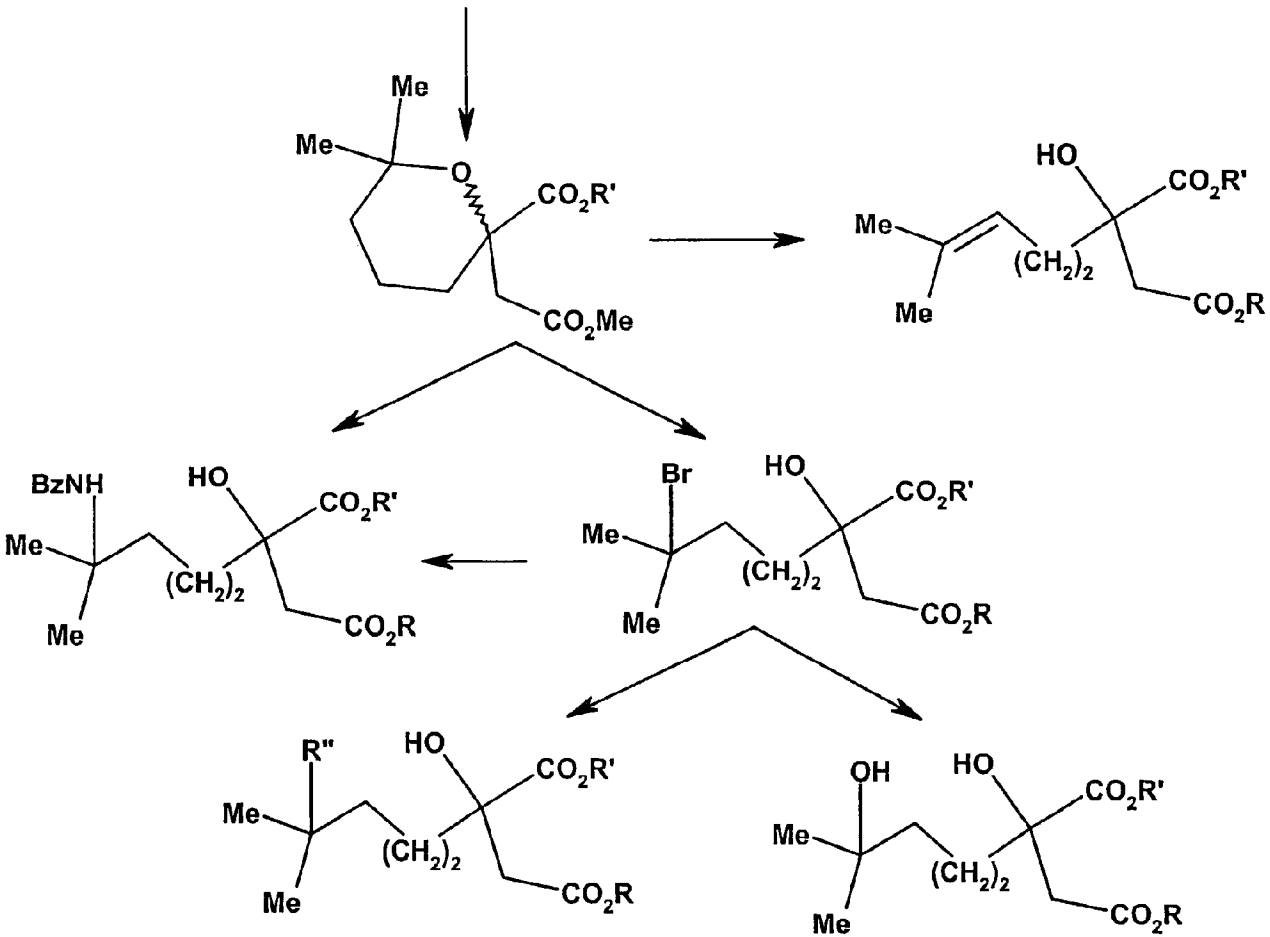

FIGS. 1A and 1B gives the sequence of synthesis of homoharringtonine corresponding to the Example 25, where A represents a 2,4,6-trichloro-phenyl group, R represents a methyl and R' represents a cephalotaxyl moiety.

Figure 2A:
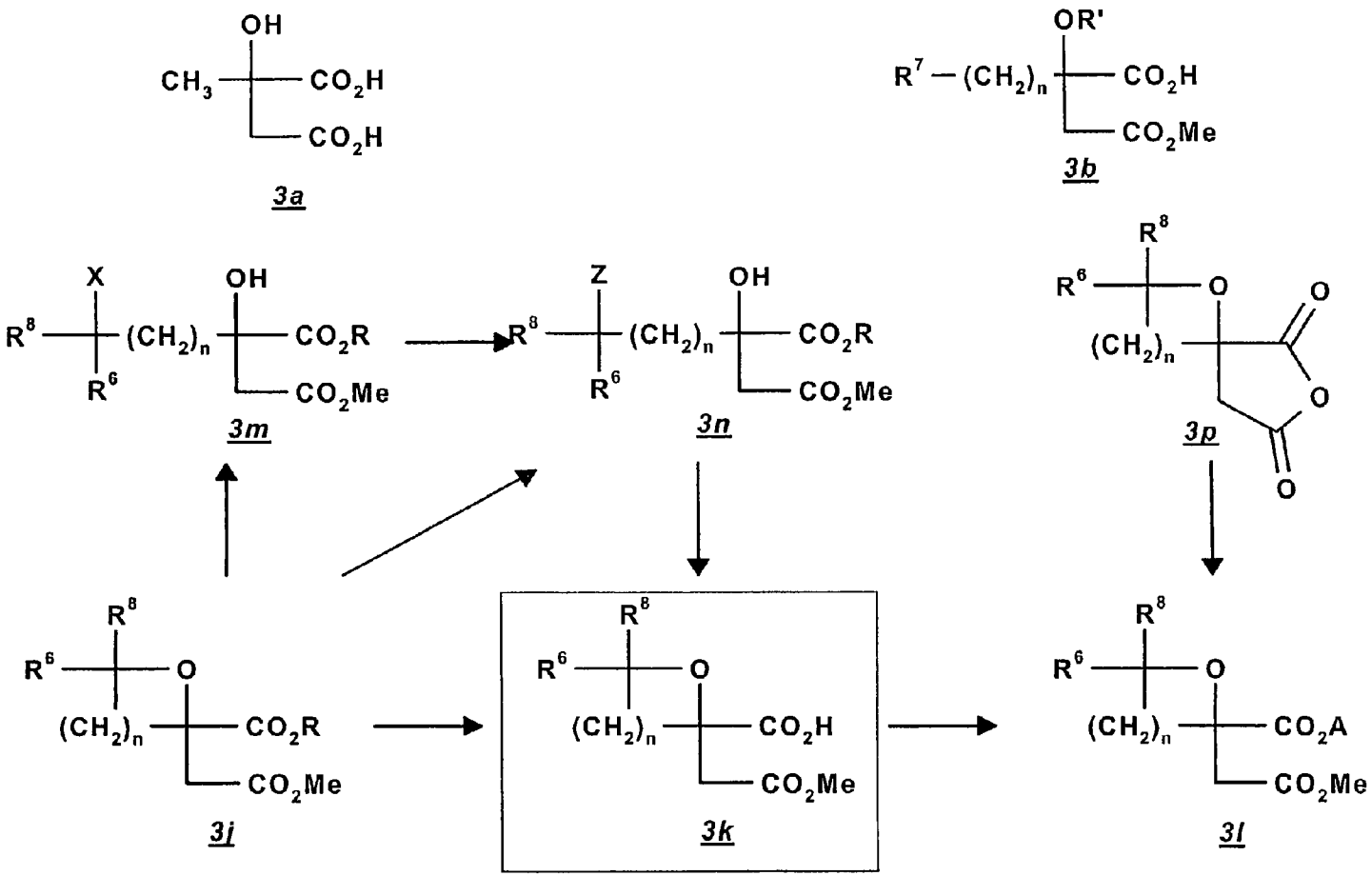
FIGS. 2A and 2B represents a variant of the process according to the invention, more exactly the semi-synthesis of harrintonines via oxacycloalkane carboxylic acids. The substituents $R^6$, $R^7$, $R^8$, R, A, CTX, X and the letters n and m referenced in this scheme are defined in the description.
Figure 2B:
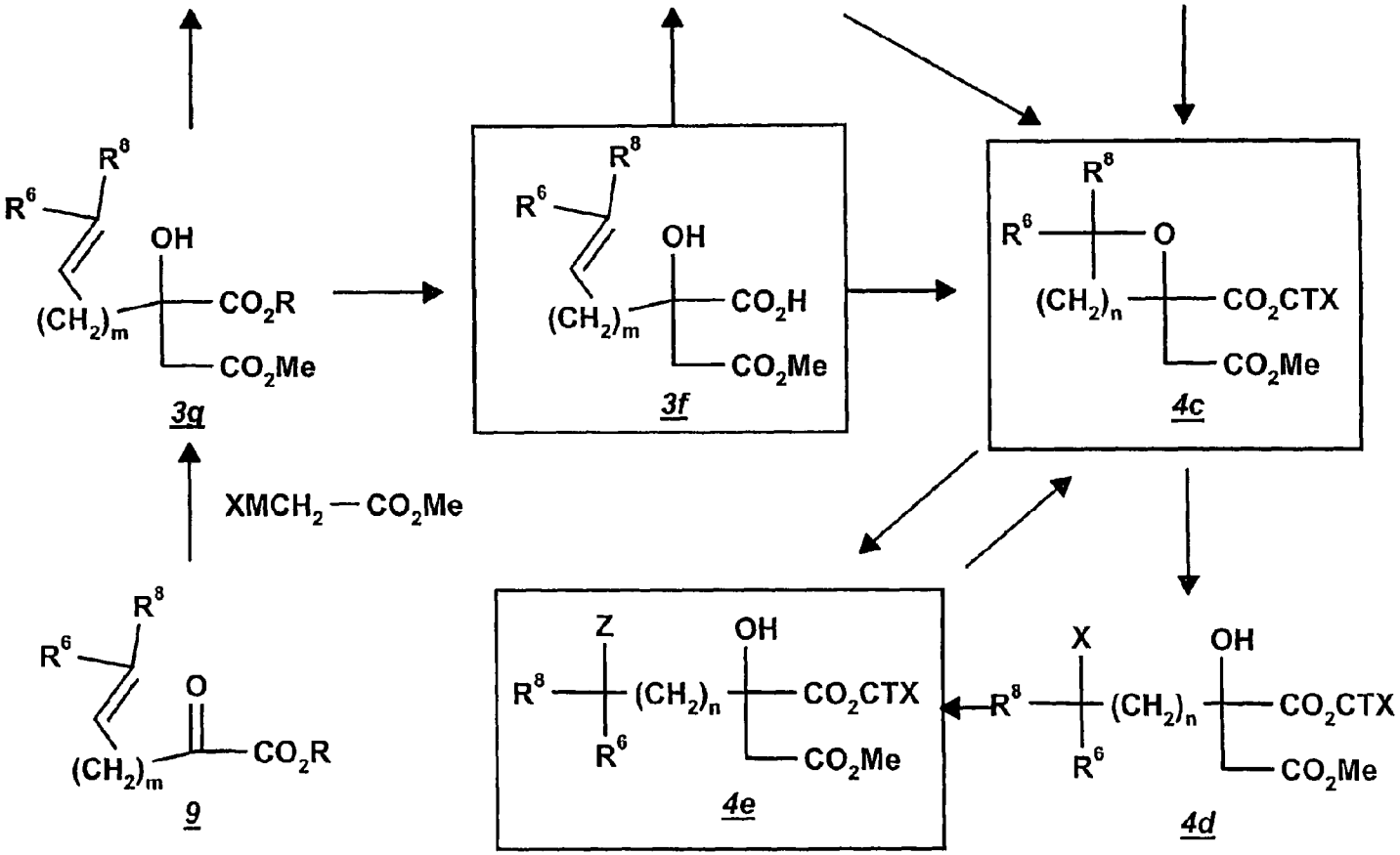

FIGS. 2A and 2B represents a variant of the process according to the invention, more exactly the semi-synthesis of harringtonines via oxacycloalcalne carboxylic acids.

The substitutes $R^6$, $R^7$, $R^8$, R, A, CTX, X and the letters n et m referenced in this scheme are defined in the description.

The present invention also concerns highly purified and crystalline form of harringtonines, definite by their solid state analysis patterns, their process of preparation by purification of crude alkaloids from natural, synthetic or semi-synthetic sources, allowing their use as drug substance for blending alone or in combination in pharmaceutical composition particularly useful for treatment of cancer in using oral mode of administration.

Harringtonines (i.e. harringtonine=HA and homoharringtonine=HHT) are particular cephalotaxine esters, alkaloids isolated from rare and endangered conifers belonging to the Cephalotaxus genus. Cephalotaxine and its natural ester are gathered under the generic term of cephalotaxane.

Two harringtonines are very promising drugs in the treatment of certain leukemia such as Chronic Myelogenous Leukemia (CML). Compassionate use in CML patients resistant or not eligible to all existing therapies is ongoing in France and several phase II and III clinical trials are ongoing in France and in the U.S.

Drug agencies, such as the U.S. Food and Drug Administration, require a high level of purity including enantiomeric, before approval new agents, particularly when these agents are isolated from natural sources. For example, 0.1% an impurity must be qualified and toxicology studies must be performed. New drugs not enantiomerically pure or as racemic mixture are no longer approved by the FDA. In addition, due to large variation of related impurities profil under environmental conditions, drug agencies are particularly suspicious versus drug substances prepared from direct extraction of organisms.

SCHEME 1: DEFINITION NOMENCLATURE AND NUMBERING OF CEPHALOTAXANES

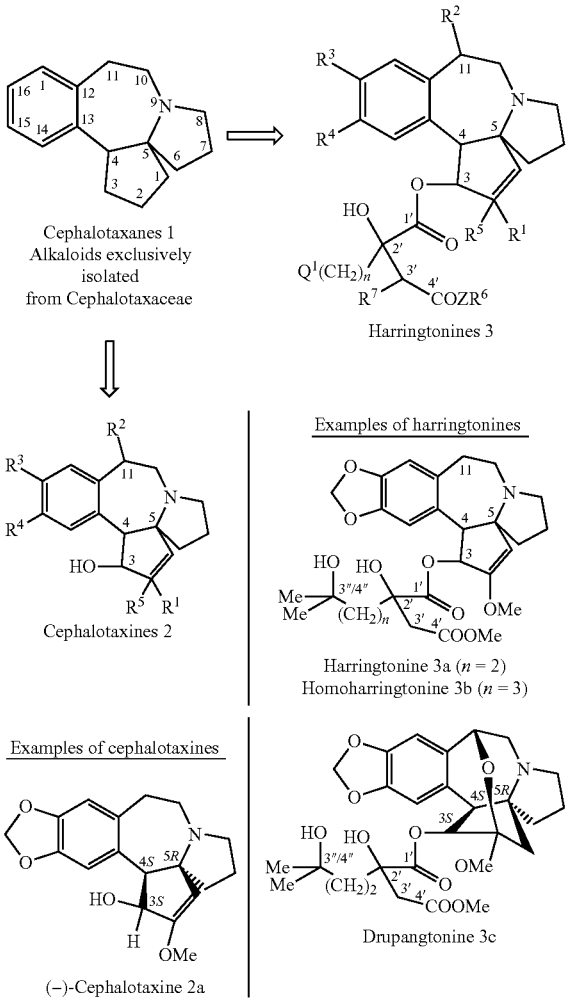

-continued

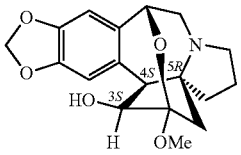

Drupacine 2b

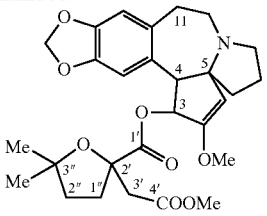

Anhydroharringtonine 3d

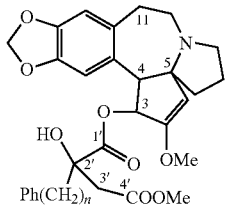

Neoharringtonine 3e ($n$ = 2)

Homoharringtonine and harringtonine are present in Cephalotaxus extract as a complex mixture of several dozens of alkaloids (see scheme 1). For example, HA and HHT were firstly used as a mixture for therapy of cancer and leukemia in China. In the U.S., the level of compliance of drug substances to a given quality required by the FDA is increasing during the process of development of an investigational drug (i.e. from early phase I clinical trial to phase III). In addition, FDA requires that the profile of impurities in term of related compounds shall be reproducible from batch to batch during the marketing phase, that is very difficult when the drug substance is prepared from natural source. An homoharringtonine prepared from natural source was developed by the U.S., the National Cancer Institute and used in its early clinical trials. In despite of a final purification which use a crystallization in ethyl acetate, the final drug substance contains three major impurities including two natural congeners and ethyl analog of HHT which is an artifact of purification resulting from transesterification with the solvent of purification. [He et al., Journ. of Pharm. Biomed. Analysis, 22, pp 541-534 (2000)] The following table, reproduced from reference [He et al., 2000] exemplified the quality of this HHT, which is fact the best quality yielded in using the method of purification the state of art.

TABLE I

Quality Of Various National Cancer Institute (NCI) Clinical Batches Of Homoharringtonine Described In Literature [1] Compared to Semi-Synthetic Batches

| Batch Identification | % Related Comp. A | % Related Comp. b | % Related Comp. c | % Total of Rel. Comp. | % HPLC purity |
|---|---|---|---|---|---|
| NCI Batch #800528 | 0.1 | 1.3 | 0 | 1.4 | 98.6 |
| NCI Batch #871203 | 0 | 1.0 | 0 | 1.0 | 99.0 |
| NCI Batch #921115 | 0.3 | 3.0 | 0.8 | 4.1 | 95.9 |
| NCI Batch #960625 | 0 | 1.8 | 0.3 | 2.1 | 97.9 |
| NCI Batch #800722 | 0.1 | 0.9 | 0.2 | 1.2 | 98.8 |
| NCI Batch #KS-22-130-2 | 0 | 1.5 | 0.9 | 2.4 | 97.6 |
| Average of National Cancer Institute batches | 0.1 | 1.6 | 0.4 | 2.0 | 98.0 |
| Average of Oncopharm's batches | 0.00 | 0.00 | 0.00 | <0.05 | >99.95 |
| Rate Impurities NCI batches/Impurities Oncopharm's Batches | | | | >40 | |

[1] Stability indicating LC assay of and impurity indentification in homoharringtonine samples, He et al., Journ. of Pharm. Biomed. Analysis, 22, pp 541-534 (2000).

FIGS. 8, 9, 12, *and* 14 show [a] chromatographic profiles of harringtonines coming from various sources.

Phase III clinical trial with an HHT drug substance exhibiting a non-reliable impurity profile. [He et al., 2000] The NCI got finally an HHT suitable for use in phase III clinical trial but, despite of its effort, the product they use contains a non-removable impurities of the which contain is higher than 1%. [He et al., 2000]. In addition to the process described for the purification of the NCI production. [He et al., 2000]

Our recent semi-synthesis of harringtonines, including harringtonine and homoharringtonine, by attachment of entirely prior formed acyl side-chains to *the* cephalotaxine moieties, changed [dramatically] this situation *dramatically*: chromatographic purity of the final *harringtonine and homoharringtonine* drug substance is consistently higher [then] *than* 99.8% versus 98.5% for the above cited NCI products (the purest ever previously described) versus 95%-97% for Chinese products, corresponding to 0.2%, [1.5] *1.5%* and 3-5% of impurities (see FIGS. [6, 7 and 12] *8, 9 and 14*). In addition, since cephalotaxine, as *a* precursor of semi-synthetic HA and HHT, is abundant in *a* renewable part of the tree, this semi-synthetic process [overcome] *overcomes* the serious environmental [concern induce] *concerns induced* by the [destroying] *destruction* of a rare and [endanger] *endangered* plant.

A well definite crystalline form of a drug substance is a very important condition, to have reliable solid final form of drugs useful for example for oral administration.

Although HHT and HA would be very promising drugs for the treatment of patients with CML, the current mode of administration by continuous intravenous central infusion (CIVI) is a strong handicap for the administration of this therapy during several years. In addition, while extra-hematologic toxicity of HHT/HA is very mild, the occurrence of infection due to catheter is the main toxicity of this regimen. The use of an oral form of these drugs could be change completely this situation and would extend widely the market of this product.

The present invention provides natural, synthetic or semi-synthetic harringtonines including their tautomeric forms and their salts of the following formula:

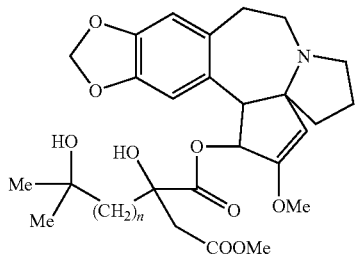

wherein n=2 (i.e. harringtonine) or n=3 (i.e. homoharringtonine), in which:

the total content of impurities, possibly including enantiomeric forms, is lower than 1%, and/or the content of the major impurity is lower than 0.9%, and/or the chromatographic assay exhibits a harringtonines content higher than 97.5%.

A preferred embodiment of the invention provides a natural, synthetic or semi-synthetic homoharringtonine including its tautomeric forms and its salts in which:

the total content of impurities, possibly including enantiomeric forms, is lower than 1%, and/or the content of the major impurity is lower than 0.9%, and/or the chromatographic assay exhibits a homoharringtonines content higher than 97.5%.

A further preferred embodiment of the invention provides a natural, synthetic or semi-synthetic harringtonine including its tautomeric forms and its salts in which:

the total content of impurities, possibly including enantiomeric forms, is lower than 1%, and/or the content of the major impurity is lower than 0.9%, and/or the chromatographic assay exhibits a harringtonine content higher than 97.5%.

A further preferred aspect of the invention is a crystalline natural, synthetic or semi-synthetic homoharringtonine having substantially the same DSC curve as set out in FIG. 3.

Yet, a further embodiment of the invention provides a crystalline natural, synthetic or semi-synthetic homoharringtonine having substantially the same X-ray diffractogram as set out in FIG. 4, and substantially the same IR spectrum, in KBr as set out in FIG. 5.

Yet, another embodiment of the invention provides a crystalline natural, synthetic or semi-synthetic homoharringtonine having substantially the same DSC curve as set out in FIG. 3, and substantially the same X-ray diffractogram as set out in FIG. 4, and substantially the same IR spectrum, in KBr as set out in FIG. 5.

Yet, another preferred embodiment of the invention provides a crystalline natural, synthetic or semi-synthetic harringtonine having substantially the same DSC curve as set out in FIG. 6.

Yet, a preferred aspect of this invention provides a pharmaceutical composition comprising an effective antitumor amount of a natural, synthetic or semi-synthetic homoharringtonine having substantially the same X-ray diffractogram as set out in FIG. 4, and substantially the same IR spectrum, in KBr as set out in FIG. 5, and substantially the same DSC curve as set out in FIG. 3, together with one or more pharmaceutically acceptable inactive components such as carriers, excipients, adjuvants or diluents.

Another aspect of the invention provides a pharmaceutical composition comprising an effective antitumor amount of a natural, synthetic or semi-synthetic harringtonine having substantially the same IR spectrum, in KBr as set out in FIG. 7, and substantially the same DSC curve as set out in FIG. 6, together with one or more pharmaceutically acceptable inactive components such as carriers, excipients, adjuvants or diluents.

Another preferred aspect of the invention provide a process of purification of natural, synthetic or semi-synthetic crude harringtonines for the preparation of pure harringtonines exhibiting the above included features including for eventual enantiomeric enrichment, and comprising the successive steps:

(i) at least one chromatographic purification, preferably in reverse phase in aqueous mobile phase such as a lower alkanol or tetrahydrofurane or acetonitrile, purified water, and an acidic buffer, preferably based on phosphoric acid and is salt. Stationary phase may be any standard chemically bound phase preferably an alkylsilane or an alkylnitrile, bounded on an inert core, preferably silicagel;

(ii) at least one crystallization in water or aqueous solvent containing an organic solvent, preferably a lower $C_{1-4}$ alkanol, The progression of the process of purification is monitored by HPLC analyses and several termal analysis at the solid state. The progression of enantiomeric purity is monitored by optical rotation checking of the dried solid form.

A preferred embodiment provides a new method of monitoring of enantiomeric purity of cephalotaxanes using an HPLC with a chiral stationary phase preferably based upon beta-cyclodextrine Another preferred embodiment of the invention is the above process of purification in which the lower $C_{1-4}$ alkanol is methanol and the cephalotaxane is harringtonine A further preferred aspect of the invention is the above process of purification in which the lower $C_{1-4}$ alkanol is methanol and the cephalotaxane is homoharringtonine This invention include also a pharmaceutical composition which comprises an antitumor effective amount of at least one above described harringtonine or homoharringtonine with one or more pharmaceutically acceptable carriers, excipients or diluents therefore, including the process for preparing the said solid pharmaceutical composition such as, for examples, tablet, capsule, implant or suppository.

Another aspect of the invention is the use of at least the above solid form of one harringtonine or homoharringtonine described in the invention for preparing the above pharmaceutical composition as (i) chemotherapeutic agent, (ii) enhancer of other chemotherapeutic agents (iii) for inhibiting tumors growth, (iv) for inhibiting mammalian parasites, (v) as immunosuppressive agent, or (vi) as reversal agent.

The present invention further describes a method for treating mammalian tumors which comprises administering to a mammal an antitumor effective amount of the solid form of at least one harringtonine or homoharringtonine described in this invention, by parenteral, topic, subcutaneous or anal mode.

A preferred embodiment of the invention describes a method for treating mammalian tumors which comprises oral administering to a mammal an antitumor effective amount of the solid form of at least one harringtonine or homoharringtonine described in this invention.

A further preferred embodiment of the invention describes a method for treating mammalian tumors which comprises implantable pharmaceutical preparation administering to a mammal an antitumor effective amount of the solid form of at least one harringtonine or homoharringtonine described in this invention.

Finally, the invention is also concerned with the use of purified and/or solid harringtonines as defined above, for the preparation of pharmaceutical compositions for the treatment of cancers and leukemias particularly acute myelod leukemia (AML), myelodysplastic syndrome (MDS) and myeloproliferative disorders including chronic myelogenous leukemia.

The following examples, which are given without implied limitation, illustrate the present invention.

EXAMPLE 1

Preparation of ethyl 2-methoxycarbonylmethyl-2-hydroxy-6-methylhept-5-enoate or ethyl 6-desoxy-5,6-dehydrohomoharringtonate

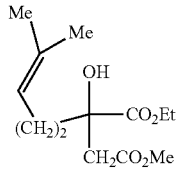

1°) Preparation of the Intermediate Oxalate

5-Bromo-2-methyl-pent-2-ene (15.6 g, 95.6 mmol) was added dropwise to a stirred mixture of magnesium (2.32 g, 95.5 mmol) (activated with further crystal of iodine) in anhydrous tetrahydrofurane (75 ml). The onset of the reaction is accompanied with a vigorous overheating and refluxing of the reaction mixture. The reflux was maintained until most of magnesium had reacted and the reaction mixture was diluted with anhydrous tetrahydrofurane (150 ml). To a stirred mixture of diethyl oxalate (10.8 ml, 80 mmol) in anhydrous tetrahydrofurane (75 ml) was added at −78° C. the resulting Grignard reagent over a period of 20 minutes. The stirring was maintained at −78° C.±5° C. for 30 minutes and then the temperature was raised to −10° C. over a period of 1.5 hours. The mixture was quenched with 15% ammonium chloride solution (300 ml). The separated organic layer was washed with 15% ammonium chloride solution (300 ml) and evaporated to dryness. The aqueous layer was extracted with ether (2×300 ml). The organic layers were combined with the concentrate and washed with brine (300 ml), dried over magnesium sulfate and evaporated to dryness. The crude product, after purification with a bulb-to-bulb distillation apparatus, afforded colorless oil (10.3 g, 70%). The intermediate α-cetoester showed the following characteristics:

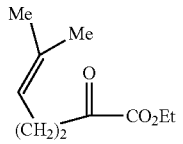

IR (ATR) ($cm^{-1}$): 2790; 2916; 1725; 1068.

$^1$H NMR 400 MHz ($CDCl_3$) (δ ppm, J Hz): 5.08 (1H, t, J=7.2, HC═); 4.32 (2H, q, J=7.1, $OCH_2$); 2.86 (2H, t, J=7.2, $CH_2CO$); 2.32 (2H, q, J=7.2, $CH_2$—C═); 1.68 (3H, s, $CH_3$); 1.62 (3H, s, $CH_3$); 1.37 (3H, t, J=7.1, $OCH_2CH_3$).

2°) Preparation of the Title Product

Anhydrous methyl acetate (0.6 ml, 7.5 mmol) was added to a stirred commercial solution of lithium bis-(trimethylsilylamide) 1M in [tetrahydrofurane] *tetrahydrofuran* (7.5 ml, 7.5 mmol) at −78° C. over a period of 1 minute and [this was allowed] the reaction *was allowed* to proceed at −78±5° C. for 20 minutes. To a stirred mixture of ethyl 2-oxo-6-methylhept-5-enoate prepared above (480 mg, 2.6 mmol) in anhydrous [tetrahydrofurane] *tetrahydrofuran* (10 ml) at −78° C. was added the lithium enolate over a period of 5 minutes, and the resulting mixture was stirred at −78±5° C. for 30 minutes. After monitoring in CCM, the [freezing] *cooling* bath was removed and the mixture was quenched with 15% ammonium chloride solution (10 ml). The separated organic layer was washed *again* with 15% ammonium chloride solution (10 ml) and evaporated to dryness. The aqueous layers were extracted with ether (2×10 ml). The organic layers were combined with the concentrate and washed with brine (10 ml), dried over magnesium sulfate and evaporated to dryness. The resulting crude product (1.13 g) was purified by column chromatography (cyclohexane/ethyl acetate (95:5), silica [(15-40 □m)] (*15-40 μm*) 38 g) to provide a colorless oil (482 mg, 72%). The product thus obtained showed the following characteristics:

IR (ATR) ($cm^{-1}$): 3508; 2969; 2919; 1732; 1438; 1193.

$^1$H NMR 400 MHz ($CDCl_3$) (δ ppm, J Hz): 5.05 (1H, t, J=7.1, HC═); 4.27 (2H, q, J=7.1, $OCH_2$); 3.70 (1H, s, OH); 3.68 (3H, s, $OCH_3$); 2.92 and 2.70 (2H, 2d, $J_{AB}$=16.1, $\underline{CH_2}CO_2$); 2.12 (1H, m); 1.88 (1H, m); 1.72 (2H, m); 1.67 (3H, s, $CH_3$); 1.58 (3H, s, $CH_3$); 1.31 (3H, t, J=7.1, $OCH_2CH_3$).

EXAMPLE 2

Preparation of ethyl 2-methoxycarbonylmethyl-2-hydroxy-6,6-dimethyl-2-tetrahydropyrane carboxylate or ethyl anhydrohomoharringtonate

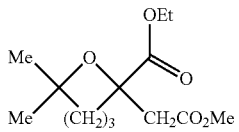

1°) Method A p-Toluenesulfonic acid (2.06 g, 10.8 mmol) was added to a stirred solution of ethylenic ester resulting from Example 1 (2.8 g, 10.8 mmol) in toluene (30 ml) and the resulting mixture was stirred at 65° C. for 5 hours. After cooling at room temperature, the mixture was hydrolyzed with saturated sodium hydrogen carbonate solution. The aqueous layer was extracted with ether (3×50 ml), and the organic layers were combined, washed with brine (100 ml), dried over magnesium sulfate and evaporated to dryness. The resulting crude product (2.8 g) was purified by column chromatography (cyclohexane/ether (95:5), silica (15-40 μm) 10 g) to provide a colorless oil (1.94 g, 69%). The product thus obtained showed the following characteristics:

$^1$H NMR 400 MHz ($CDCl_3$) (δ ppm, J Hz): 4.21 (2H, m, O $\underline{CH_2}CH_3$); 3.64 (3H, s, $OCH_3$); 2.85 and 2.60 (2H, 2d, $J_{AB}$=14.0, $\underline{CH_2}CO_2$); 2.30 (1H, dt, J=13.3 and 3.7); 1.87 (1H, qt, J=13.8 and 3.6); 1.62 (1H, m); 1.51 (2H, m); 1.43 (1H, m); 1.31 (3H, t, J=7.1, $OCH_2\underline{CH_3}$); 1.22 (3H, s, $CH_3$); 1.13 (3H, s, $CH_3$).

2°) Method B

To a stirred solution of ethylenic ester resulting from Example 1 (50 mg, 0.19 mmol) in methanol (30 ml) was added hydrochloric acid 1N (0.5 ml) and the resulting mixture was stirred at 65° C. for 15 hours. After dilution with dichloromethane, the organic layer was dried over magnesium sulfate and evaporated to dryness. The resulting crude product (32 mg) was purified by column chromatography (dichloromethane, then dichloromethane/methanol (9:1), silica (15-40 μm) 2.2 g) to provide the expected intermediate diol (20 m g, 37%). The product thus obtained showed the following characteristics:

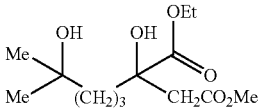

IR (ATR) ($cm^{-1}$): 3490; 2966; 1731; 1193; 1177; 1152.

$^1$H NMR 400 MHz ($CDCl_3$) (δ ppm, J Hz): 4.28 (2H, q, J=7.2, $OCH_2$); 3.75 (1H, s, OH); 3.68 (3H, s, $OCH_3$); 2.93 and 2.69 (2H, 2d, $J_{AB}$=16.2, $\underline{CH_2}CO_2$); 1.70 (2H, m); 1.53 (1H, m); 1.44 (1H, m); 1.30 (3H, t, J=7.1, $OCH_2CH_3$); 1.20 (3H, s, $CH_3$); 1.19 (3H, s, $CH_3$).

To a stirred solution of diol prepared above (19 mg, 0.069 mmol) in 1,2-dichloroethane (1.4 ml) was added anhydrous zinc chloride (10 mg, 0.069 mmol) and the resulting mixture was stirred at 80° C. for 1.5 hours. After cooling at ambient temperature, the mixture was washed with water, then with brine, and the aqueous layer was extracted three times with dichloromethane. The combined organic layers were dried over magnesium sulfate and evaporated to dryness to afford cyclic diester (7 mg, 40%). The product thus obtained showed identical characteristics to this obtained with method A.)

3°) Method C

A solution of ethylenic ester resulting from Example 1 (400 mg, 1.55 mmol) in a mixture of formic acid (4 ml) and water (4 ml) was stirred at 50° C. for 15 hours. After removal of formic acid in vacuo, the residue was treated with 5% sodium hydrogen carbonate solution. The aqueous layer was extracted three times with dichloromethane then the combined organic layers were dried over magnesium sulfate and evaporated to dryness. The resulting crude product (375 mg) was purified by column chromatography (dichloromethane, then dichloromethane/methanol (98:2), silica (15-40 μm) 16 g) to provide a colorless oil (235 mg, 55%). The product thus obtained showed identical characteristics to this obtained with method A. The cyclisation of the diol thus obtained with zinc chloride, like Example 2 method B above, afforded cyclic diester showing identical characteristics to this obtained with method A.

EXAMPLE 3

Preparation of 2-carboxymethyl-2-hydroxy-6-methylhept-5-enoic acid or O-demethyl-6-desoxy-5,6-dehydrohomoharringtonic acid

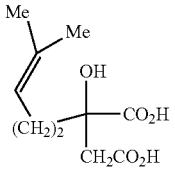

A mixture of potassium hydroxide (14.2 g, 252 mmol) in water (170 ml) was added to a stirred solution of ethylenic ester resulting from Example 1 (10.95 g, 42 mmol) in methanol (300 ml) and the resulting mixture was stirred at reflux for 1.5 hours. After cooling at room temperature, and removal of methanol in vacuo, the residue was treated with water (10 ml) and the resulting aqueous layer was extracted with ether (250 ml). After acidification (pH 1) with 10% hydrochloric acid, the aqueous layer was extracted with ether (3×250 ml). The combined organic layers were dried over magnesium sulfate and evaporated to dryness to afford a white solid (8.66 g, 95%). The crude product thus obtained showed the following characteristics:

IR (ATR) ($cm^{-1}$): 3500; 3019; 2966; 2931; 1716; 1691; 1656; 1219; 1199; 1111.

$^1$H NMR 400 MHz ($CDCl_3$) (δ ppm, J Hz): 5.06 (1H, t, J=6.9, HC═); 3.04 and 2.78 (2H, 2d, $J_{AB}$=17.1, $\underline{CH}2CO_2$); 2.25-1.20 (4H, m, 2×$CH_2$); 1.67 (3H, s, $CH_3$); 1.60 (3H, s, $CH_3$).

EXAMPLE 4

Preparation of 2-carboxymethyl-6,6-dimethyl-2-tetrahydro-pyranecarboxylic acid or O-demethylan-hydrohomoharringtonic acid

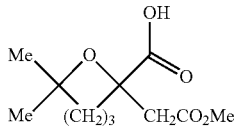

1°) Method A

A mixture of potassium hydroxide (4.2 g, 75 mmol) in water (45 ml) was added to a stirred solution of cyclic diester resulting from Example 2 (1.94 g, 7.5 mmol) in ethanol (75 ml) and the resulting mixture was stirred at reflux for 5 hours. After cooling at room temperature, and removal of ethanol in vacuo, the residue was treated with water (10 ml) and the resulting aqueous layer was extracted with ether (2×50 ml). After acidification with hydrochloric acid 2N (35 ml), the aqueous layer was saturated with sodium chloride then was extracted with ether (3×50 ml). The combined organic layers were washed with brine (2×100 ml) dried over magnesium sulfate and evaporated to dryness to afford a pale yellow oil (1.66 g, 98%). The crude product thus obtained showed the following characteristics:

IR (ATR) ($cm^{-1}$): 2974; 2941; 1709; 1215.

$^1$H NMR 400 MHz ($CDCl_3$) (δ ppm, J Hz): 3.01 and 2.95 (2H, 2d, $J_{AB}$=16.1, $\underline{CH_2}CO_2$); 1.89 (1H, m); 1.75 (2H, m, $CH_2$); 1.58 (3H, m); 1.31 (6H, s, 2×$CH_3$).

2°) Method B

To a stirred solution of ethylenic diacid resulting from Example 3 (50 mg, 23 mmol) in anhydrous toluene (500 μl) was added zinc chloride (6 mg, 0.04 mmol) and the resulting mixture was stirred at 80° C. for 15 hours. After cooling at room temperature, the mixture was hydrolyzed with 10% hydrochloric acid, and the resulting aqueous layer was extracted three times with ethyl acetate. The combined organic layers were dried over magnesium sulfate and evaporated to dryness to afford a pale yellow solid (38 mg, 76%). The crude product thus obtained showed identical characteristics to this obtained with method A.

3°) Method C

A solution of ethylenic diacid resulting from Example 3 (50 mg, 0.23 mmol) in a mixture of formic acid (500 μl) and water (500 μl) was stirred at 60° C. for 3 hours. After cooling at room temperature and removal of formic acid in vacuo, the residue was treated with ethyl acetate. The resulting organic layer was washed with 10% hydrochloric acid and the aqueous layer was extracted three times with ethyl acetate. The combined organic layers were dried over magnesium sulfate and evaporated to dryness to afford a pale yellow solid (50 mg, 100%). The crude product thus obtained showed identical characteristics to this obtained with method A.

EXAMPLE 5

Preparation of 2-methoxycarbonylmethyl-2-hydroxy-6-methylhept-5-enoic acid or 6-desoxy-5,6-dehydrohomoharringtonic acid

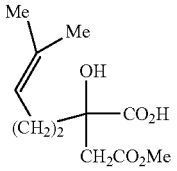

A mixture of ethylenic diacid resulting from Example 3 (500 mg, 2.3 mmol) and a commercial solution of boron trifluoride-methanol complex in methanol (4.5 ml, $BF_3$ 12% w/w) was stirred at 18±5° C. for 16 hours. After careful addition of the reaction mixture at saturated sodium hydrogen carbonate solution (50 ml), the resulting aqueous layer was washed with ether (50 ml), acidified (pH 1) with hydrochloric acid 2N (0.5 ml and extracted with ether (3×50 ml). The combined organic layers were dried over magnesium sulfate and evaporated to dryness to afford a viscous yellow oil (310 mg, 58%). The crude product thus obtained showed the following characteristics:

IR (ATR) ($cm^{-1}$): 3483; 2954; 1731; 1197; 1173.

$^1$H NMR 400 MHz ($CDCl_3$) (δ ppm, J Hz): 5.06 (1H, m, HC=); 4.12 (2H, br.s, $CO_2H$+OH); 3.73 (3H, s, $OCH_3$); 2.99 and 2.74 (2H, 2d, $J_{AB}$=16.7, $\underline{CH_2}CO_2$); 2.16 (1H, m); 1.98 (1H, m); 1.85-1.60 (4H, m); 1.67 (3H, s, $CH_3$); 1.60 (3H, s, $CH_3$).

EXAMPLE 6

Preparation of 2-methoxycarbonylmethyl-6,6-dimethyl-2-tetrahydro-pyranecarboxylic acid or anhydrohomoharringtonic acid)

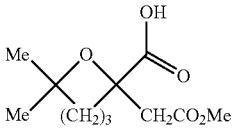

1°) Preparation from Cyclic Diacid

A mixture of cyclic diacid resulting from Example 4 (1.6 mg, 7.4 mmol) and a commercial solution of boron trifluoride-methanol complex in methanol (15.5 ml, $BF_3$ 12% w/w) was stirred at 18±5° C. for 15 hours. After careful addition of the reaction mixture at saturated sodium hydrogen carbonate solution (50 ml), the resulting aqueous layer was washed with ether (2×50 ml) (to see annex preparation below), acidified (pH 1) with hydrochloric acid 2N (15 ml) and extracted with ether (3×75 ml). The combined organic layers were dried over magnesium sulfate and evaporated to dryness to afford a yellow oil (1.17 g, 69%). The crude product thus obtained showed the following characteristics:

IR (ATR) ($cm^{-1}$): 2974; 2951; 1740; 1718; 1437.

$^1$H NMR 400 MHz ($CDCl_3$) (δ ppm, J Hz): 3.70 (3H, s, $OCH_3$); 3.03 and 2.98 (2H, 2d, $J_{AB}$=16.1, $\underline{CH_2}CO_2$); 1.82 (1H, m); 1.74 (3H, m); 1.62 (1H, m); 1.48 (1H, m); 1.31 (3H, s, $CH_3$); 1.26 (3H, s, $CH_3$).

Annex Preparations:

a) Obtaining of Diester

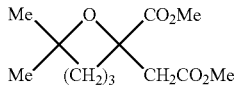

The combined organic layers above-mentioned was dried over magnesium sulfate and evaporated to dryness to afford a mixture of diester and monoester (396 mg). After treatment of this mixture with saturated sodium hydrogen carbonate solution, the aqueous layer was extracted with ether, and the resulting organic layer was dried over magnesium sulfate and evaporated to dryness to afford an oil (292 mg, 17%). The crude product thus obtained showed the following characteristics:

$^1$H NMR 400 MHz ($CDCl_3$) (δ ppm, J Hz): 3.75 (3H, s, $OCH_3$); 3.65 (3H, s, $OCH_3$); 2.85 and 2.61 (2H, 2d, $J_{AB}$=14.1, $\underline{CH_2}CO_2$); 1.85 (1H, m); 1.62 (1H, m); 1.50 (2H, m); 1.43 (1H, m); 1.21 (3H, s, $CH_3$); 1.11 (3H, s, $CH_3$).

b) Obtaining of Regio-Hemiester by Mono Saponification of Diester Above-Mentioned

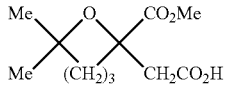

To a stirred solution of cyclic diester above-mentioned (285 mg, 1.17 mmol) in methanol (11 ml) was added a mixture of potassium hydroxide (654 mg, 11.7 mmol) in water (7 ml) and the resulting mixture was stirred at room temperature for 30 minutes. After removal of methanol in vacuo, the residue was treated with water (7 ml) and the resulting aqueous layer was extracted three times with ether. After acidification (pH 1) with 10% hydrochloric acid solution, the aqueous layer was extracted with. The combined organic layers were dried over magnesium sulfate and evaporated to dryness. The resulting crude product (236 mg) was purified by column chromatography (dichloromethane/methanol (95:5), silica (15-40 μm) 6.5 g) to provide a pale yellow solid (220 mg, 82%). The product thus obtained showed the following characteristics:

IR (KBR) ($cm^{-1}$): 3421; 2960; 2929; 1744; 1705; 1209.

$^1$H NMR 400 MHz ($CDCl_3$) δ ppm, J Hz): 3.76 (3H, s, $OCH_3$); 2.76 and 2.67 (2H, 2d, $J_{AB}$=15.3, $\underline{CH_2}CO_2$); 2.36 (1H, m, $J_{AB}$=13.7, $J_{3\text{-}4}$=3.5, $J_{3\text{-}5}$=1.2, H-$3_{eq}$); 1.85 (1H, m, $J_{AB}$~$J_{ax\text{-}ax}$=14.0, $J_{ax\text{-}eq}$=3.7, H-$4_{ax}$); 1.67 (1H, m, $J_{AB}$=14.1, $J_{4\text{-}3,5}$=3.9, H-$4_{eq}$); 1.59 (1H, m, $J_{AB}$=13.4, $J_{5\text{-}4}$=3.6, $J_{5\text{-}3}$=1.0, H-$5_{eq}$); 1.49 (1H, m, $J_{AB}$~$J_{ax\text{-}ax}$=13.2, $J_{ax\text{-}eq}$=4.0, H-$3_{ax}$); 1.42 (1H, m, $J_{AB}$~$J_{ax\text{-}ax}$=13.2, $J_{ax\text{-}eq}$=4.5, H-$5_{ax}$); 1.33 (3H, s, $CH_3$); 1.16 (3H, s, $CH_3$).

2°) Preparation from Ethylenic Hemiester

To a stirred solution of ethylenic hemiester resulting from Example 5 (4.6 g, 20 mmol) in toluene (125 ml) was added p-toluenesulfonic acid (3.8 g, 20 mmol) and the resulting mixture was stirred at 65° C. for 5 hours. After cooling at room temperature, the mixture was hydrolyzed with saturated sodium hydrogen carbonate solution (100 ml). The aqueous layer was washed with ether (2×100 ml) and the organic layers were discarded (to eliminate resulting diester of the reaction). After acidification (pH 1) with hydrochloric acid 1N (35 ml), the aqueous layer was saturated with sodium chloride then was extracted with ether (3×100 ml). The combined organic layers were washed with brine (100 ml) dried over magnesium sulfate and evaporated to dryness.

The resulting crude product (3.9 g) was purified by column chromatography (dichloromethane/methanol (99:1), silica (15-40 μm) 160 g) to provide a yellow oil (3.1 g, 67%). The crude product thus obtained showed identical characteristics to this obtained above.

EXAMPLE 7

Preparation of cyclic anhydride of 2-carboxymethyl-2-hydroxy-6-methylhept-5-enoic acid

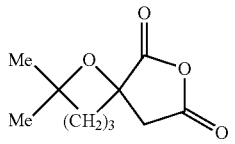

A mixture of cyclic diacid resulting from Example 4 (245 mg, 1.1 mmol) and acetic anhydride (4 ml) was stirred at reflux for 16 hours. After evaporation of reaction mixture in vacuo, the residue was treated with toluene and evaporated again in high vacuum to afford a viscous yellow oil (189 mg, 84%). The product thus obtained showed the following characteristics:

IR (ATR) ($cm^{-1}$): 2976; 2951; 1732; 1188; 1170

$^1$H NMR 400 MHz ($CDCl_3$) (δ ppm, J Hz): 3.02 (2H, s, $\underline{CH_2}CO_2$); 1.98 (2H, m, CH2); 1.8-1.5 (4H, m, $CH_2$); 1.31 (3H, s, $CH_3$); 1.22 (3H, s, $CH_3$).

EXAMPLE 8

Preparation of (−)-Cephalotaxyl Pivalate

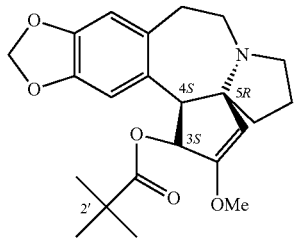

1°) Method Via Mixed Anhydride

To a stirred mixture of pivalic acid (100 mg, 0.98 mmol) in anhydrous toluene (2 ml) was added at room temperature triethylamine (dried over potassium hydroxide) (138 μl, 0.98 mmol) and 2,4,6-trichlorobenzoyl chloride (153 μl, 0.98 mmol). After stirring at 18±5° C. for 1.5 hours (with control of disappearing of starting acid in infra-red), 4-dimethylaminopyridine (139 mg, 1.14 mmol) was added the reaction mixture was allowed to react for 5 minutes and cephalotaxine (103 mg, 0.33 mmol) was added. After stirring at 18±5° C. for 15 hours, the reaction mixture was filtered on paper and diluted with ether (5 ml). The resulting organic layer was successively washed with water (5 ml), with saturated sodium hydrogen carbonate solution (5 ml), with water again (5 ml) then was dried over magnesium sulfate and evaporated in vacuo. The resulting crude product was purified by column chromatography (dichloromethane/methanol (98:2), silica (15-40 μm)) to provide a solid (130 mg, 93%). The product thus obtained showed the following characteristics:

$^1$H NMR 400 MHz ($CDCl_3$) (δ ppm, J Hz): 6.60 (1H, s, H-17*); 6.58 (1H, s, H-14*); 5.84 et 5.83 (2H, 2d, $J_{AB}$=1.5, $OCH_2O$); 5.83 (1H, d, H-3); 5.02 (1H, s, H-1); 3.77 (1H, d, $J_{4-3}$=9.6, H-4); 3.69 (3H, s, $OCH_3$); 3.21 (1H, m, $J_{AB}$=14.0, J=12.5, 7.8, H-11b); 3.09 (1H, m, H-8a); 2.94 (1H, td, J=11.5, 7.1, H-10a); 2.57 (2H, m, H-8b+H-10b); 2.35 (1H, dd, $J_{AB}$=14.5, J=6.9, H-11a); 2.03 (1H, td, $J_{AB}$=12.1, J=9.7, H-$6_A$); 1.89 (1H, m, $J_{AB}$=12.1, J=7.9, 4.0, H-$6_B$); 1.75 (2H, m, $CH_2$-7); 0.83 (9H, s, $C(CH_3)_3$).

2°) Method Using DCC

To a stirred mixture of pivalic acid (50 mg, 0.49 mmol) in anhydrous toluene (2 ml) maintained in an inert atmosphere was added 1,3-dicyclohexylcarbodiimide (130 mg, 0.63 mmol). After stirring for 10 minutes at room temperature, cephalotaxine (50 mg, 0.16 mmol) and pyrrolidinopyridine (24 mg, 0.16 mmol) were added. After stirring at 18±5° C. for 2 hours, then at 50° C. for 15 hours (with control of reaction in CCM, eluant dichloromethane/methanol; 9:1), the reaction mixture was filtered on ground-glass filter, the cake was washed with toluene (5 ml) and the filtrate was evaporated in vacuo. The resulting crude product (130 mg) was purified by column chromatography (dichloromethane/methanol (9:1), silica (15-40 μm) 3g) to provide a white solid (36 mg, 57%). The crude product thus obtained showed identical characteristics to this obtained above via mixed anhydride.

EXAMPLE 9

Preparation of (−)-cephalotaxyl 2-methoxycarbonylmethyl-6,6-dimethyl-2-tetrahydropyrane carboxylate or anhydrohomoharringtonine and methyl 2-cephalotaxyloxy-carbonylmethyl-6,6-dimethyl-2-tetrahydropyrane carboxylate, from cyclic anhydride resulting from Example 7

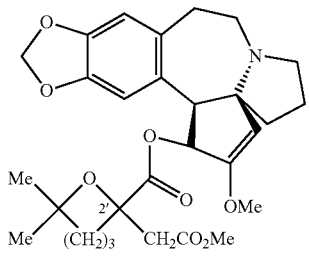

To a stirred mixture of anhydride resulting from Example 7 (50 mg, 0.24 mmol) in anhydrous dichloromethane (0.5 ml) at room temperature were successively added pyridine (250 μl, 3.1 mmol), pyrrolidinopyridine (10 mg, 0.07 mmol) and cephalotaxine (76.4 mg, 0.24 mmol). After stirring at 18±5° C. for 48 hours, were successively added 1,3-dicyclohexylcarbodiimide (100 mg, 0.48 mmol), methanol ([60 □l] *60 μl*, 1.5 mmol), pyrrolidinopyridine (10 mg, 0.07 mmol) and toluene (1 ml). After stirring at 18±5° C. for 24 hours (with control of reaction in CCM), the reaction mixture was filtered and the filtrate was evaporated in vacuo. The resulting crude product was purified by column chromatography (dichloromethane/methanol (99:1), silica (15-40 μm)) to provide expected product (12 mg, two diastereomers) contaminated with regioisomer* (two diastereomers) resulting from the opening of anhydride. The expected product thus obtained showed the following characteristics:

$^1$H NMR 400 MHz ($CDCl_3$) (δ ppm, J Hz): 6.61 (1H, s, H-17*); 6.57 (1H, s, H-14*); 5.91 ($J_{3-4}$=9.8) and 5.84 (2H, 2d, H-3); 5.84 [et] *and* 5.79 (2d, $J_{AB}$=1.4, $OCH_2O$); 5.84 and 5.82 (2d, $J_{AB}$=1.4, $OCH_2O$); 5.04 and 5.01 (1H, 2s, H-1); 3.79 and 3.78 (1H, 2d, $J_{4-3}$=9.6, H-4); 3.70 and 3.65 (3H, 2s, $OCH_3$); 3.59 (3H, s, $OCH_3$); 3.15 (1H, m, [H-11 □] *H-11*β); 3.09 (1H, m, [H-8□] *H-8*α); 2.94 (1H, m, [H-10□] *H-10*α); 2.58 (2H, m, [H-8□+H-10□] *H-8*β+*H-10*β); 2.37 (1H, m, [H-11□] *H-11*α); 2.16 and 1.81 (2d, $J_{AB}$=14.4, $\underline{CH_2}CO_2$); 2.13 and 1.66 (2d, $J_{AB}$=14.3, $\underline{CH_2}CO_2$); 2.02 (1H, m, H-$6_A$); 1.88 (1H, m, H-$6_B$); 1.75 (2H, m, $CH_2$-7); 1.8-1.2 (6H, m, 3×$CH_2$); 1.11 and 1.02 (2s, 2×$CH_3$); 1.10 and 1.04 (2s, 2×$CH_3$).

*The regioisomer above-mentioned was also obtained from the following conditions:

To a stirred mixture of hemiester resulting from Example 6 method C (100 mg, 0.43 mmol) in anhydrous toluene (1 ml) maintained in an inert atmosphere at room temperature was added 1,3-dicyclohexylcarbodiimide (120 mg, 0.58 mmol). After stirring for 5 minutes, cephalotaxine (45 mg, 0.15 mmol) and pyrrolidinopyridine (21 mg, 0.14 mmol) were added. After stirring at 35° C. for 45 minutes, then at 8° C. for 15 hours (with control of reaction in CCM, eluant dichloromethane/methanol; 9:1), the reaction mixture was filtered, the cake was washed with toluene (5 ml) and the filtrate was evaporated in vacuo. The resulting crude product was purified by column chromatography (dichloromethane/methanol (98:2), silica (15-40 μm) 4 g) to provide expected product (23 mg, 30%, two diastereomers). The product thus obtained showed the following characteristics:

$^1$H NMR 400 MHz ($CDCl_3$) (δ ppm, J Hz): 6.61 and 6.58 (1H, 2s, H-17*); 6.57 and 6.53 (1H, 2s, H-14*); 5.89 and 5.86 (2d, $J_{AB}$=1.5, $OCH_2O$); 5.87 and 5.85 (2d, $J_{AB}$=1.5, $OCH_2O$); 5.76 (1H, d, $J_{3-4}$=9.4, H-3); 5.02 (1H, 2s, H-1); 3.73 and 3.72 (1H, 2d, $J_{4-3}$=9.4, H-4); 3.70 and 3.68 (3H, 2s, $OCH_3$); 3.69 and 3.65 (3H, 2s, $OCH_3$); 3.15 (1H, m, [H-11□] *H-11*α); 3.07 (1H, m, [H-8□] *H-8*α); 2.90 (1H, m, [H-10□] *H-10*α); 2.74 and 1.95 (2d, $J_{AB}$=15.3, $\underline{CH_2}CO_2$); 2.56 (2H, m, [H-8□+H-10□] *H-8*β+*H-10*β); 2.33 (1H, m, [H-11□] *H-11*α); 2.28 and 2.23 (2d, $J_{AB}$=15.4, $\underline{CH_2}CO_2$); 2.16 (m, H-$3'_{eq}$); 1.97 (1H, m, H-$6_A$); 1.9-1.1 (5H, m, $CH_2$); 1.86 (1H, m, H-$6_B$); 1.73 (2H, m, $CH_2$-7); 1.14 (3H, s, $CH_3$); 1.03 (3H, s, $CH_3$).

EXAMPLE 10

Preparation of (−)-cephalotaxyl 2-methoxycarbonylmethyl-6,6-dimethyl-2 tetrahydropyrane carboxylate or anhydrohomoharringtonine, from tetrahydropyranecarboxylic acid resulting from Example 6

Formula of Example 9)

1°) Method Via Mixed Anhydride

To a stirred mixture of hemiester resulting from Example 6 (50 mg, 0.22 mmol) in anhydrous toluene (1 ml) at room temperature was added triethylamine (dried over potassium hydroxide) (29.4 μl, 0.22 mmol) and 2,4,6-trichlorobenzoyl chloride (32.7 μl, 0.22 mmol). After stirring at 25° C. for 20 hours (with control of disappearing of starting acid in infra-red), 4-dimethylaminopyridine (29 mg, 0.24 mmol) was added, the reaction mixture was allowed to react for 5 minutes and cephalotaxine (16.5 mg, 0.05 mmol) was added. After stirring at 25° C. for 24 hours, the reaction mixture was filtered on paper and diluted with ether (5 ml). The resulting organic layer was successively washed with water (5 ml), with saturated sodium hydrogen carbonate solution (5 ml), with water again (5 ml), then was dried over magnesium sulfate and evaporated in vacuo. The resulting crude product was purified by column chromatography (dichloromethane/methanol (98:2), silica (15-40 μm)) to provide expected product (16 mg, 56%, two diastereomers). The product thus obtained showed identical characteristics to this obtained in Example 9.

2°) Method Using DCC

To a stirred mixture of hemiester resulting from Example 6 (100 mg, 0.43 mmol) in anhydrous toluene (1 ml) maintained in an inert atmosphere at room temperature was added 1,3-dicyclohexylcarbodiimide (180 mg, 0.87 mmol). After stirring for 10 minutes, cephalotaxine (165 mg, 0.52 mmol) and pyrrolidinopyridine (77 mg, 0.52 mmol) were added. After stirring at 18±5° C. for 18 hours, was added ether, the reaction mixture was filtered on ground-glass filter, and the cake was washed with ether. The resulting organic layer was successively washed with 10% sodium hydrogen carbonate solution, with water, then was dried over magnesium sulfate and evaporated in vacuo. The resulting crude product was purified by column chromatography (dichloromethane/methanol (98:2), silica (15-40 μm) 9 g) to provide a solid (110 mg, 48%). The product thus obtained showed identical characteristics to this obtained in Example 9.

EXAMPLE 11

Preparation of (−)-cephalotaxyl(2'RS)-2-methoxycarbonylmethyl-6,6-dimethyl-2-tetrahydropyrane carboxylate or anhydrohomoharringtonine, from ethylenic acid resulting from Example 6

Formula of Example 9

1°) Method A: Via Mixed Anhydride, Coupling with Cyclisation

To a stirred mixture of ethylenic ester resulting from Example 5 (50 mg, 0.22 mmol) in anhydrous toluene (1 ml) at room temperature was added triethylamine (dried over potassium hydroxide) (29 μl, 0.22 mmol) and 2,4,6-trichlorobenzoyl chloride (34 μl, 0.22 mmol). After stirring for 30 minutes (with control of disappearing of starting acid in infra-red), 4-dimethylaminopyridine (30 mg, 0.25 mmol) was added, the reaction mixture was allowed to react for 5 minutes and cephalotaxine (31 mg, 0.1 mmol) was added. After stirring at 18±5° C. for 65 hours, the reaction mixture was filtered on paper and diluted with ether (5 ml). The resulting organic layer was successively washed with water (5 ml), with saturated sodium hydrogen carbonate solution (5 ml), with water again (5 ml), then was dried over magnesium sulfate and evaporated in vacuo. The resulting crude product was purified by column chromatography (dichloromethane/methanol (98:2), silica (15-40 μm)) to provide expected product (46 mg, 96%, two diastereomers 40/60). The product thus obtained showed identical characteristics to this obtained in Example 9.

2°) Method B: Using DCC, Coupling with Cyclisation

To a stirred mixture of ethylenic acid resulting from Example 5 (50 mg, 0.22 mmol) in anhydrous toluene (2 ml)

maintained in an inert atmosphere at room temperature was added 1,3-dicyclohexylcarbodiimide (270 mg, 1.31 mmol). After stirring for 5 minutes, cephalotaxine (70 mg, 0.22 mmol) and pyrrolidinopyridine (32 mg, 0.22 mmol) were added. After stirring at 18±5° C. for 65 hours (with control of reaction in CCM, eluant dichloromethane/methanol; 9:1), the reaction mixture was filtered on ground-glass filter, the cake was washed with toluene (5 ml) and the filtrate was evaporated in vacuo. The resulting crude product was purified by column chromatography (dichloromethane/methanol (98:2), silica (15-40 μm) 9 g) to provide a solid (40 mg, 35%). The product thus obtained showed identical characteristics to this obtained in Example 9.

EXAMPLE 12

Preparation of Purified (−) Cephalotaxine from Total Alkaloidic Extract of Cephalotaxus sp

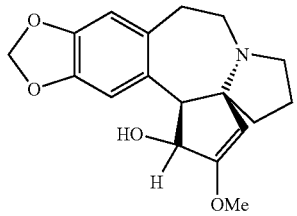

1°) Preparation of Total Alkaloids Extract:

In a 30 liters-tank, crushed leaves (fresh or dry) of Cephalotaxus sp (10 kg) were mixed with methanol (201) and steed during 65 hours, then percolated (501). Solution was filtered and concentrated under vacuum to a volume of 51. Concentrated solution was acidified with a 6% aqueous solution of tartaric acid. Then hydro-alcoholic solution was washed by dichloromethane (5×51) for removing fatty materials and pigments. Aqueous solution was basified with aqueous ammonia (2.5%) until pH 9, then extracted with dichloromethane (5×51). After concentration under reduced pressure, crude alkaloids extract was recovered as a white crystalline solid (24.5 g). Cephalotaxine contain was 71% (HPLC).

2°) Isolation and Chromatographic Purification of (−)-cephalotaxine from Crude Alkaloids Extract:

Above crude extract was dissolved in mobile phase (triethylamine (1.55/1000) in deionised water and orthophosphoric acid to adjust pH to 3. The solution was filtered then injected on a preparative high-performance liquid chromatograph equipped with axial compression and high pressure pump (stationary phase: n-octadecylsilane, 15 m, porosity 100, 1 kg). Elution was performed at a flow rate of 0.2 l/min. Fractions contain was monitored by U.V. detector and TLC. Retained fraction were finally checked by HPLC then combined, alkalinised with 2.5% aqueous ammonia and extracted with dichloromethane (4×400 ml), After concentration under reduced pressure a resin was obtained which on trituration with methanol gave (−)-cephalotaxine (18g) as a white crystalline solid (HPLC purity=99.8%). The product thus obtained showed the following characteristics:

$[\alpha]_D^{20}$: −174.1 (c=0.20; $CHCl_3$)

$^1$NMR 400 MHz ($CDCl_3$) (δ ppm, J Hz): 6.68 (1H, s, H-17*); 6.65 (1H, s, H-14*); 5.91 and 5.90 (2H, 2d, $J_{AB}$=1.5, $OCH_2O$); 4.93 (1H, s, H-1); 4.77 (1H, dd, $J_{3\text{-}4}$=9.4, $J_{3\text{-}OH}$=3.4, H-3); 3.73 (3H, s, $OCH_3$) 3.68 (1H, d, $J_{4\text{-}3}$=9.4, H-4); 3.35 (1H, m, $J_{AB}$=14.3, J=12.2 and 7.9, H-11β); 3.08 (1H, m, J=9.1 and 4.9, H-8α); 2.92 (1H, td, J=11.6 and 7.1, H-10α); 2.59 (2H, m, H-8α+H-10α); 2.35 (1H, dd, $J_{AB}$=14.4, J=6.9, H-11α); 2.02 (1H, td, $J_{AB}$=12.1, J=9.7, H-$6_A$); 1.87 (1H, m, $J_{AB}$=12.1, J=7.9 and 4.4, H-$6_B$); 1.74 (2H, m, $CH_2$-7); 1.62 (1H, d, $J_{3\text{-}OH}$=3.5, 3-OH).

EXAMPLE 13

Preparation of Lithium Alcoolate of (−) cephalotaxine (Trapped Like 3-O-acetyl Derivative)

1°) Butyllithium Method

A commercial solution of butyllithium in hexane (0.44 ml, 1.6 M in hexane, 0.70 mmol) was added to a stirred mixture of (−)-cephalotaxine (200 mg, 0.63 mmol) in anhydrous tetrahydrofurane (6.8 ml). The reaction mixture was maintained at −60° C. for 20 minutes, then at −48° C. for 30 minutes, acetic anhydride (90 μl, 0.095 mmol) was added over a period of 8 minutes and the stirring was maintained at −48° C. for 20 minutes then at 0° C. for 1 hour. The mixture was quenched with saturated ammonium chloride solution (5 ml) then extracted with ethyl acetate (3×8 ml). The combined organic layers were washed with brine (15 ml) dried over magnesium sulfate and evaporated to dryness. The resulting crude product was purified by column chromatography (dichloromethane/methanol (98:2), silica (15-40 μm) 6 g) to provide a white solid (60 mg, 26%). The product thus obtained showed the following characteristics:

$^1$H NMR 400 MHz ($CDCl_3$) (δ ppm, J Hz): 6.60 (1H, s, H-17*); 6.57 (1H, s, H-14*); 5.89 and 5.86 (2H, 2d, $J_{AB}$=1.4, $OCH_2O$); 5.80 (1H, d, $J_{3\text{-}4}$=9.3, H-3); 5.05 (1H, s, H-1); 3.77 (1H, d, $J_{4\text{-}3}$=9.4, H-4); 3.72 (3H, s, $OCH_3$); 3.23 (1H, m, $J_{AB}$=14.3, J=12.3 and 7.9, H-11β); 3.08 (1H, m, H-8α); 2.92 (1H, td, J=11.5 and 7.1, H-10α); 2.57 (2H, m, H-8β+H-10β); 2.36 (1H, dd, $J_{AB}$=14.4, J=7.0, H-11β); 2.02 (1H, td, $J_{AB}$=12.1, J=9.7, H-$6_A$); 1.88 (1H, m, $J_{AB}$=12.1, J=8.0 and 4.0, H-$6_B$); 1.74 (2H, m, $CH_2$-7); 1.57 (3H, s, OAc).

2°) Lithium bis-(trimethylsilyl)amide (LHDS) Method

A commercial solution of lithium bis-(trimethylsilylamide) 1M in tetrahydrofurane (0.95 ml, 0.95 mmol) was added to a stirred solution of (−)-cephalotaxine (200 mg, 0.63 mmol) in anhydrous tetrahydrofurane at −40° C. After stirring for 5 minutes, acetic anhydride (90 μl, 0.95 mmol) was added, and the reaction mixture was treated like method above-mentioned in 1°). The product thus obtained showed identical characteristics to this obtained above in butyllithium method.

3°) Lithium Diisopropylamide (LDA) Method

A commercial solution of lithium diisopropylamide 2M in tetrahydrofarane (0.35 ml, 0.70 mmol) was added to a stirred solution of (−)-cephalotaxine (200 mg, 0.63 mmol) in anhydrous tetrahydrofurane (6.8 ml) at −60° C. over a period of 20 minutes After stirring at −60° C. for 20 minutes, then at −48° C. for 30 minutes, acetic anhydride (90 μl, 0.95 mmol) was added. The solution was stirred at −48° C. for 20 minutes, then at 0° C. for 1 hour and the reaction mixture was treated like method above-mentioned in 1°). The product thus obtained showed identical characteristics to this obtained above in butyllithium method.

4°) Sodium Hydride Method

To a stirred mixture of sodium hydride (1.5 g) in freshly distilled dimethylformamide (3 ml) were added at −60° C. a solution of cephalotaxine (200 mg, 0.63 mmol) in dimethylformamide (3 ml) and acetic anhydride (90 μl, 0.95 mmol). After stirring at ambient temperature for 24 hours, the reaction mixture was treated at 0° C. with water (3 ml) and extracted with ether (3×5 ml). The combined organic layers were dried over magnesium sulfate and evaporated on vacuum. The product thus obtained showed identical characteristics to this obtained above in butyllithium method.

EXAMPLE 14

Preparation of (−)-cephalotaxyl 2-methoxycarbonyl-methyl-6,6-dimethyl-2-tetrahydropyrane carboxylate or anhydrohomoharringtonine, via Lithium Alcoolate of Cephalotaxine Formula of Example 9

To a stirred solution of lithium alcoolate of (−)-cephalotaxine (158 mg, 0.5 mmol) in anhydrous tetrahydrofurane prepared according to Example 13 was added mixed anhydride resulting from Example 10 (0.75 mmol) at −50° C. over a period of 10 minutes. After stirring at −50° C. for 30 minutes, then at 0° C. for 2 hours, the reaction mixture was quenched with saturated ammonium chloride solution (5 ml) and extracted with ethyl acetate (3×10 ml). The combined organic layers were washed with brine (15 ml) dried over magnesium sulfate and evaporated in vacuo. The resulting crude product was purified by column chromatography (dichloromethane/methanol (98:2), silica (15-40 μm) 7 g) to provide a white solid (48 mg). The product thus obtained showed identical characteristics to this obtained in Example 9.

EXAMPLE 15

Preparation of Diastereomeric Mixture of (−)-quinidyl 2-methoxycarbonyl-methyl-6,6-dimethyl-2-tetrahydropyrane carboxylates, from tetrahydropyranecarboxylic acid Resulting from Example 6

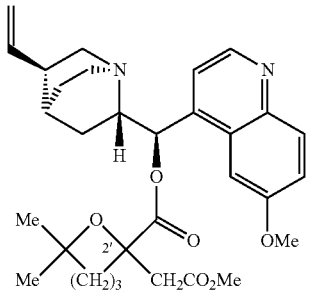

1°) Method A: Via Mixed Anhydride

To a stirred mixture of acid resulting from Example 6 (458 mg, 1.99 mmol) in anhydrous toluene (8 ml) at room temperature was added triethylamine (dried over potassium hydroxide) (270 μl, 1.92 mmol) and 2,4,6-trichlorobenzoyl chloride (300 μl, 1.91 mmol). After stirring for 3 hours (with control of disappearing of starting acid in infra-red), 4-dimethylaminopyridine (352 mg, 2.88 mmol) was added, the reaction mixture was allowed to react for 5 minutes and quinine (936 mg, 2.88 mmol) was added. After stirring at 18±5° C. for 65 hours, the reaction mixture was filtered on paper and diluted with ether (15 ml). The resulting organic layer was successively washed with water (15 ml), with saturated sodium hydrogen carbonate solution (15 ml), with water again (15 ml) then was dried over magnesium sulfate and evaporated in vacuo. The resulting crude product was purified by column chromatography (dichloromethane/methanol (99:1), silica (15-40 [□m] μm) 32 g) to provide expected product (930 mg, 84%, two diastereomers 50/50). The product thus obtained showed the following characteristics:

$^1$H NMR 400 MHz ($CDCl_3$) (δ ppm, J Hz): 8.73 (1H, m, H-$2_{qn}$), 8.0 and 7.98 (1H, 2d, J=9.2, H-$8_{qn}$); 7.63 and 7.50 (1H, 2br.s); 7.45 (br.s) and 7.39 (d, J=4.5) (1H, H-$3_{qn}$); 7.36 (1H, dd, J=9.1 and 2.6, H-$7_{qn}$); 6.50 (1H, br.s); 5.89 (1H, m, $=CH_{qn}$); 5.03 (2H, m, $=CH_{2qn}$); 3.99 and 3.97 (3H, 2s, $OCH_3$); 3.54 and 3.33 (3H, 2br.s, $OCH_3$); 3.2-1.0 (m, [7□] 7×$CH_2$+3CH); 2.92 and 2.67 (2d, $J_{AB}$=14.9, $\underline{CH_2}CO_2$); 2.87 (d, $J_{AB}$=14.8, $\underline{CH_2}CO_2$); 1.17 and 0.99 (2s, 2×$CH_3$); 1.03 and 0.42 (2br.s, 2×$CH_3$).

2°) Method B: DCC

To a stirred mixture of tetrahydrocarboxylic acid resulting from Example 6 (200 mg, 0.87 mmol) in anhydrous toluene (4 ml) maintained in an inert atmosphere at room temperature was added 1,3-dicyclohexylcarbodiimide (239 mg, 1.16 mmol). After stirring for 5 minutes, quinine (94 mg, 0.29 mmol) and pyrrolidinopyridine (43 mg, 0.29 mmol) were added. After stirring at 18±5° C. for 65 hours (with control of reaction in CCM, eluant dichloromethane/methanol; 9:1), the reaction mixture was filtered on ground-glass filter, the cake was washed with toluene (5 ml) and the filtrate was evaporated in vacuo. The resulting crude product was purified by column chromatography (dichloromethane/methanol (9:1), silica (15-40 μm)) to provide the expected product (96 mg, 60%, two diastereomers 50/50). The product thus obtained showed identical characteristics to this obtained above.

EXAMPLE 16

Preparation of (−)-menthyl 2-methoxycarbonylmethyl-6,6-dimethyl-2-tetrahydro-pyrane carboxylate, tetrahydropyrane-carboxylic acid resulting from Example 6

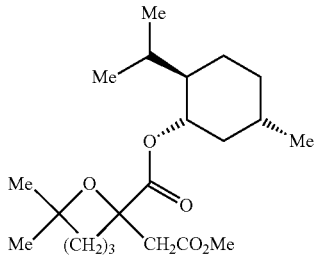

To a stirred mixture of acid resulting from Example 6 (50 mg, 0.22 mmol) in anhydrous toluene (1 ml) maintained in an inert atmosphere at room temperature was added 1,3-dicyclohexylcarbodiimide (90 mg, 0.44 mmol). After stirring for 5 minutes, (−)-menthol (68 mg, 0.44 mmol) and pyrrolidinopyridine (64 mg, 0.44 mmol) were added. After stirring at 30° C. for 1 hour, then at 8° C. for 15 hours (with control of reaction in CCM, eluant dichloromethane/methanol; 9:1), the reaction mixture was filtered on ground-glass filter, the cake was washed with toluene (5 ml) and the filtrate was evaporated in vacuo. The resulting crude product was purified by column chromatography (cyclohexane/ethyl acetate (95:5 then 90:10), silica (15-40 μm) 4 g) to provide the expected product (40 mg, 50%, two diastereomers 60/40). The product thus obtained showed the following characteristics:

$^1$H NMR 400 MHz ($CDCl_3$) (δ ppm, J Hz): 4.68 (1H, m, H-$1_{men}$); 3.64 (3H, s, $OCH_3$); 2.84 and 2.64 (2d, $J_{AB}$=14.6, $\underline{CH_2}CO_2$); 2.83 and 2.63 (2d, $J_{AB}$=14.3, $\underline{CH_2}CO_2$); 2.29 (1H, m, H-$3_{eq}$); 2.1-0.8 (m, CH and $CH_2$); 1.21 (3H, 2s, $CH_3$); 1.17 and 1.16 (3H, 2s, $CH_3$); 0.9 and 0.88 (6H, 2d, J=6.4, [2□] 2×$CH_{3men}$); 0.74 and 0.72 (3H, 2d, J=6.8, $CH_{3men}$).

EXAMPLE 17

Preparation of (−)-methyl mandelate 2-methoxycarbonylmethyl-6,6-dimethyl-2-tetrahydropyrane carboxylate from tetrahydropyranecarboxylic acid Resulting from Example 6

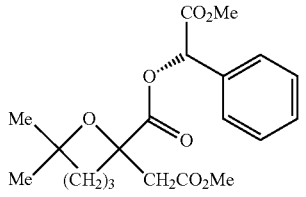

To a stirred mixture of tetrahydropyranecarboxylic acid resulting from Example 6 (226 mg, 0.98 mmol) in anhydrous toluene (4 ml) maintained in an inert atmosphere at room temperature was added 1,3-dicyclohexylcarbodiimide (261 mg, 1.2 mmol). After stirring for 5 minutes, menthyl mandelate (53 mg, 0.32 mmol) and pyrrolidinopyridine (47 mg, 0.32 mmol) were added. After stirring at 18±5° C. for 12 hours, the reaction mixture was filtered on ground-glass filter, the cake was washed with toluene (5 ml) and the filtrate was evaporated in vacuo. The resulting crude product was purified by column chromatography (dichloromethane/methanol (9:1), silica (15-40 μm)) to provide a colorless oil (64 mg, 17%, two diastereomers). The product thus obtained showed the following characteristics:

$^1$H NMR 400 MHz ($CDCl_3$) (δppm, J Hz): 7.47 (2H, m, Ph); 7.38 (3H, m, Ph); 5.96 (1H, s, CH); 3.73 and 3.72 (3H, 2s, $OCH_3$); 3.54 (3H, 2s, $OCH_3$); 2.88 and 2.72 (2d, $J_{AB}$=14.4, $\underline{CH_2}CO_2$); 2.85 and 2.65 (2d, $J_{AB}$=14.2, $\underline{CH_2}CO_2$); 2.35 (1H, m, H-$3_{eq}$); 2.0-1.15 (5H, m, $CH_2$); 1.23 and 1.22 (3H, 2s, $CH_3$); 1.19 and 1.07 (3H, 2s, $CH_3$).

EXAMPLE 18

Separation of (−)-quinyl(2'R)-anhydrohomoharringtonate and (−)-quinyl(2'S)-anhydrohomoharringtonate from Diastereomeric Mixture Resulting from Example 15

[Diastereomeric] *A diastereomeric* mixture of (−)-quinyl (2'R)-anhydrohomoharringtonate and *of* (−)-quinyl(2'S)-anhydrohomoharringtonate (5 g) was [submit] *submitted* to preparative HPLC. [Above] *The* mixture was dissolved in buffer (triethylamine (1.55/1000) in [deionised] *deionized* water and orthophosphoric acid to adjust pH to 3. The solution was filtered then injected [on] *onto* a preparative high-performance liquid chromatograph equipped with axial compression and high pressure pump (stationary phase: n-octadecylsilane, [15 □m] *15 μm*, porosity 100, 1 kg; mobile phase: buffer/acetonitrile 70/30). Elution was performed at a flow rate of 0.2 l/min. Fractions [contain was] *were* monitored by U.V. detector and TLC. Retained [fraction] *fractions* were finally checked by HPLC then combined, alkalinised with 2.5% aqueous ammonia and extracted with dichloromethane (4×400 ml)[.]. After concentration under reduced pressure the two separated isomers were obtained as white crystalline solids corresponding to (−)-quinyl(2'R)-anhydrohomoharringtonate (2 g) and (−)-quinyl(2'S)anhydrohomoharringtonate (2.2 g). The products thus obtained showed the following characteristics:

1°) Diastereomer 2'R

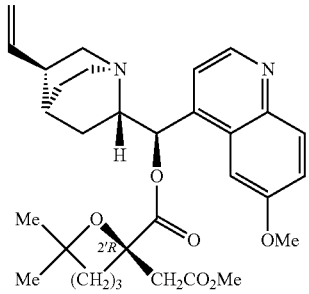

IR (film NaCl) ($cm^{-1}$): 2947; 2871; 1743; 1626; 1509.

$^1$H NMR 400 MHz ($CDCl_3$) (δ ppm, J Hz): 8.73 (1H, d, J=4.4, H-$2_{qn}$), 8.0 (1H, d, J=9.2, H-$8_{qn}$); 7.50 (1H, br.s); 7.39 (1H, d, J=4.5, H-$3_{qn}$); 7.36 (1H, dd, H-$7_{qn}$); 6.39 (1H, br.s); 5.88 (1H, m, =$CH_{qn}$); 5.03 (2H, m, =$CH_{2qn}$,); 3.97 (3H, s, $OCH_3$); 3.31 (3H, br.s, $OCH_3$); 3.5-1.2 (m, 7×$CH_2$+3CH); 2.86 and 2.64 (2H, 2d, $J_{AB}$=15.0, $\underline{CH_2}CO_2$); 1.17 (3H, s, $CH_3$); 0.99 (3H, s, $CH_3$).

2°) Diastereomer 2'S

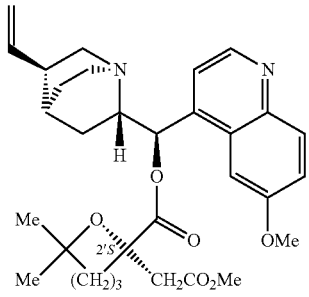

IR (film NaCl) ($cm^{-1}$): 2947; 2871; 1743; 1626; 1509.

$^1$H NMR 400 MHz ($CDCl_3$) (δ ppm, J Hz): 8.74 (1H, d, J=4.4, H-$2_{qn}$), 7.99 (1H, d, J=9.2, H-$8_{qn}$); 7.65 (1H, br.s, H-$3_{qn}$); 7.44 (1H, br.s, H-$5_{qn}$); 7.36 (1H, dd, J=9.2 and 2.7, H-$7_{qn}$); 6.55 (1H, br.s); 5.89 (1H, m, =$CH_{qn}$); 5.05 (2H, m, =$CH_{2qn}$); 3.99 (3H, s, $OCH_3$); 3.54 (3H, s, $OCH_3$); 3.1-1.0 (m, 7×$CH_2$+3CH); 2.91 and 2.67 (2H, 2d, $J_{AB}$=15.0, $\underline{CH_2}CO_2$); 1.03 (3H, br.s, $CH_3$); 0.44 (3H, br.s, $CH_3$).

EXAMPLE 19

Preparation of (2R)-anhydrohomoharringtonic acid from (−)-quinyl(2'R)-anhydrohomoharringtonate resulting from Example 18

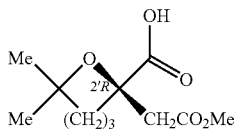

1°) Obtaining Via Hydrogenolysis

To a stirred solution of quinyl (2'R)-anhydroharringtonate (100 mg, 0.19 mmol) in ethyl acetate (11 ml) was added 10% palladium on charcoal (40 mg). The resulting mixture was stirred at room temperature under hydrogen pressure (50 p.s.i.) for 20 hours, and after CCM control the reaction mixture was filtered and the resulting organic layer was treated with saturated sodium hydrogen carbonate solution. The aqueous layer was washed with ethyl acetate, and after acidification with hydrochloric acid 1N was extracted with ethyl acetate. The combined organic layers were washed with brine, dried over magnesium sulfate and evaporated to dryness to afford a yellow solid (20 mg, 50%). The product thus obtained showed the following characteristics:

$[\alpha]_D^{20}$: −23 (c=0.38; $CHCl_3$).

IR (film NaCl) ($cm^{-1}$): 2974; 2951; 1740; 1718; 1437.

$^1H$ NMR 400 MHz ($CDCl_3$) (δ ppm, J Hz): $^1H$ NMR spectra of the product thus obtained was identical to this described in Example 6-1.

2°) Obtaining Via Total Saponification then Selective Methylation

A mixture of potassium hydroxide (396 mg, 7.1 mmol) in water (8 ml) was added to a stirred solution of quinyl(2'R)-anhydroharringtonate (396 g. 0.72 mmol) in ethanol (15 ml) and the resulting mixture was stirred at reflux for 24 hours. After cooling at room temperature and removal of ethanol in vacuo, the residue was treated with water (10 ml) and the resulting aqueous layer was extracted with ether (4×15 ml). After acidification (pH 1) with hydrochloric acid 2N and saturation with sodium chloride, the aqueous layer was extracted with ethyl acetate (3×15 ml). The combined organic layers were dried over magnesium sulfate and evaporated to dryness to afford a yellow solid (110 mg, 72%). The intermediate diacid thus obtained showed the following characteristics:

$[\alpha]_D^{20}$: −14 (c=0.54; $CHCl_3$)

IR (film NaCl) ($cm^{-1}$): 2975; 2941; 1716; 1217.

$^1H$ NMR 400 MHz ($CDCl_3$) (δ ppm, J Hz): $^1H$ NMR spectra of the product thus obtained was identical to this described in Example 4.

A mixture of (2R)-cyclic diacid above-mentioned (110 mg, 0.5 mmol) and a commercial solution of boron trifluoride-methanol complex in methanol (1.1 ml, $BF_3$ 12% w/w) was stirred at 18±5° C. for 15 hours. After careful addition of the reaction mixture at saturated sodium hydrogen carbonate solution (20 ml), the resulting aqueous layer was washed with ether (3×15 ml), acidified (pH 1) with hydrochloric acid 2N, and extracted with ether (3×15 ml). The combined organic layers were dried over magnesium sulfate and evaporated to dryness to afford a viscous yellow oil (69 mg, 59%). The product thus obtained showed identical characteristics to this obtained from method 1° above.

EXAMPLE 20

Preparation of (2S)-anhydrohomoharringtonic acid from (−)-quinyl (2'R)-anhydrohomoharringtonate resulting from Example 18)

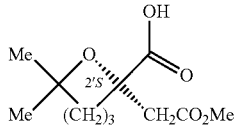

1°) Obtaining Via Hydrogenolysis

To a stirred solution of quinyl (2'S)-anhydroharringtonate (100 mg, 0.19 mmol) in ethyl acetate (11 ml) was added 10% palladium on charcoal (40 mg). The resulting mixture was stirred at room temperature under hydrogen pressure (50 p.s.i.) and after CCM control the reaction mixture was filtered and the resulting organic layer was treated with saturated sodium hydrogen carbonate solution. The aqueous layer was washed with ethyl acetate and after acidification with hydrochloric acid 1N was extracted with ethyl acetate. The combined organic layers were washed with brine, dried over magnesium sulfate and evaporated to dryness to afford a yellow solid (23 mg, 53%). The product thus obtained showed the following characteristics:

$[\alpha]_D^{20}$: +(c=0.36; $CHCl_3$)

IR (film NaCl) ($cm^{-1}$): 2975; 2951; 1740; 1718; 1439.

$^1H$ NMR 400 MHz ($CDCl_3$) (δ ppm, J Hz): $^1H$ NMR spectra of the product thus obtained was identical to this described in Example 6-1.

2°) Obtaining Via Total Saponification then Selective Methylation

A mixture of potassium hydroxide (430 mg, 7.7 mmol) in water (9 ml) was added to a stirred solution of quinyl(2'S)-anhydroharringtonate (447 g, 0.81 mmol) in ethanol (16 ml) and the resulting mixture was stirred at reflux for 24 hours. After cooling at room temperature and removal of ethanol in vacuo, the residue was treated with water (10 ml) and the resulting aqueous layer was extracted with ether (4×15 ml). After acidification (pH 1) with hydrochloric acid 2N and saturation with sodium chloride, the aqueous layer was extracted with ethyl acetate (3×15 ml). The combined organic layers were dried over magnesium sulfate and evaporated to dryness to afford a yellow solid (140 mg, 80%). The cyclic diacid thus obtained showed the following characteristics:

$[\alpha]_D^{20}$: +8 (c=0.19; $CHCl_3$)

IR (film NaCl) ($cm^{-1}$): 2975; 2945; 1717.

$^1H$ NMR 400 MHz ($CDCl_3$) (δ ppm, J Hz): $^1H$ NMR spectra of the product thus obtained was identical to this described in Example 4.

A mixture of (2S)-cyclic diacid above-mentioned (136 mg, 0.62 mmol) and a commercial solution of boron trifluoride-methanol complex in methanol (1.3 ml, $BF_3$ 12% w/w) was stirred at 18±5° C. for 15 hours. After careful addition of the reaction mixture at saturated sodium hydrogen carbonate solution (20 ml), the resulting aqueous layer was washed with ether (3×15 ml), acidified (pH 1) with hydrochloric acid 2N and extracted with ether (3×15 ml). The combined organic layers were dried over magnesium sulfate and evaporated to dryness to afford a viscous yellow oil (81 mg, 63%). The product thus obtained showed identical characteristics to this obtained from method 1° above.

EXAMPLE 21

Preparation of Anhydrohomoharringtonine, Via Esterification of Cephalotaxine with (2R)-(+)-Anhydrohomoharringtonic Acid

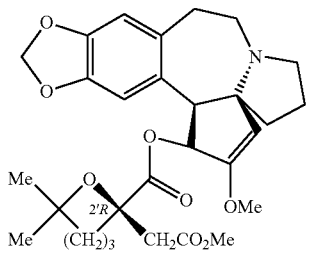

To a stirred mixture of hemiester (R) resulting from Example 19 (65 mg, 0.28 mmol) in anhydrous toluene (1 ml) at room temperature was added triethylamine (dried over potassium hydroxide) (38 μl, 0.28 mmol) and 2,4,6-trichlorobenzoyl chloride ([43 □l] *43 μl*, 0.28 mmol). After stirring at 30° C. for 1.5 hours (with control of disappearing of starting acid in infra-red), 4-dimethylaminopyridine (50 mg, 0.41 mmol) was added, the reaction mixture was allowed to react for 5 minutes and cephalotaxine (129 mg, 0.41 mmol) was added. After stirring at 30° C. for 18 hours, the reaction mixture was filtered on paper and diluted with ether (5 ml). The resulting organic layer was successively washed with water (5 ml), with saturated sodium hydrogen carbonate solution (5 ml), with water again (5 ml) then was dried over magnesium sulfate and evaporated in vacuo. The resulting crude product was purified by column chromatography (dichloromethane/methanol (99:1), silica (15-40 μm)) to provide expected product (65 mg, 43%). The product thus obtained showed following characteristics:

$^1$H NMR 400 MHz ($CDCl_3$) (δ ppm, J Hz): 6.61 (1H, s, H-17*); 6.58 (1H, s, H-14*); 5.92 (1H, d, $J_{3-4}$=9.6, H-3); 5.87 and 5.79 (2H, 2s, $OCH_2O$); 5.04 (1H, br.s, H-1); 3.80 (1H, d, $J_{4-3}$=9.2, H-4); 3.70 (3H, s, $OCH_3$); 3.59 (3H, s, $OCH_3$); 3.12 (2H, m, H-11β+H-8α); 2.95 (1H, m, H-10α); 2.60 (2H, m, H-8β+H-10β); 2.38 (1H, m, H-11α); 2.13 and 1.66 (2H, 2d, $J_{AB}$=14.3, $\underline{CH_2}CO_2$); 2.02 (1H, m, H-$6_A$); 1.90 (1H, m, H-$6_B$); 1.76 (2H, m, $CH_2$-7); 1.8-1.2 (6H, m, 3×$CH_2$); 1.10 (3H, s, $CH_3$); 1.04 (3H, s, $CH_3$).

EXAMPLE 22

Preparation of Anhydroepihomoharringtonine, Via Esterification of Cephalotaxine with (2S)-(+)-anhydrohomoharringtonic acid

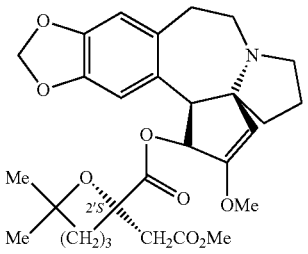

To a stirred mixture of hemiester (S) resulting from Example 20 (87 mg, 0.38 mmol) in anhydrous toluene (1.7 ml) at room temperature was added triethylamine (dried over potassium hydroxide) (52 μl, 0.38 mmol) and 2,4,6-trichlorobenzoyl chloride (57 μl, 0.38 mmol). After stirring at 30° C. for 1.5 hours (with control of disappearing of starting acid in infra-red), 4-dimethylaminopyridine (70 mg, 0.57 mmol) was added, the reaction mixture was allowed to react for 5 minutes and cephalotaxine (180 mg, 0.57 mmol) was added. After stirring at 30° C. for 18 hours, the reaction mixture was filtered on paper and diluted with ether (5 ml). The resulting organic layer was successively washed with water (5 ml), with saturated sodium hydrogen carbonate solution (5 ml), with water again (5 ml), then was dried over magnesium sulfate and evaporated in vacuo. The resulting crude product was purified by column chromatography (dichloromethane/methanol (99:1), silica (15-40 μm)) to provide expected product (101 mg, 50%). The product thus obtained showed following characteristics:

$^1$H NMR 400 MHz ($CDCl_3$) (δ ppm, J Hz): 6.61 (1H, s, H-17*); 6.57 (1H, s, H-14*); 5.84 (3H, m, H-3)+$OCH_2O$); 5.04 (1H, m, H-1); 3.78 (1H, d, $J_{4-3}$=9.7, H-4); 3.65 (3H, s, $OCH_3$); 3.59 (3H, s, $OCH_3$); 3.23 (1H, m, H-11β); 3.09 (1H, m, H-8α); 2.93 (1H, m, H-10α); 2.58 (2H, m, H-8β+H-10β); 2.39 (1H, dd, $J_{AB}$=14.4, J=7.0, H-11α); 2.16 and 1.83 (2H, 2d, $J_{AB}$=14.5, $\underline{CH_2}CO_2$); 2.06 (1H, m, H-$6_A$); 1.88 (1H, m, H-$6_B$); 1.74 (2H, m, $CH_2$-7); 1.5-1.2 (6H, m, 3×$CH_2$); 1.11 (3H, s, $CH_3$); 1.02 (3H, s, $CH_3$).

EXAMPLE 23

Preparation of 6'-bromo-6'-desoxy-homoharringtonine, from anhydro-homoharringtonine resulting from Example

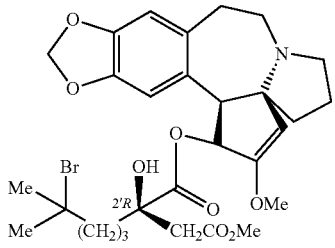

To a stirred solution of product resulting from Example 21 (60 mg, 0.114 mmol) in anhydrous dichloromethane (300 μl) was added at −10° C. a commercial solution of hydrobromic acid in acetic acid (205 μl, 1.02 mmol, HBr 30% w/w). After stirring at −10° C. for 3 hours, was added saturated sodium hydrogen carbonate solution up to pH 8. The resulting aqueous layer was extracted three times with dichloromethane and the combined organic layers were dried over magnesium sulfate and evaporated to dryness to afford a yellow oil (60 mg, 87%). The crude product thus obtained showed the following characteristics:

IR (ATR) ($cm^{-1}$): 2957; 1744; 1653; 1487; 1223.

$^1$H NMR 400 MHz ($CDCl_3$) (δ ppm, J Hz): 6.63 (1H, s, H-17*); 6.54 (1H, s, H-14*); 5.99 (1H, d, $J_{3-4}$=9.8, H-3); 5.87 (2H, m, $OCH_2O$); 5.05 (1H, s, H-1); 3.78 (1H, d, $J_{4-3}$=9.8, H-4); 3.69 (3H, s, $OCH_3$); 3.58 (3H, s, $OCH_3$); 3.54 (1H, s, 2'-OH); 3.10 (2H, m, H-11β+H-8α); 2.94 (1H, m, H-10α); 2.60 (2H, m, H-8β+H-10β); 2.39 (1H, dd, $J_{AB}$=14.0, J=6.8, H-11α); 2.26 and 1.89 (2H, 2d, $J_{AB}$=16.5, $\underline{CH_2}CO_2$); 2.03 (1H, m, H-$6_A$); 1.91 (1H, m, H-$6_B$); 1.75 (2H, m, $CH_2$-7); 1.74 (3H, s, $CH_3$); 1.72 (3H, s, $CH_3$); 1.6-1.2 (6H, m, 3×$CH_2$).

EXAMPLE 24

Preparation of 6'-bromo-6'-desoxy-epihomoharringtonine, from anhydro-epihomoharringtonine resulting from Example 22

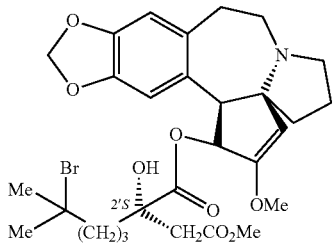

A commercial solution of hydrobromic acid in acetic acid (205 μl, 1.02 mmol, HBr 30% w/w) was added to a stirred solution of product resulting from Example 22 (60 mg, 0.114 mmol) in anhydrous dichloromethane (300 μl) at −10° C.

After stirring at −10° C. for 3 hours, was added a saturated sodium hydrogen carbonate solution up to pH 8 and the resulting aqueous layer was extracted three times with dichloromethane. The combined organic layers were dried over magnesium sulfate and evaporated to dryness to afford a yellow oil (63 mg, 91%). The crude product thus obtained showed the following characteristics:

IR (ATR) ($cm^{-1}$): 2957; 1744; 1653; 1487; 1223.

$^1$H NMR 400 MHz ($CDCl_3$) (δ ppm, J Hz): 6.64 (1H, s, H-17*); 6.59 (1H, s, H-14*); 5.97 and 5.87 (2H, 2d, $J_{AB}$=1.1, $OCH_2O$); 5.95 (1H, d, $J_{3-4}$=9.7, H-3); 5.04 (1H, s, H-1); 3.78 (1H, d, $J_{4-3}$=9.7, H-4); 3.67 (3H, s, $OCH_3$); 3.66 (3H, s, $OCH_3$); 3.49 (1H, s, 2'-OH); 3.10 (2H, m, H-11β+H-8α); 2.93 (1H, m, H-10α); 2.62 and 2.54 (2H, 2d, $J_{AB}$=16.5, $\underline{CH_2}CO_2$); 2.60 (2H, m, H-8β+H-10β); 2.40 (1H, m, H-11α); 2.03 (1H, m, H-$6_A$); 1.89 (1H, m, H-$6_B$); 1.74 (2H, m, $CH_2$-7); 1.72 (3H, s, $CH_3$); 1.70 (3H, s, $CH_3$); 1.6-0.7 (6H, m, 3×$CH_2$).

EXAMPLE 25

Preparation of homoharringtonine, from 6'-bromo-6'-desoxy-homoharringtonine resulting from Example 23

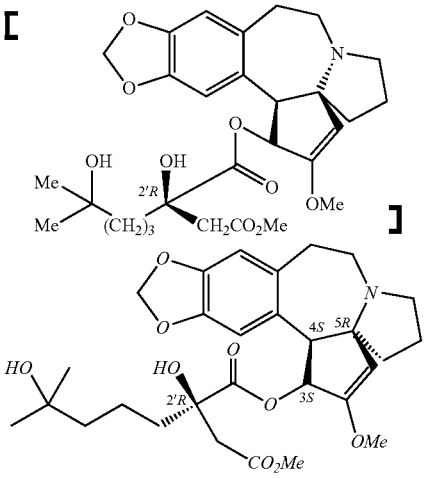

1) Method A:

A 5% sodium hydrogen carbonate solution (3 ml) was added to a stirred solution of product resulting from Example 23 (60 mg, 0.099 mmol) in acetone (1.5 ml). After stirring at room temperature for 2 hours, the reaction mixture was evaporated in vacuo and the residual aqueous layer was extracted three times with dichloromethane. The combined organic layers were dried over magnesium sulfate and evaporated to dryness. The resulting crude product (55 mg) was purified by column chromatography (dichloromethane, then dichloromethane/methanol (99:1 then 95:5), silica (15-40 μm) 2.75 g) to provide homoharringtonine (29 mg, 47%). The product thus obtained showed following characteristics:

$[\alpha]_D^{20}$: −110 (c=0.24; $CHCl_3$)

IR(film NaCl) ($cm^{-1}$): 3468; 2961; 1745; 1656; 1487; 1224; 1033.

$^1$H NMR 400 MHz ($CDCl_3$) (δ ppm, J Hz): 6.63 (1H, s, H-17*); 6.55 (1H, s, H-14*); 6.01 (1H, d, $J_{3-4}$=9.8, H-3); 5.87 (2H, m, $OCH_2O$); 5.05 (1H, s, H-1); 3.78 (1H, d, $J_{4-3}$=9.8, H-4); 3.68 (3H, s, $OCH_3$); 3.58 (3H, s, $OCH_3$); 3.54 (1H, s, 2'-OH); 3.10 (2H, m, H-11β+H-8α); 2.95 (1H, m, H-10α); 2.59 (2H, m, H-8β+H-10β); 2.38 (1H, dd, $J_{AB}$=14.0, J=6.7, H-11α); 2.27 and 1.90 (2H, 2d, $J_{AB}$=16.5, $\underline{CH_2}CO_2$); 2.02 (1H, m, H-$6_A$); 1.90 (1H, m, H-$6_B$); 1.76 (2H, m, $CH_2$-7); 1.5-1.15 (6H, m, 3×$CH_2$); 1.30 (1H, s, 6'-OH); 1.19 (6H, 2s, 2×$CH_3$).

2) Method B:

A saturated calcium carbonate solution (3 ml) was added to a stirred solution of product resulting from Example 23 (60 mg, 0.099 mmol) in acetone (3 ml). After stirring at room temperature for 2 hours, obtaining of product resulting from method A was specified by CCM.

3) Method C:

A saturated barium carbonate solution (9 ml) was added to a stirred solution of product resulting from Example 23 (60 mg, 0.099 mmol) in acetone (3 ml). After stirring at room temperature for 2 hours, obtaining of product resulting from method A was specified by CCM.

4) Method D:

To a stirred solution of product resulting from Example 23 (60 mg, 0.099 mmol) in a mixture acetone/water (3/2, 2.15 ml) was added silver nitrate (25 mg, 0.149 mmol). After stirring at room temperature for 2 hours, obtaining of product resulting from method A was specified by CCM.

EXAMPLE 26

Preparation of [Epihomoharringtonine] *2'-epi-homoharringtonine* (*2'-epi HHT*)

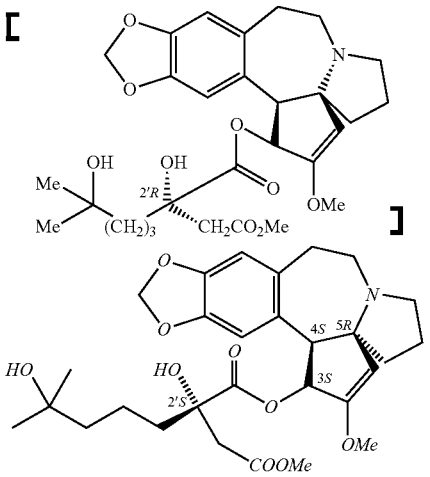

1°) from 6'-bromo-6'-desoxy-epihomoharringtonine resulting from Example 24:

a) Method A:

A 5% sodium hydrogen carbonate solution (3 ml) was added to a stirred solution of product resulting from Example 24 (60 mg, 0.099 mmol) in acetone (1.75 ml). After stirring at room temperature for 2 hours, the reaction mixture was evaporated in vacuo and the residual aqueous layer was extracted three times with dichloromethane. The combined organic layers were dried over magnesium sulfate and evaporated to dryness. The resulting crude product (60 mg) was purified by column chromatography (dichloromethane, then dichloromethane/methanol (99:1 then 97:3), silica (15-40 μm) 3 g) to provide epihomoharringtonine (29 mg, 47%). The product thus obtained showed following characteristics:

$[\alpha]_D^{20}$: −92 (c=0.29; $CHCl_3$)

IR (film NaCl) ($cm^{-1}$): 3514; 2961; 1744; 1655; 1488; 1223; 1035. $^1H$ NMR 400 MHz ($CDCl_3$) (δ ppm, J Hz): 6.65 (1H, s, H-17*); 6.60 (1H, s, H-14*); 5.95 (1H, d, H-3); 5.95 and 5.86 (2H, 2d, $OCH_2O$); 5.05 (1H, s, H-1); 3.78 (1H, d, $J_{4-3}$=9.7, H-4); 3.68 (3H, s, $OCH_3$); 3.66 (3H, s, $OCH_3$); 3.52 (1H, br.s, 2'-OH); 3.13 (2H, m, H-11β+H-8α); 2.97 (1H, m, H-10α); 2.63 (2H, m, H-8β+H-10β) 2.61 and 2.52 (2H, 2d, $J_{AB}$=16.5, $\underline{CH_2}CO_2$); 2.40 (1H, dd, $J_{AB}$=13.8, J=6.3, [H-11□] *H-11*α); 2.04 (1H, m, H-$6_A$); 1.94 (1H, m, H-$6_B$); 1.78 (2H, m, $CH_2$-7); 1.45-0.7 (6H, m, 3×$CH_2$); 1.16 (3H, s, $CH_3$); 1.15 (3H, s, $CH_3$).

b) Method B:

A saturated calcium carbonate solution (3 ml) was added to a stirred solution of product resulting from Example 24 (60 mg, 0.099 mmol) in acetone (3 ml). After stirring at room temperature for 2 hours, obtaining of product resulting from method A was specified by CCM.

c) Method C:

A saturated barium carbonate solution (9 ml) was added to a stirred solution of product resulting from Example 24 (60 mg, 0.099 mmol) in acetone (3 ml). After stirring at room temperature for 2 hours, obtaining of product resulting from method A was specified by CCM.

d) Method D:

To a stirred solution of product resulting from Example 24 (60 mg, 0.099 mmol) in a mixture acetone/water (3/2, 2.15 ml) was added silver nitrate (25 mg, 0.149 mmol). After stirring at room temperature for 2 hours, obtaining of product resulting from method A was specified by CCM.

2°) from Anhydroepihomoharringtonine Resulting from Example 22

To a stirred solution of anhydroepihomoharringtonine resulting from Example 22 (58 mg, 0.109 mmol) in anhydrous dichloromethane (0.3 ml) was added at −10° C. a commercial solution of hydrobromic acid in acetic acid (0.195 ml, 0.98 mmol, HBr 30% w/w). After stirring at −10° C. for 3 hours, was added water (2.8 ml) and then the temperature was raised to 20° C. After stirring at 20° C. for 3 hours, was added a sodium carbonate solution (0.76M; 6 ml) up to pH 8. The resulting aqueous layer, after saturation with sodium chloride, was extracted with dichloromethane (3×10 ml) and the combined organic layers were dried over magnesium sulfate and evaporated to dryness to provide epihomoharringtonine (45 mg brut, 75%). The crude product thus obtained showed identical characteristics to this obtained with method A.

EXAMPLE 27

Preparation of Homoharringtonine as a Pharmaceutical Use from Crude Semi-Synthetic Homoharringtonine Resulting from Example 25 by Preparative High-Performance Liquid Chromatography

[ 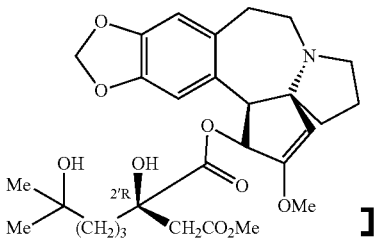

]

-continued

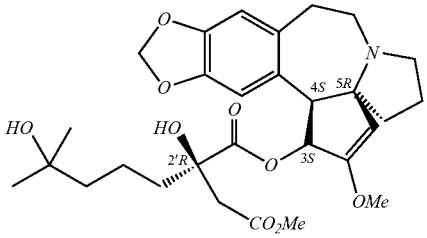

homoharringtonine *or cephalotaxine, 4-methyl (2R)-2-hydroxy-2-(4-hydroxy-4-methylpentyl) butanedioate (ester)*

[ 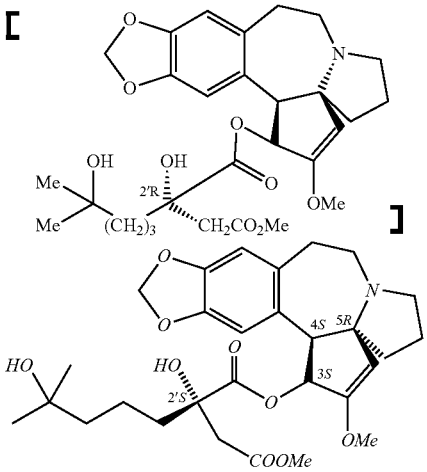

]

[epi-homoharrintonine] *2'-epi-homoharringtonine or 2'-epi-HHT*

1°) Method A

Crude homoharringtonine (35 g) is dissolved in buffer (triethylamine (1.55/1000) in deionised water and orthophosphoric acid to adjust pH to 3. The solution was filtered then injected on a preparative high-performance liquid chromatograph equipped with axial compression and high pressure pump (stationary phase: n-octadecylsilane, 15 μm, porosity 100, 1 kg; mobile phase: buffer/tetrahydrofurane 85/15). Elution was performed at a flow rate of 0.2 l/min. Fractions contain was monitored by U.V. detector and TLC. Retained fraction were finally checked by HPLC then combined, alkalinised with 2.5% aqueous ammonia and extracted with dichloromethane (4×400 ml), After concentration under reduced pressure homoharringtonine is obtained as a pale yellow resin which on trituration in a 8/2 water-methanol mixture gave pure homoharringtonine as a white crystalline solid (mp=127° C.), HPLC purity was higher than 99.8%.

2°) Method B

Same procedure of purification as method A was performed but mobile phase buffer/methanol (68/32) was used instead buffer/tetrahydrofurane.

3°) Method C

Same procedure of purification as method A was performed but mobile phase buffer/acetonitrile (85/15) was used instead buffer/tetrahydrofurane.

EXAMPLE 28

Preparation of Homoharringtonine as a Pharmaceutical Use from Semi-Purified Natural Cephalotaxine Crude homoharringtonine, prepared according to Example 25 from a partially racemized natural cephalotaxine and purified by chromatography and crystallisation according to the method A of Example 27, gave an homoharringtonine showing a non natural enantiomeric epi-homoharringtonine content less than 0.05%.

EXAMPLE 29

Preparation of 2'-de-(methoxycarbonylmethyl)-(2-O-3')-dehydroneoharringtonine or cephalotaxyl phenylglycidate, via esterification of cephalotaxine with phenylglycidic acid

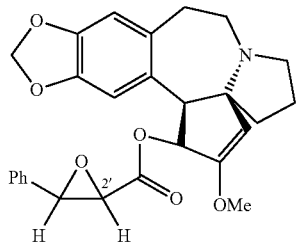

To a stirred mixture of (2R,3R)-cis-phenylglicidic acid (78 mg, 0.48 mmol) in anhydrous toluene (2 ml) was added 1,3-dicyclohexylcarbodiimide (130 mg, 0.63 mmol). After stirring for 10 minutes at room temperature, cephalotaxine (50 mg, 0.16 mmol) and pyrrolidinopyridine (24 mg, 0.16 mmol) were added. After stirring at 18±5° C. for 15 hours (with control of reaction in CCM, eluant dichloromethane/methanol; 8:2), the reaction mixture was filtered on ground-glass filter, the cake was washed with toluene (5 ml) and the filtrate was evaporated in vacuo. The resulting crude product (200 mg) was purified by column chromatography (dichloromethane/methanol (98:2), silica (15-40 μm) 4 g) to provide expected product (19 mg, 27%). The product thus obtained showed following characteristics:

$^1$H NMR 400 MHz ($CDCl_3$) (δ ppm, J Hz): 7.27 (3H, m, Ph); 7.18 (2H, m, Ph); 6.63 (1H, s, H-17*); 6.40 (1H, s, H-14*); 5.96 and 5.85 (2H, 2d, $J_{AB}$=1.5, $OCH_2O$); 5.73 (1H, d, $J_{3-4}$=9.4, H-3); 5.01 (1H, s, H-1); 4.01 (1H, d, $J_{3'-2'}$=4.6, H-3'); 3.65 (3H, s, $OCH_3$); 3.62 (1H, d, $J_{4-3}$=9.3, H-4); 3.40 (1H, d, $J_{2'-3'}$=4.5, H-2'); 3.27 (1H, m, $J_{AB}$=14.3, J=12.1 and 7.8, H-11β); 3.05 (1H, m, H-8α); 2.91 (1H, td, J=11.7 and 7.4, H-10α); 2.57 (2H, m, H-8β+H-10β); 2.43 (1H, dd, $J_{AB}$=14.5, J=7.0, H-11α); 1.93 (1H, m, H-$6_A$); 1.84 (1H, m, H-$6_B$); 1.68 (2H, m, $CH_2$-7).

EXAMPLE 30

Preparation of 2'-de-(methoxycarbonylmethyl)-neoharringtonine, via hydrosenolysis of cephalotaxyl phenylglycidate resulting from Example 29

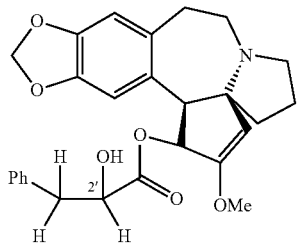

To a stirred solution of cephalotaxyl phenylglicidate resulting from Example 29 (200 mg, 0.433 mmol) in methanol (10 ml) was added 10% palladium on charcoal (100 mg). The resulting mixture was stirred at room temperature under hydrogen pressure (50 p.s.i.) for 4 hours, and the reaction mixture was filtered and evaporated to dryness. The resulting crude product (175 mg) was purified by column chromatography (dichloromethane/methanol (99:1 then 98:2), silica (15-40 μm) 5.5 g) to provide an amber solid (86 mg, 43%). The product thus obtained showed following characteristics:

IR (pastille KBr) ($cm^{-1}$): 3436; 2937; 1747; 1655; 1487; 1224 et 1035.

$^1$H NMR 400 MHz ($CDCl_3$) (δ ppm, J Hz): 7.25 (3H, m, m, p-Ph); 7.0 (2H, m, o-Ph); 6.65 (1H, s, H-17*); 6.63 (1H, s, H-14*); 5.98 (1H, d, $J_{3-4}$=9.3, H-3); 5.85 (2H, 2d, $J_{AB}$=1.2, $OCH_2O$); 5.09 (1H, s, H-1); 4.17 (1H, m, H-2'); 3.85 (1H, d, $J_{4-3}$=9.6, H-4); 3.71 (3H, s, $OCH_3$); 3.20 (1H, m, H-11β); 3.10 (1H, m, H-8α); 2.95 (1H, m, H-10α); 2.60 (2H, m, H-8α+H-10β); 2.39 (2H, m, H-11α+H-$3'_A$); 2.04 (1H, m, H-$6_A$); 2.0 (1H, dd, $J_{AB}$=14.3, $J_{3'B-2'}$=9.5, H-3'B); 1.91 (1H, m, H-$6_B$) 1.77 (2H, m, $CH_2$-7).

EXAMPLE 31

Preparation of 2'R-de-(methoxycarbonylmethyl)-3'S-azido-neoharringtonine, from cephalotaxyl phenylglycidate resulting from Example 29

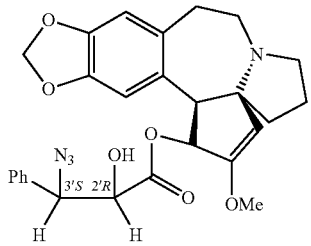

To a stirred solution of cephalotaxyl phenylglicidate resulting from Example 29 (100 mg, 0.217 mmol) in a mixture of methanol/water (8/1, 1.27 ml) was added sodium azide (70 mg, 1.08 mmol) and methyl formate (174 μl, 2.82 mmol). After stirring at 50° C. for 68 hours, and cooling at ambient temperature, was added 5% sodium hydrogen carbonate solution up to pH 8. The resulting aqueous layer was extracted three times with dichloromethane and the combined organic layers were dried over magnesium sulfate and evaporated to dryness. The resulting crude product (120 mg) was purified by column chromatography (dichloromethane/methanol (99:1), silica (15-40 μm) 3.5 g) to provide a viscous yellow oil (84 mg, 76%). The product thus obtained showed following characteristics:

IR (ATR) ($cm^{-1}$): 3488; 2935; 2105; 1748; 1654; 1486; 1223; 1034.

$^1$H NMR 400 MHz ($CDCl_3$) (δ ppm, J Hz): 7.38 (3H, m, m, p-Ph); 7.29 (2H, m, o-Ph); 6.74 (1H, s, H-17*); 6.67 (1H, s, H-14*); 6.08 (1H, d, $J_{3-4}$=9.8, H-3); 5.90 (2H, 2d, $J_{AB}$=1.4, $OCH_2O$); 5.08 (1H, s, H-1); 4.07 (1H, d large, H-2'); 3.85 (1H, d, $J_{4-3}$=9.7, H-4); 3.78 (1H, br.s, H-3'); 3.69 (3H, s, $OCH_3$); 3.23 (1H, m, H-11β): 3.11 (1H, m, H-8α); 2.98 (1H, m, H-10α); 2.90 (1H, d, $J_{2'-OH}$=8.2, 2'-OH); 2.63 (2H, m, H-8β+H-10β); 2.47 (1H, dd, $J_{AB}$=14.2, J=6.9, H-11α); 2.05 (1H, m, H-$6_A$); 1.92 (1H, m, H-$6_B$); 1.78 (2H, m, $CH_2$-7).

EXAMPLE 32

Preparation of 2'R-de(methoxycarbonylmethyl)-3'S-amino-neoharringtonine, via hydrogenolysis of azide resulting from Example 31

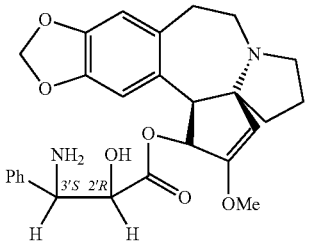

To a stirred solution of product resulting from Example 29 (80 mg, 0.158 mmol) in a mixture ethyl acetate-methanol (9/1, 10 ml) was added 10% palladium on charcoal (40 mg). The resulting mixture was stirred at room temperature under hydrogen pressure (50 p.s.i.) for 15 hours and after CCM control the reaction mixture was filtered and evaporated to dryness to provide a white solid (67 mg, 88%). The crude product thus obtained showed following characteristics:

IR (ATR) ($cm^{-1}$): 3299; 2935; 1740; 1654; 1486; 1222 et 1034.

$^1$H NMR 400 MHz ($CDCl_3$) (δ ppm, J Hz): 7.27 (5H, m, Ph); 6.69 (1H, s, H-17*); 6.67 (1H, s, H-14*); 6.0 (1H, d, $J_{3-4}$=9.7, H-3); 5.85 (2H, m, $OCH_2O$); 5.09 (1H, br.s, H-1); 4.01 (1H, d, J=1.2, H-2'); 3.86 (1H, d, $J_{4-3}$=9.5, H-4); 3.72 (3H, s, $OCH_3$); 3.38 (1H, br.s); 3.25 (1H, m, H-11β); 3.14 (1H, m, H-8α); 2.99 (1H, m, H-10α); 2.64 (2H, m, H-8β+H-10β); 2.49 (1H, m, H-11α); 2.05 (1H, m, H-$6_A$); 1.94 (1H, m, H-$6_B$); 1.79 (2H, m, $CH_2$-7).

EXAMPLE 33

Preparation of acetonide of 2'-de-(methoxycarbonylmethyl)-3'-hydroxy-neoharringtonine, via esterification of cephalotaxine

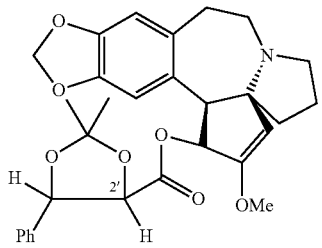

To a stirred mixture of isopropylidene-2,3-dihydroxy-3-phenylpropionic acid (17.5 mg, 0.078 mmol) in anhydrous toluene (1 ml) was added 1,3-dicyclohexylcarbodiimide (25 mg, 0.12 mmol). After stirring for 10 minutes at room temperature, cephalotaxine (75 mg, 0.24 mmol) and pyrrolidinopyridine (12 mg, 0.08 mmol) were added, After stirring at 18±5° C. for 15 hours (with control of reaction in CCM, eluant dichloromethane/methanol; 8:2), the reaction mixture was filtered on ground-glass filter, the cake was washed with toluene (5 ml) and the filtrate was evaporated in vacuo. The resulting crude product was purified by column chromatography (dichloromethane, then dichloromethane/methanol (98:2), silica (15-40 μm)) to provide expected product (22 mg, 53%). The product thus obtained showed following characteristics:

$^1$H NMR 400 MHz ($CDCl_3$) (δ ppm, J Hz): 7.27 (5H, Ph); 6.63, 6.62, 6.60 and 6.57 (1H, 4s, H-14*); 6.51, 6.49, 6.42 and 6.41 (1H, 4s, H-17*); 5.93 ($J_{3-4}$=9.6), 5.89, 5.43 ($J_{3-4}$=9.5) and 5.31 ($J_{3-4}$=9.3 (1H, 4d, H-3); 5.89 (s), 5.87+5.84 (2d, $J_{AB}$=1.5), 5.85+5.80 (2d) and 5.84+5.77 (2d, $J_{AB}$=1.5) (2H, $OCH_2O$); 5.23 ($J_{5'-4'}$=7.3), 5.20 ($J_{5'-4'}$=7.4), 4.58 ($J_{5'-4'}$=8.0) and 4.49 ($J_{5=-4'}$=6.2) (1H, 4d, H-5'); 5.07, 5.03 and 4.83 (1H, 3s, H-1); 4.32 ($J_{4'-5'}$=7.4), 4.21 ($J_{4'-5'}$=6.2), 4.18 ($J_{4'-5'}$=7.4) and 3.75 (1H, 4d, H-4'); 3.86 ($J_{4-3}$=9.6), 3.76 and 3.60 ($J_{4-3}$=9.5) (1H, 4d, H-4); 3.76, 3.75, 3.70 and 3.43 (3H, 4s, $OCH_3$); 3.3-1.6 (10H, m); 1.66+1.41, 1.65+1.37, 1.51+1.44 and 1.47+1.22 (6H, 8s, 2×$CH_3$).

EXAMPLE 34

Preparation of cephalotaxyl N-benzyl-3-phenyl-aziridine-1-carboxylate via esterification of cephalotaxine

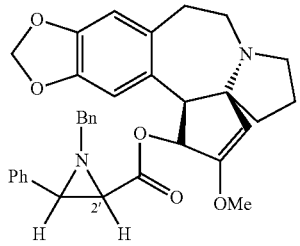

To a stirred mixture of (2S,3S)-cis-N-benzyl-3-phenylaziridine-1-carboxylic acid (360 mg, 1.42 mmol) in anhydrous toluene (5 ml) was added 1,3-dicyclohexylcarbodiimide (390 mg, 1.9 mmol). After stirring for 5 minutes at room temperature, cephalotaxine (150 mg 0.47 mmol) and pyrrolidinopyridine (70 mg, 0.47 mmol) were added. After stirring at 18±5° C. for 2 hours (with control of reaction in CCM, eluant dichloromethane/methanol; 8:2), the reaction mixture was filtered on ground-glass filter, the cake was washed with toluene (15 ml) and the filtrate was evaporated in vacuo. The resulting crude product (785 mg) was purified by column chromatography (dichloromethane, then dichloromethane/methanol (98:2), silica (15-40 μm) 23 g) to provide a solid (240 mg, 92%). The product thus obtained showed following characteristics:

$^1$H NMR 400 MHz ($CDCl_3$) (δ ppm, J Hz): 7.24 (10H, m, 2×Ph); 6.63 (1H, s, H-17*); 6.60 (1H, s, H-14*); 5.85 and 5.80 (2H, 2d, $J_{AB}$=1.4, $OCH_2O$); 5.64 (1H, d, $J_{3-4}$=9.3, H-3); 4.97 (1H, s, H-1); 3.92 and 3.20 (2H, 2d, $J_{AB}$=13.7, $\underline{CH_2}$Ph); 3.71 (1H, d, $J_{4-3}$=9.4, H-4); 3.56 (3H, s, $OCH_3$); 3.25 (1H, m, H-11β); 3.07 (1H, m, H-8α); 2.93 (1H, m, H-10α); 2.86 (1H, d, $J_{3'-2'}$=6.8, H-3'); 2.57 (2H, m, H-8β+H-10β); 2.38 (1H, dd, $J_{AB}$=14.4, J=7.0, H-11α); 2.07 (1H, d, $J_{2'-3'}$=6.8, H-2'); 1.96 (1H, m, H-$6_A$); 1.82 (1H, m, H-$6_B$); 1.70 (2H, m, $CH_2$-7).

EXAMPLE 35

Preparation of N,O-anhydro-2'-de-(methoxycarbonylmethyl)-3'-benzamidoneo-harringtonine or cephalotaxyl N,O-anhydro-N-benzoyl-phenylisoserinate via esterification of cephalotaxine

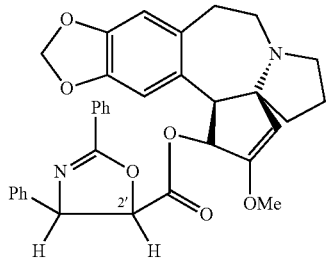

To a stirred mixture of (4S,5R)-2,4-diphenyl-4,5-dihydrooxazole-5-carboxylic acid (510 mg, 1.91 mmol) in anhydrous toluene (7 ml) was added 1,3-dicyclohexylcarbodiimide (525 mg, 2.54 mmol). After stirring for 15 minutes at room temperature, cephalotaxine (200 mg, 0.63 mmol) and pyrrolidinopyridine (95 mg, 0.64 mmol) were added. After stirring at 18±5° C. for 3.5 hours (with control of reaction in CCM, eluant dichloromethane/methanol; 9:1), the reaction mixture was filtered on ground-glass filter, the cake was washed with toluene (15 ml) and the filtrate was evaporated in vacuo. The resulting crude product (1 g) was purified by column chromatography (dichloromethane, then dichloromethane/methanol (98:2), silica (15-40 μm)) to provide a yellow solid (330 mg, 91%). The product thus obtained showed following characteristics:

$^1$H NMR 400 MHz ($CDCl_3$) (δ ppm, J Hz): 8.0 (2H, d, J=7.3, o-PhC═N); 7.52 (1H, t, J=7.4, p-PhC═N); 7.44 (2H, t, J=7.5, m-PhC═N); 7.32 (2H, t, J=7.2, m-Ph); 7.26 (1H, m, p-Ph); 7.15 (2H, d, J=7.1, o-Ph); 6.58 (1H, s, H-17*); 6.51 (1H, s, H-14*); 5.98 (1H, d, $J_{3-4}$=9.5, H-3); 5.85 and 5.76 (2H, 2d, $J_{AB}$=1.3, $OCH_2O$); 5.08 (1H, s, H-1); 4.67 (1H, d, $J_{4'5'}$=5.6, H-4'); 4.52 (1H, d, $J_{5'-4'}$=5.6, H-5') 3.85 (1H, d, $J_{4-3}$=9.6, H-4); 3.70 (3H, s, $OCH_3$); 3.17 (1H, m, H-11β); 3.08 (1H, m, H-8α); 2.93 (1H, m, H-10α); 2.59 (2H, m, H-8β+H-10β); 2.31 (1H, dd, $J_{AB}$=14.2, J=6.8, H-11α); 2.04 (1H, m, H-$6_A$); 1.91 (1H, m, H-$6_B$); 1.75 (2H, m, $CH_2$-7).

EXAMPLE 36

Preparation of N,O-methoxymethylene-2'-de-(methoxycarbonylmethyl)-3'-benz-amidoneoharringtonine or cephalotaxyl N,O-methoxymethylene-N-benzoylphenylisoserinate via esterification of cephalotaxine

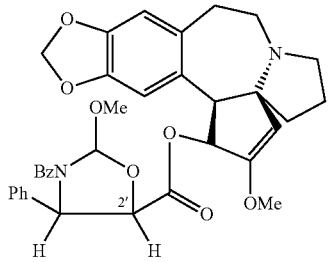

To a stirred mixture of (4S,5R)-3-N-benzoyl-2p-methoxyphenyl-4-phenyloxazolidine-5-carboxylic acid (165 mg, 0.5 mmol) in anhydrous toluene (2 ml) was added 1,3-dicyclohexylcarbodiimide (140 mg, 0.68 mmol). After stirring for 5 minutes at room temperature, cephalotaxine (53 mg, 0.17 mmol) and pyrrolidinopyridine (25 mg, 0.17 mmol) were added. After stirring at 18±5° C. for 15 hours (with control of reaction in CCM, eluant dichloromethane/methanol; 9:1), the reaction mixture was filtered on ground-glass filter, the cake was washed with toluene (5 ml) and the filtrate was evaporated in vacuo. The resulting crude product (230 mg) was purified by column chromatography (dichloromethane, then dichloromethane/methanol (98:2), silica (15-40 μm) 7 g) to provide expected product (90 mg, 86%). The product thus obtained showed following characteristics:

$^1$H NMR 400 MHz ($CDCl_3$) (δ ppm, J Hz): 7.66 (2H, br.s, o-BzN); 7.41 (4H, m, BzN+Ph); 7.32 (2H, m, Ph); 7.26 (2H, m, Ph); 6.56 (1H, s, H-17*); 6.54 (1H, s, H-14*); 5.89 (1H, d, $J_{3-4}$=9.5, H-3); 5.83 and 5.80 (2H, 2m, $OCH_2O$); 5.76 (1H, br.s, H-2'); 5.10 (1H, s, H-1); 4.85 (1H, br.s, H-4'); 4.42 (1H, br.s, H-5'); 3.84 (1H, d, $J_{4-3}$=9.5, H-4); 3.72 (3H, s, $OCH_3$); 3.28 (3H, br.s, 2'-$OCH_3$); 3.19 (1H, m, H-11β); 3.09 (1H, m, H-8α); 2.93 (1H, m, H-10α); 2.60 (2H, m, H-8β+H-10β); 2.37 (1H, dd, $J_{AB}$=14.4, J=6.6, H-11α); 2.03 (1H, m, H-$6_A$); 1.90 (1H, m, $J_{AB}$=12.2, J=7.8 and 4.4, H-$6_B$); 1.76 (2H, m, $CH_2$-7).

EXAMPLE 37

Preparation of 2'-de-(methoxycarbonylmethyl)-3'-benzamido-neoharringtonine or cephalotaxyl N-benzoyl-phenylisoserinate

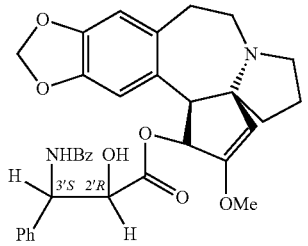

1°) Via Acidic Hydrolysis of Product Resulting from Example 35

To a stirred solution of cephalotaxyl (4S,5R)-2,4-diphenyl-4,5-dihydrooxazole-5-carboxylate resulting from Example 35 (300 mg, 0.53 mmol) in a mixture of methanol/tetrahydrofurane 50/50 (10 ml) was added at room temperature hydrochloric acid 1N (3.2 ml). After stirring at 18±5° C. for 3 hours (with control of reaction in CCM), a saturated sodium hydrogen carbonate solution (19 ml) and a mixture of methanol/tetrahydrofurane 50/50 (50 ml) were added. After stirring at 18±5° C. for 20 hours (with control of reaction in CCM), the reaction mixture was treated with ethyl acetate and water. The resulting aqueous layer was extracted with ethyl acetate and the combined organic layers were dried over magnesium sulfate and evaporated to dryness. The resulting crude product (170 mg) was purified by column chromatography (dichloromethane/methanol (98:2), silica (15-40 μm) 8 g) to provide a white solid (180 mg, 58%; HPLC purity 92.3%). The product thus obtained showed the following characteristics:

$[\alpha]_D^{20}$: −119.2 (c=0.141; $CHCl_3$)

$^1$H NMR 400 MHz ($CDCl_3$) (δ ppm, J Hz): 7.75 (2H, d, J=7.3, o-BzN); 7.51 (1H, t, J=7.3, p-BzN); 7.13 (2H, t, J=7.3, m-BzN); Ph); 7.27 (5H, m, Ph); 6.88 (1H, d, $J_{3'-NH}$=7.9, 3'-NH); 6.59 (1H, s, H-17*); 6.57 (1H, s, H-14*); 5.93 (1H, d, $J_{3-4}$=9.7, H-3); 5.78 and 5.69 (2H, 2d, JAB=1.5, $OCH_2O$); 5.06 (1H, s, H-1); 4.98 (1H, dd, $J_{3'-NH}$=7.9, H-3'); 4.22 (1H, br.s, H-2'); 3.81 (1H, d, $J_{4-3}$=9.6, H-4); 3.58 (3H, s, $OCH_3$); 3.19 (1H, m, J=12.8, 7.9, H-11b); 3.07 (1H, m, H-8a); 2.93 (1H, m, H-10a); 2.72 (1H, br.s, 2'-OH), 2.58 (2H, m, H-8b+H-10b); 2.43 (1H, dd, $J_{AB}$=14.2, J=7.0, H-11a); 2.01 (1H, m, H-$6_A$); 1.88 (1H, m, $J_{AB}$=12.0, J=7.8, 3.8, H-$6_B$); 1.75 (2H, m, $CH_2$-7)

2°) Via Amidification of Product Resulting from Example 32

To a stirred solution of product resulting from Example 32 (60 mg, 0.125 mmol) in ethyl acetate (850 μl ) were added a saturated sodium hydrogen carbonate solution (850 μl) and benzoyl chloride (19 μl, 0.163 mmol). A white precipitate was formed during the course of reaction. After stirring at room temperature for 1 hour, the reaction mixture was diluted with ethyl acetate and the organic layer was washed with a saturated sodium hydrogen carbonate solution. The resulting aqueous layer was extracted three times with ethyl acetate and the combined organic layers were dried over magnesium sulfate and evaporated to dryness. The resulting crude product (65 mg) was purified by column chromatography (dichloromethane/methanol (98:2), silica (15-40 μm) 2.5 g) to provide a white solid (41 mg, 56%). The product thus obtained showed identical characteristics to this obtained from method above-mentioned.

EXAMPLE 38

Preparation of N-terbutoxycarbamoyl-2'-de-(methoxycarbonylmethyl)-3'-amino-neoharringtonine or cephalotaxyl N-terbutoxycarbamoyl-phenylisoserinate via amidification of product resulting from Example 32

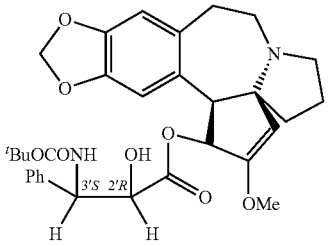

To a stirred solution of product resulting from Example 32 (60 mg, 0.125 mmol) in dichloromethane (850 μl) were added a saturated sodium hydrogen carbonate solution (850 μl) and diterbutyldicarbonate (27 mg, 0.125 mmol). After stirring at room temperature for 1 hour, the reaction mixture was diluted with dichloromethane and the organic layer was washed with brine. The resulting aqueous layer was extracted three times with dichloromethane and the combined organic layers were dried over magnesium sulfate and evaporated to dryness. The resulting crude product (70 mg) was purified by column chromatography (dichloromethane/methanol (98:2), silica (15-40 μm) 3 g) to provide a white solid (40 mg, 55%). The product thus obtained showed the following characteristics:

$^1$H NMR 400 MHz ($CDCl_3$) (δ ppm, J Hz): 7.27 (3H, m, m, p-Ph); 6.94 (2H, d, J=6.6, o-Ph); 6.71 (1H, s, H-17*); 6.66 (1H, s, H-14*); 6.01 (1H, d, $J_{3-4}$=9.7, H-3); 5.90 (2H, s, $OCH_2O$); 5.06 (1H, s, H-1); 5.05 (1H, m, NH); 4.56 (1H, m, H-3'); 4.15 (1H, m, H-2'); 3.81 (1H, d, $J_{4-3}$=9.7, H-4); 3.69 (3H, s, $OCH_3$); 3.19 (1H, m, H-11β); 3.10 (1H, m, H-8α); 2.93 (1H, m, H-10α); 2.61 (2H, m, H-8β+H-10β); 2.51 (1H, m, H-11α); 2.05 (1H, m, H-$6_A$); 1.89 (1H, m, H-$6_B$); 1.77 (2H, m, $CH_2$-7); 1.44 (9H, s, $OC(CH_3)_3$).

EXAMPLE 39

Preparation of tert-butyl 2-methoxycarbonylmethyl-2-hydroxy-6-methylhept-5-enoate

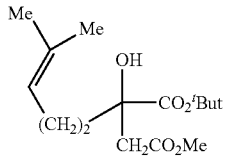

1°) Preparation of Intermediate Oxalate

5-Bromo-2-methyl-pent-2-ene (1.34 g, 8.2 mmol) was added dropwise to a stirred mixture of magnesium (240 g, 10 mmol) (activated with further crystal of iodine) in anhydrous tetrahydrofurane (8 ml). The onset of the reaction is accompanied with a vigorous overheating and refluxing of the reaction mixture. The reflux was maintained until most of magnesium had reacted and the reaction mixture was diluted with anhydrous tetrahydrofurane (16 ml). To a stirred mixture of tert-butyl ethyl oxalate (1.4 g, 8 mmol) in anhydrous tetrahydrofurane (8 ml) was added the resulting Grignard reagent at −78° C. over a period of 20 minutes. The temperature was allowed to rise to −15° C. over a period of 2 hours and the mixture was quenched with hydrochloric acid 1N. The separated organic layer was washed three times with brine, dried over magnesium sulfate and evaporated to dryness. The resulting crude product (2 g) was purified by column chromatography (cyclohexane/ethyl acetate (98:2), silica (15-40 μm) 80 g) to provide an oil (660 mg, 39%). The intermediate α-cetoester showed the following characteristics:

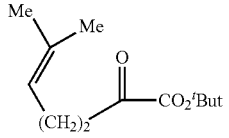

$^1$H NMR 400 MHz ($CDCl_3$) (δ ppm, J Hz): 5.08 (1H, m, H-5); 2.80 (2H, t, J=7.3, CH2-3); 2.28 (2H, m, $CH_2$-4); 1.68 (3H, s, $CH_3$); 1.62 (3H, s, $CH_3$); 1.54 (9H, s, O-tertBu).

2°) Preparation of the Title Compound

To a stirred solution of lithium bis-(trimethylsilylamide) 1M in tetrahydrofurane (9 ml, 9 mmol) was added anhydrous methyl acetate (0.7 ml, 8.75 mmol) at −78° C. over a period of 1 minute and this was allowed the reaction to proceed at −78±5° C. for 20 minutes. To a stirred mixture of tert-butyl 2-oxo-6-methylhept-5-enoate prepared above (640 mg, 3 mmol) in anhydrous tetrahydrofurane (10 ml) was added the lithium enolate at −78° C. over a period of 5 minutes and the resulting mixture was stirred at −78±5° C. for 30 minutes. After monitoring in CCM, the freezing bath was removed and the mixture was quenched with 15% ammonium chloride solution (10 ml). The separated organic layer was washed with 15% ammonium chloride solution (10 ml) and evaporated to dryness. The aqueous layers were extracted with ether (2×10 ml). The organic layers were combined with the concentrate and washed with brine (10 ml), dried over magnesium sulfate and evaporated to dryness. The resulting crude product (1.3 g) was purified by column chromatography (cyclohexane/ethyl acetate (95:5), silica (15-40 μm) 60 g) to provide an oil (222 mg, 26%). The product thus obtained showed the following characteristics:

$^1$H NMR 400 MHz ($CDCl_3$) (δ ppm, J Hz): 5.07 (1H, m, HC=); 3.67 (3H, s, $OCH_3$); 3.66 (1H, s, OH); 2.86 et 2.67 (2H, 2d, $J_{AB}$=15.8 $\underline{CH_2}CO_2$); 2.13 (1H, m, $CH_2$); 1.85 (1H, m, $CH_2$); 1.67 (3H, s, $CH_3$) et (2H, m, $CH_2$); 1.59 (3H, s, $CH_3$); 1.51 (9H, s, tert-BuO).

EXAMPLE 40

Preparation of ethyl 2-N-[(4'S)-isopropyl-2'-oxazolidino]carbonylmethyl-2-hydroxy-6-methylhept-5-enoate

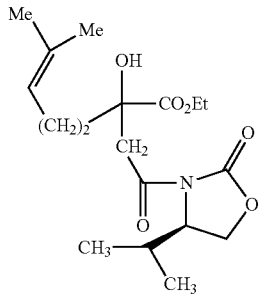

A commercial solution of lithium bis-(trimethylsilylamide) 1M in tetrahydrofurane (1.28 ml, 1.28 mmol) was added to a stirred solution of (4S)-3-acetyl-4-isopropyl-2-oxazolidinone (200 mg, 1.17 mmol) in anhydrous tetrahydrofurane at −78° C. and this was allowed the reaction to proceed at −78° C. for 30 minutes. Then a solution of ethyl 2-oxo-6-methylhept-5-enoate (323 mg, 1.75 mmol) in anhydrous tetrahydrofurane (5 ml) was added and the resulting mixture was stirred at −78° C. for 1 hour. After monitoring in CCM, the mixture was quenched with 15% ammonium chloride solution (5 ml). The separated organic layer was washed with 15% ammonium chloride solution (10 ml), then with brine (10 ml), dried over magnesium sulfate and evaporated to dryness. The $^1$H NMR spectra of the crude product showed a diastereomeric mixture ~2.5/1. The resulting crude product (516 mg) was purified by column chromatography (cyclohexane/ethyl acetate (90:10 to 80:20), silica (15-40 μm) 25 g) to provide the minority diastereomer like a yellow oil (55 mg, 13.7%) showing the following characteristics:

$^1$H NMR 400 MHz ($CDCl_3$) (δ ppm, J Hz): 5.06 (1H, m, H-3'); 4.41 (1H, m, H-4"); 4.25 (4H, m, $CH_2$-5" and O $\underline{CH_2}CH_3$); 3.72 (1H, s, OH); 3.52 and 3.41 (2H, 2d, $J_{AB}$=17.9, $CH_2$-3); 2.36 (1H, m, H-6"); 2.16 (1H, m, $CH_2$"); 1.92 (1H, m, $CH_2$'); 1.75 (2H, m, $CH_2$'); 1.67 (3H, s, $CH_3$'); 1.59 (3H, s, $CH_3$'); 1.30 (3H, t, J=7.1, $OCH_2\underline{CH_3}$); 0.89 (3H, d, J=7.0, $CH_3$"); 0.87 (3H, d, J=6.9, $CH_3$").

Then the majority diastereomer like a pale yellow oil (93 mg, 23.2%) showing the following characteristics:

$^1$H NMR 400 MHz ($CDCl_3$) (δ ppm, J Hz): 5.06 (1H, m, H-3'); 4.40 (1H, m, H-4"); 4.23 (4H, m, $CH_2$-5" and O $\underline{CH_2}CH_3$); 3.68 (1H, s, OH); 3.46 (2H, s, $CH_2$-3); 2.33 (1H, m, H-6"); 2.16 (1H, m, $CH_2$'); 1.91 (1H, m, $CH_2$'); 1.75 (2H, m, $CH_2$'); 1.67 (3H, s, $CH_3$'); 1.59 (3H, s, $CH_3$'); 1.28 (3H, t, J=7.1 OCH2$\underline{CH_3}$); 0.90 (3H, d, J=7.0, $CH_3$"); 0.87 (3H, d, J=6.9, $CH_3$").

EXAMPLE 41

Preparation of ethyl 2-(1'R,2'S,5'R)-methoxycarbonylmethyl-2-hydroxy-6-methylhept-5-enoate

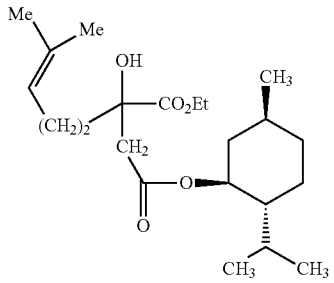

To a stirred commercial solution of lithium bis-(trimethylsilylamide) 1M in tetrahydrofurane (14 ml, 14 mmol), was added menthyl (1R,2S,5R)-(−)-acetate (2.8 g, 14.1 mmol) at −78° C. and this was allowed the reaction to proceed at −78° C. for 30 minutes. To a stirred mixture of ethyl 2-oxo-6-methylhept-5-enoate prepared above (867 mg, 4.7 mmol) in anhydrous tetrahydrofurane (12 ml) was added the lithium enolate at −78° C. over a period of 15 minutes and the resulting mixture was stirred at −78° C. for 3 minutes (CCM monitoring). The mixture was quenched with hydrochloric acid 1N (30 ml). The separated aqueous layer was extracted with tert-butyl methyl ether (2×15 ml) and the combined organic layers were washed with brine (3×15 ml), dried over magnesium sulfate and evaporated to dryness. The $^1$H NMR spectra of the crude product showed a diastereomeric mixture ~6/4. The resulting crude product was purified by column chromatography (cyclohexane/ethyl acetate (98:2), silica (15-40 μm) 70 g) to provide the expected products (1 g, 57%). The separated diastereomers thus obtained showed the following characteristics:

Majority Diastereomer:

$^1$H NMR 400 MHz ($CDCl_3$) (δ ppm, J Hz): 5.03 (1H, t, J=7.0, H-3'); 4.69 (1H, td, J=10.9 and 4.3, H-$1_{Men}$); 4.24 (2H, q, J=7.0, O$\underline{CH_2}CH_3$); 3.77 (1H, s, 2-OH); 2.91 and 2.67 (2H, 2d, $J_{AB}$=16.4, $CH_2CO_2$); 2.13 (1H, m, CH'); 1.97 (1H, m, H-6$eq_{Men}$); 1.85 (2H, m, CH' and H-$7_{Men}$); 1.75-1.6 (4H, m, $CH_2$' and H-3eq, 4$eq_{Men}$); 1.67 (3H, s, $CH_3$'); 1.58 (3H, s, $CH_3$'); 1.45 (1H, m, H-5$_{Men}$); 1.35 (1H, m, H-2ax$_{Men}$); 1.30 (3H, t, J=6.9, $OCH_2\underline{CH_3}$); 1.03 (1H, m, H-3ax$_{Men}$); 0.93 (1H, m, H-6ax$_{Men}$); 0.89 (6H, d, J=6.8, 2×$CH_{3(Men)}$); 0.87 (1H, m, H-4ax$_{Men}$); 0.73 (3H, d, J=6.9, $CH_{3(Men)}$).

Minority Diastereomer:

$^1$H NMR 400 MHz ($CDCl_3$) (δ ppm, J Hz): 5.05 (1H, t, J=7.0, H-3'); 4.67 (1H, td, J=10.7 and 4.7, H-1$_{Men}$); 4.25 (2H, m, $O\underline{CH_2}CH_3$); 3.74 (1H, s, 2-OH); 2.92 and 2.65 (2H, 2d, $J_{AB}$=15.9, $\underline{CH_2}CO_2$); 2.12 (1H, m, CH'); 1.97 (1H, m, H-6eq$_{Men}$); 1.86 (2H, m, CH' and H-7$_{Men}$); 1.75-1.6 (4H, m, $CH_2$' and H-3eq, 4eq$_{Men}$); 1.67 (3H, s, $CH_3$'); 1.58 (3H, s, $CH_3$'); 1.48 (1H, m, H-5$_{Men}$); 1.36 (1H, m, H-2ax$_{Men}$); 1.31 (3H, t, J=7.0, $OCH_2\underline{CH_3}$); 1.15-0.8 (3H, m, H-3ax, 6ax, 4ax$_{Men}$); 0.89 (6H, d, J=6.9, 2×$CH_{3(Men)}$). 0.76 (3H, d, J=7.0, $CH_{3(Men)}$).

EXAMPLE 42

Preparation of ethyl 2-[(R)-1',2'-triphenyl-ethan-2'-ol]ethoxycarbonylmethyl-2-hydroxy-6-methylhept-5-enoate

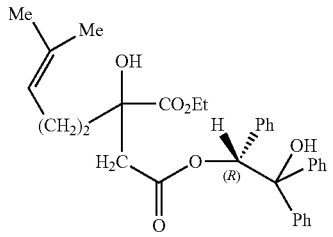

A commercial solution of lithium bis-(trimethylsilylamide) 1M in tetrahydrofurane (6 ml, 6 mmol) was added to a stirred solution of R-(+)-1,1,2-triphenyl-1,2-ethanediol 2-acetate (665 mg, 2 mmol) in anhydrous tetrahydrofurane (6 ml) at −78° C. The temperature was allowed to rise to 0° C. over a period of 3 hour, then was added anhydrous heptane (10 ml). To this stirred reaction mixture at −78° C. a solution of ethyl 2-oxo-6-methylhept-5-enoate (368 mg, 2 mmol) in anhydrous tetrahydrofurane (2 ml) was added and the temperature was allowed to rise to −40° C. over a period of 1 hour. After monitoring in CCM, the freezing bath was removed and the mixture was quenched with 15% ammonium chloride solution (10 ml). The separated organic layer was washed with 15% ammonium chloride solution (10 ml) and evaporated to dryness. The aqueous layers were extracted with dichloromethane (2×10 ml). The organic layers were combined with the concentrate and washed with brine (10 ml), dried over magnesium sulfate and evaporated to dryness. The $^1$H NMR spectra of the crude product showed a diastereomeric mixture ~60/40. The resulting crude product (820 mg) was purified by column chromatography (cyclohexane/ethyl acetate (97:3 to 95:5), silica (15-40 μm) 80 g) to provide the expected products (361 mg, 35%). The separated diastereomers thus obtained like white crystalline compounds showed the following characteristics:

Minority Diastereomer:

$^1$H NMR 400 M ($CDCl_3$) (δ ppm, J Hz): 7.66 (2H, d, J=7.5, o-Ph); 7.43 (2H, t, J=7.7, m-Ph); 7.35-7.0 (11H, m, Ph); 6.72 (1H, s, H-1"); 4.95 (1H, m, H-3'); 4.41 (2H, m, $O\underline{CH_2}CH_3$); 3.42 (1H, s, 2-OH); 2.90 and 2.67 (2H, 2d, $J_{AB}$=16.5, $CH_2$-3); 2.53 (1H, s, 2"-OH); 1.98 (1H, m, $CH_2$); 1.8-1.5 (3H, m, $CH_2$); 1.63 (3H, s, $CH_3$); 1.52 (3H, s, $CH_3$); 1.38 (3H, t, J=7.1, $OCH_2\underline{CH_3}$).

Majority Diastereomer:

$^1$H NMR 400 MHz ($CDCl_3$) (δ ppm, J Hz): 7.52 (2H, d, J=7.5, o-Ph); 7.36 (2H, t, J=7.6, m-Ph); 7.27 (1H, t, J=7.3, p-Ph); 7.2-7.0 (10H, m, Ph); 6.59 (1H, s, H-1"); 4.98 (1H, m, H-3'); 3.90 and 3.34 (2H, 2m, $O\underline{CH_2}CH_3$); 3.56 (1H, s, 2-OH); 3.22 (1H, s, 2"-OH); 2.88 and 2.69 (2H, 2d, $J_{AB}$=16.7, $CH_2$-3); 2.06 and 1.79 (2H, 2m, $CH_2$); 1.7-1.5 (2H, m, $CH_2$); 1.64 (3H, s, $CH_3$); 1.54 (3H, s, $CH_3$); 0.99 (3H, t, J=7.1, $OCH_2\underline{CH_3}$).

EXAMPLE 43

Preparation of tert-butyl 2-[(R)-1',2',2'-triphenyl-ethan-2'-ol]ethoxycarbonylmethyl-2-hydroxy-6-methylhept-5-enoate

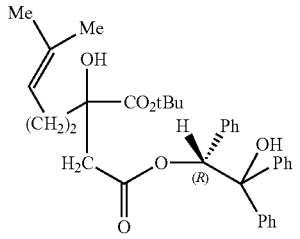

A commercial solution of lithium bis-(trimethylsilylamide) 1M in [tetrahydrofurane] *tetrahydrofuran* (3 ml, 3 mmol) was added to a stirred solution of R-(+)-1,1,2-triphenyl-1,2-ethanediol 2-acetate (330 mg, 1 mmol) in anhydrous [tetrahydrofurane] *tetrahydrofuran* (3.5 ml) at −78° C. The temperature was allowed to rise to −10° C. over a period of 3 [hour] *hours* then was added anhydrous heptane (5 ml). To this stirred reaction mixture at −78° C. a solution of tert-butyl 2-oxo-6-methylhept-5-enoate (276 mg, 1.5 mmol) in anhydrous [tetrahydrofurane] *tetrahydrofuran* (2 ml) was added and the temperature was allowed to rise to −40° C. over a period of 1 hour. After monitoring in CCM, the [freezing] *cold* bath was removed and the mixture was quenched with 15% ammonium chloride solution (5 ml). The separated organic layer was washed with 15% ammonium chloride solution (5 ml) and evaporated to dryness. The aqueous layers were extracted with dichloromethane (2×10 ml). The organic layers were combined with the concentrate and washed with brine (5 ml), dried over magnesium sulfate and evaporated to dryness. The $^1$H NMR spectra of the crude product showed a diastereomeric mixture ~75/25. The resulting crude product (550 mg) was purified by column chromatography (cyclohexane/ethyl acetate (96:4, 95/5 then 90:10), silica (15-40 [□m] *μm*) 60 g) to provide the expected products (217 mg, 40%). The majority diastereomer thus obtained [like] *was a* white crystalline compound *that* showed the following characteristics:

$^1$H NMR 400 MHz ($CDCl_3$) (δ ppm, J Hz): 7.53 (2H, d, J=7.4, o-Ph); 7.36 (2H, t, J=7.6, m-Ph); 7.28 (1H, t, J=7.3, p-Ph); 7.2-7.0 (10H, m, Ph); 6.66 (1H, s, H-1"); 5.00 (1H, m, H-3'); 3.50 (1H, s, 2-OH); 2.94 (1H, s, 2"-OH); 2.76 and 2.61 (2H, 2d, $J_{AB}$=16.3, $\underline{CH_2}$—CO2); 2.06 and 1.78 (2H, 2m, $CH_2$); 1.65 (3H, s, $CH_3$); 1.55 (3H, s, $CH_3$ and 2H, m, $CH_2$); 1.23 (9H, s, tert-BuO).

EXAMPLE 44

Preparation of 2-carboxymethyl-6,6-dimethyl-2-tetrahydro-pyranecarboxylic acid or O-demethylan-hydrohomoharringtonic acid

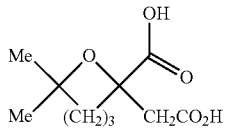

(Method D)

A solution of ethylenic diacid resulting from the Example 3 (1.5 g, 6.94 mmol) in formic acid (2.6 ml) was stirred at 60° C. for 16 hours. After return at ambient temperature, formic acid was removal in vacuo and the resulting crude product was dried at 40° C. in vacuo for 20 hours (1.5 g, 100%).

EXAMPLE 45

Preparation of 2-methoxycarbonylmethyl-6,6-dimethyl-2-tetrahydro-pyranecarboxylic or anhydrohomoharringtonic acid from product resulting from Example 39

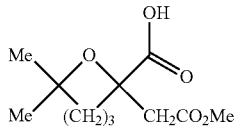

A solution of tert-butyl 2-methoxycarbonylmethyl-2-hydroxy-6-methylhept-enoate resulting from Example 39 (50 mg, 0.175 mmol) in formic acid (0.5 ml) was stirred at room temperature for 9 days. After removal of formic acid in vacuo, the residue was treated with 5% sodium hydrogen carbonate solution up to pH 8. The aqueous layer was washed with ethyl acetate then, after acidification (pH 1) with hydrochloric acid 1N, was extracted with ethyl acetate. The organic layer was dried over magnesium sulfate and evaporated to dryness to provide anhydrohomoharringtonic acid (20 mg, 50%).

EXAMPLE 46

Preparation of Purified (−) Cephalotaxine from Total Alkaloidic Extract of Cephalotaxus sp

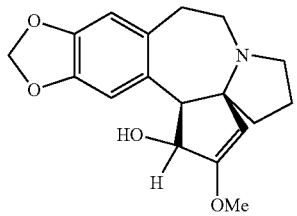

Partially racemized cephalotaxine [H. Wenkui; L. Yulin; P. Xinfu, Scientia Sinica,; 23; 7; 835 (1980)]

$^1$H NMR of two batches of cephalotaxine (extracted in the same conditions as above) with the optically active NMR shift reagent europium(III) tris[3-(heptafluoropropylhydroxymethylene)-(+)-camphorate (1 éq) showed the following results:

Batch A: $^1$H NMR 400 MHz ($CDCl_3$) (δ ppm): 6.06 (1H, OCH20 (+)-cephalotaxine) and 5.82 (1H, OCH20 (+)-cephalotaxine); 5.99 (1H, OCH20 (−)-cephalotaxine) and 5.76 (1H, OCH20 (−)-cephalotaxine).

Presence of 11±5% de (+)-cephalotaxine.

$[\alpha]^{22}$=−134.0° (c=0.214; CHCl3): calculated rate 25±5%

Batch B: Slightly Racemized (1%)

$[\alpha]^{19}$=−173.3° (c=0.208; CHCl3)

Enantiomeric Enrichment of the Natural Cephalotaxine:

Crude chromatographied cephalotaxine (20 g) was dissolved at 55° C. in dry methanol (100 ml). Crystallization occurs by cooling with rotary evaporator and after filtration the product thus obtained showed 99.9% of HPLC purity, $[\alpha]^{20}_{D}$=−130° (Cl, $CHD_3$) corresponding to 10% of racemization. The crystallized product thus obtained (20 g) was dissolved again in hot methanol (100 ml).

Slowly cooling the solution allows translucent prisms composed of pure enantiomeric (−)-cephalotaxine $[\alpha]^{20}_{D}$=−185° (Cl,$CHCl_3$).

After filtration, the mother liquors was allowed to slowly evaporate at room temperature and crystals in the form of macled needles exclusively composed of racemic cephalotaxine $[\alpha]^{D}_{20}$=0.5° (Cl; $CHCl_3$) were obtained.

After filtration, the second mother liquors allowed prisms composed of (−)-cephalotaxine identical to this obtained at the first crystallization.

After filtration, the third mother liquors still allowed macled needles (urchins) composed of (±)-cephalotaxine.

The cycle is repeated three times. The combined prismatic crystals was recrystallized once to give enantiomerically pure (−)-cephalotaxine, while the combined macled needles treated in the same way gives 100% racemic cephalotaxine.

Chemical Evaluation of the Enantiomeric Purity of Natural Cephalotaxine:

A sample of partially racemized natural cephalotaxine was inserted in the process, which sequence is described in the Examples 1, 2, 3, 4, 5, 6, 15, 19 and 21, by using a pure (2R)-homoharrintonic acid resulting from Example 19.

The HPLC analysis of the diastereomeric mixture of anhydro-homoharrintonine thus obtained showed a significant enantio-epi-homoharringtonine rate (11%±3%) corresponding to the (+)-cephalotaxine content in the racemic mixture of origin (it has been demonstrated that the two antipodes of the homoharringtonic acid react in a stoichiometric way comparable to the pure enantiomeric cephalotaxine).

EXAMPLE 47

Preparation of Homoharringtonine, from Anhydro-Homoharringtonine

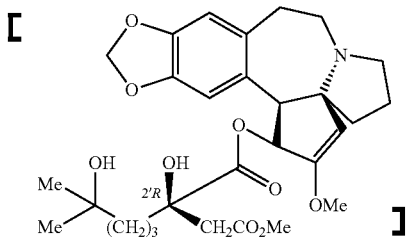

-continued

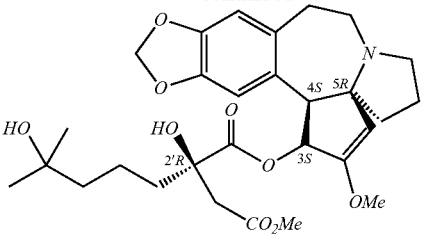

1°) Method A

A commercial solution of hydrobromic acid in acetic acid (17.4 ml, 86.6 mmol, HBr 30% w/w) was added to a stirred solution of anhydrohomoharringtonine resulting from Example 21 (50.8 g, 9.63 mmol) in anhydrous dichloromethane (25.6 ml) at −10° C. After stirring at −10° C. for 3 hours was added water (240 ml) and the reaction mixture was become viscous. The temperature was allowed to rise to room temperature and after stirring for 2.5 hours was added sodium carbonate 0.76M (406 ml) to pH 8. The resulting aqueous layer was saturated with sodium chloride, then was extracted with dichloromethane (3×230 ml) and the combined organic layers were dried over magnesium sulfate and evaporated to dryness to afford a foam. After phase reverse chromatography below-mentioned were obtained 4.03 g of homoharringtonine (77%). The product thus obtained showed identical characteristics to this resulting from Example 25.

2°) Method B

To a stirred solution of anhydrohomoharringtonine resulting from Example 21 (214 mg, 0.406 mmol) in anhydrous dichloromethane (1.1 ml) was added at −10° C. a commercial solution of hydrobromic acid in acetic acid (0.728 ml, 3.6 mmol, HBr 30% w/w). After stirring at −10° C. for 3 hours, was added water (13 ml) and then the temperature was raised to 20° C. After stirring at 20° C. for 3 hours, was added a sodium carbonate solution (0.76M; 31.5 ml) up to pH 8. The resulting aqueous layer, after saturation with sodium chloride, was extracted with dichloromethane (3×20 ml) and the combined organic layers were dried over magnesium sulfate and evaporated to dryness. The resulting crude product was purified by phase reverse chromatography below-mentioned to provide homoharringtonine (166 mg, 75%). The product thus obtained showed identical characteristics to this resulting from Example 25.

EXAMPLE 48

Preparation of Harringtonine Drug Substance by Purification of Commercial Natural Harringtonine A. Analytical Profile of Starting Product By combination of HPLC analysis with UV detection (see FIG. 8) and mass spectrometry detection (see FIGS. 9 and 10) a total of 6.5% of related compound (identified as b,c: position isomer of harringtonine=3.4%; d: homoharringtonine=3%; e: 4'-demethyl harringtonine=0.01%; f: drupacine derivative: 0.05%) are found in the starting product.

B. Chromatography of Natural Harringtonine

Natural harringtonine (5 grams) is injected on a preparative high-pressure liquid chromatography (HPLC) system (Prochrom stainless steel; permanent axial compression; diameter: 80 mm; length: 1000 mm) containing 1000 grams of reverse phase octadecylsilane specially dedicated for basic compounds as stationary phase. Then elution is performed in using a gradient of pH 3 buffered methanol-water solution as mobile phase (pressure 1200 psi). Unwanted fractions are discarded based upon in-line UV spectrophotometric detection. Kept fractions are collected in 16 separate containers which each are individually checked in using an analytical HPLC system exhibiting a different selectivity pattern (octadecylsilane as stationary phase and buffered acetonitrile-water system as mobile phase). During the development phase, a dual in-line UV-MS detection is used. After discarding of the fractions representing more than 0.5% of the total content of harringtonine, fractions which complied with pre-established specification were gathered, neutralized then evaporated under reduce pressure. Then crude concentrated solution of harringtonine are alkalinized at pH 8.5 with aqueous ammonia and partitioned with dichloromethane. Resulting organic solution is concentrated under high vacuum. In-process HPLC analysis indicated a total of related compound lower than 1.5%.

C. Crystallization of Raw Harringtonine

Under a laminar flow hood, the above raw harringtonine (4.1 grams) is dissolved in methanol (5 ml), at 30° C. The resulting alcoholic solution was filtered on a 0.25μ sterile Millipore filter to remove microparticles and germs and collected in a sterilized rotary flask. Then, deionized water (50 mL) is added and methanol is completely removed under vacuum at 30° C. in using a decontaminated rotary evaporator. After removing methanol, heating is stopped and the aqueous solution of harringtonine is kept under vacuum and rotation is continued during appearance of white crystals of pure harringtonine. The stirring is continued until no more crystal occurs. Under a laminar flow hood, the suspension of is poured on a sintered glass filter with house vacuum. The resulting crystalline solid cake is washed two times with cold desionized water (10 mL×2). The white translucent crystals are then dried using high vacuum at 40° C. for 24 hours. Overall yield is 76%. All operations were documented prior to start the process and full current Good Manufacturing Practices were applied. This clinical batch corresponds to 400 therapeutic units dosed at 10 mg.

D. Analysis

Routine analytical procedure includes solvent residues, loss on drying, water determination, melting point, IR and NMR spectrum, related compound and assay by HPLC. FIGS. 9 and [10] *11* compare HPLC chromatogram before and after purification in using this process. Table II shows the comparison of the corresponding related compound content.

TABLE II

Impurity Content Decrease After Application Of This Process

| Peak | Related Compound (impurities) | Before this process | After this process |
|---|---|---|---|
| a | Harringtonine (HA) | 93.49 | 99.97 |
| b | HA isomer | 1.76 | 0 |
| c | HA isomer | 1.67 | 0 |
| d | Homoharringtonine | 3.01 | 0 |
| e | 4'-dimethyl-HA | 0.01 | 0.03 |
| f | Drupacine analog | 0.05 | 0 |
| | Sum of Related Compounds | 6.49 | 0.03 |
| | Rate 6.49/0.03 | 216 | |

For the aim of further characterization, more advanced studies were performed including differential scanning calorimetry (DSC) thermogravimetry, 2D NMR, solid NMR and X-ray powder diffractometry.

Infrared Spectrometry:

Identical IR spectra were obtained by either the KBr pellet and/or mineral oil mull preparation technique. FIG. 7 shows typical infrared spectrum (KBr) for unambiguous identification at the solid state of the crystalline harringtonine obtained by this process. A series of sharp absorption bands are noted at 615, 654, 674, 689, 709, 722, 750, 761 805, 850, 928, 989, 1022, 1033, 1062, 1083, 1112, 1162, 1205, 1224, 1262, 1277, 1308, 1340, 1364, 1382, 1438 1486, 1508, 1625, 1656, 1725, 1745, 2883, 2936, 2972, 3079, 3353, 3552 and 3647 $cm^{-1}$ Differential Scanning Calorimetry (DSC) And Thermogravimetry (TG)

Measurement of DSC and TG were obtained on a Mettler Toledo STAR System. Approximately 12 mg of harringtonine drug substance were accurately weighed (12.4471 mg) into a DSC pan. The sample was heated from 25° C. to 200° C. at a rate of 10° C./min The DSC data were obtained following a standard method in the art. The DSC curve of crystalline harringtonine drug substance ((FIG. 6), exhibits a melting endotherm at 79.5° C. No subsequent decomposition occurred under the upper tested temperature 200° C. Simultaneous TG measurement, indicated a loss on drying of 1.3% which did not correspond to a lost of structural molecule of solvent or water.

EXAMPLE 49

Preparation of Homoharringtonine Drug Substance by Purification of Raw Semi-Synthetic (Hemi-Synthetic) Homoharringtonine A. Analytical Profile of Starting Product Crude reaction mixture of raw homoharringtonine contains a potential of 250 grams of homoharringtonine DS together with process impurities such as catalyst, unchanged starting product (anhydro-homo-harringtonine), and some related side product. HPLC analysis with UV detection (see left-side chromatogram on FIG. 12) indicated a total of 9% of related impurities.

B. Chromatography of Semi-Synthetic Homoharringtonine

Raw semi-synthetic homoharringtonine (550 grams) is injected on a preparative high-pressure liquid chromatography (HPLC) system (Prochrom stainless steel; permanent axial compression; diameter: 450 mm; length: 1000 mm) containing 48,000 grams of reverse phase octadecylsilane specially dedicated for basic compounds as stationary phase. Then elution is performed in using a gradient of pH 3 buffered methanol-water solution as mobile phase (pressure 1200 psi, flow-rate 540 L/hour). Unwanted fractions are discarded based upon by-passed in-line UV spectrophotometric detector. Kept fractions are collected in 30 separate stainless steel containers (20 or 50 L each) which are individually checked in using an analytical HPLC system exhibiting a different selectivity pattern (octadecylsilane as stationary phase and buffered acetonitrile-water system as mobile phase) and equipped with a diode array detector. After discarding of the fractions representing more than 0.5% of the total content of homoharringtonine, fractions which complied with pre-established specification were gathered, neutralized then evaporated under reduce pressure in using a mechanically stirred thin film evaporator. Then crude concentrated solution of homoharringtonine are alkalinized at pH 8.5 with aqueous ammonia and partitioned with dichloromethane. Resulting organic solution is concentrated under high vacuum. In-process HPLC analysis indicated a total of related compound lower than 0.5% (see right-side chromatogram on FIG. 12)

C. Crystallization of Homoharringtonine DS

In a controlled clean room, under a laminar flow hood, the above raw homoharringtonine DS (210 grams) is dissolved in methanol (240 mL), at 30° C. The resulting alcoholic solution is filtered on a 0.25μ sterile Millipore filter to remove microparticles and germs and collected in a sterilized pilot rotary flask. Then, desionized water (2400 mL) is added and methanol is completely removed under vacuum at 30° C. in using a decontaminated pilot rotary evaporator. After removing methanol, heating is stopped and the aqueous solution of homoharringtonine DS is kept under vacuum and rotation is continued during appearance of white crystals of pure homoharringtonine. The stirring is continued until no more crystal occurs. Under a laminar flow hood, the suspension of is poured on a sintered glass filter with house vacuum. The resulting crystalline solid cake is washed two times with cold desionized water (450 mL×2). The white crystals are then dried using high vacuum at 60° C. for 48 hours. Overall yield is 88% from potential content of homoharringtonine in raw semi-synthetic homoharringtonine. All operations were documented prior to start the process and full current Good Manufacturing Practices were applied. This clinical batch corresponds to 40,000 therapeutic units dosed at 5 mg.

D. Analysis

Routine analytical procedure includes solvent residues, loss on drying, water determination, melting point, IR and NMR spectrum, related compound and assay by HPLC. FIG. 13 shows HPLC chromatogram before and after crystallization. Total of related impurities of homoharringtonine DS is 0.03%.

For the aim of further characterization, more advanced studies were performed including differential scanning calorimetry (DSC), thermogravimetry (TD), 2D NMR, solid NMR and X-ray powder diffractometry.

Infrared Spectrometry:

Identical IR spectra were obtained by either the KBr pellet and/or mineral oil mull preparation technique. FIG. 5 shows typical infrared spectrum (KBr) for unambiguous identification at the solid state of the crystalline homoharringtonine obtained by this process. A series of sharp absorption bands are noted at 612, 703, 771, 804, 826, 855, 879, 932, 1029, 1082, 1119, 1135, 1161, 1191, 1229, 1274, 1344, 1367, 1436, 1457, 1488, 1505, 1653, 1743. 2814, 2911, 2958, 3420, and 3552 $cm^{-1}$ Differential Scanning Calorimetry (DSC) And Thermogravimetry (TG)

Measurement of DSC and TG were obtained on a Mettler Toledo STAR System. Approximately 11 mg of homoharringtonine drug substance were accurately weighed (10.6251 mg) into a DSC pan. The sample was heated from 25° C. to 250° C. at a rate of 5° C./min. The DSC data were obtained following a standard method in the art. The DSC curve of crystalline homoharringtonine drug substance (FIG. 3), exhibits a melting endotherm at 145.6° C. Melting range performed by the capillary method (Bucchi Apparatus) gave 143-145° C. Literature indicated 144-146° C. [Anonymous, Acta Bot. Sin. 22, 156 (1980) cited by L. Huang and Z. Xue, Cephalotaxus Alkaloids, in "The Alkaloids", vol. XXIII, pp 157, (1988). Crystallization medium was not published. This is the only literature reference regarding melting point of a crystalline form of HHT]

X-Ray Powder Diffraction

X-ray powder diffraction pattern was collected on a INEL [microdiffractomer] *microdiffractometer*, model DIFFRACTINEL. Powdered homoharringtonine DS was packed in a glass capillary tube and was analyzed according to a standard method in the art. The X-ray generator was [opered] *operated* at 45 kV and 40 mA, using the copper Kalpha line as the radiation source. The sample was rotated along the chi axis and data was collected between 0 and 120 deg 2-theta. A collection time of 1200 sec was used. As [showed on] *shown in* FIG. [2] *4*, the x-ray powder diffraction for this crystalline form of homoharringtonine shows a typical pattern including major reflection peaks at approximately 7.9, 9.2, 10.9, 14.9, 16.0, 17.7, 19.5, 19.7, 21.78, 23.1, 25.3, 25.4 and 25.7 deg 2-theta.

EXAMPLE 50

Preparation of Homoharringtonine Drug Substance by Purification of a Commercial Sample of Impure Homoharringtonine from Chinese Source A. Analytical Profile of Starting Product Analytical HPLC chromatogram of natural homoharringtonine (China National Pharmaceutical) is displayed on FIG. 14 (bottom left).

B. Chromatography of Natural Homoharringtonine

Natural homoharringtonine (25 grams) is injected on a preparative high-pressure liquid chromatography (HPLC) system (Prochrom stainless steel; permanent axial compression; diameter: 200 mm; length: 1000 mm) containing 12,000 grams of reverse phase octadecylsilane specially dedicated for basic compounds as stationary phase. Then elution is performed in using a gradient of pH 3 buffered methanol-water solution as mobile phase (pressure 1200 psi, flow-rate 120 L/hour). Unwanted fractions are discarded based upon by-passed in-line UV spectrophotometric detector. Kept fractions are collected in 22 separate stainless steel containers which are individually checked in using an analytical HPLC system exhibiting a different selectivity pattern (octadecylsilane as stationary phase and buffered acetonitrile-water system as mobile phase) and equipped with a diode array detector. After discarding of the fractions representing more than 0.5% of the total content of homoharringtonine, fractions which complied with pre-established specification were gathered, neutralized then evaporated under reduce pressure in using a mechanically stirred thin film evaporator. Then crude concentrated solution of homoharringtonine are alkalinized at pH 8.5 with aqueous ammonia and partitioned with dichloromethane. Resulting organic solution is concentrated under high vacuum. In-process HPLC analysis indicated a total of related compound lower than 0.5%.

C. Crystallization of Homoharringtonine DS

In a controlled clean room, under a laminar flow hood, the above chromatographied homoharringtonine DS (18 grams) is dissolved in methanol (35 mL), at 30° C. The resulting alcoholic solution is filtered on a 0.25 g sterile Millipore filter to remove microparticles and germs and collected in a sterilized pilot rotary flask. Then, desionized water (300 mL) is added and methanol is completely removed under vacuum at 30° C. in using a decontaminated pilot rotary evaporator. After removing methanol, heating is stopped and the aqueous solution of homoharringtonine DS is kept under vacuum and rotation is continued during appearance of white crystals of pure homoharringtonine. The stirring is continued until no more crystal occurs. Under a laminar flow hood, the suspension of is poured on a sintered glass filter with house vacuum. The resulting crystalline solid cake is washed two times with cold desionized water (50 mL×2). The white crystals are then dried using high vacuum at 60° C. for 48 hours. Overall yield is 84% from potential content of homoharringtonine in raw semi-synthetic homoharringtonine. All operations were documented prior to start the process and full current Good Manufacturing Practices were applied.

D. Analysis

Routine analytical procedure includes solvent residues, loss on drying, water determination, melting point, IR and NMR spectrum, related compound and assay by HPLC. FIG. 14 (bottom right) shows HPLC chromatogram after crystallization. Total of related impurities of homoharringtonine DS is 0.05%.

For the aim of further characterization, more advanced studies were performed including differential scanning calorimetry (DSC), thermogravimetry (TD), 2D NMR, solid NMR and X-ray powder diffractometry.

Infrared Spectra, Differential Scanning Calorimetry (DSC) and X-Ray Powder Diffraction gave patterns strictly superimposable to the one of example [2] *49* obtained from semi-synthetic homoharringtonine (FIGS. 5, 3, and 4, respectively).

EXAMPLE 51

Crystallization of the (+)-Homoharringtonine, Non Natural Enantiomer of the Homoharringtonine

[The mother liquors coming from the fractioned crystallization of example 3 are] *A solution containing* (+)-*homoharringtonine is* concentrated then dissolved in methanol at 30° C. The resulting alcoholic solution is filtered on a 0.25μ sterile Millipore filter. Then, [desionized] *deionized* water is added and methanol is completely removed under vacuum at 30° C. [in] using a rotary evaporator. After removing methanol, heating is stopped and the aqueous solution of (+)-homoharringtonine is kept under vacuum and rotation is continued during appearance of white crystals [of pure (+)-homoharringtonine]. The stirring is continued until no more [crystal] *crystalization* occurs. The suspension of crystals is poured on a sintered glass filter with house vacuum. The resulting crystalline solid cake is washed two times with cold [desionized] *deionized* water (50 mL×2). The white crystals are then dried using high vacuum at 60° C. for 48 hours.

Partially enantiomerically enriched crystals thus obtained are dissolved in methanol at 30° C. and the above-mentioned operations (filtration, addition of [desionized] *deionized* water, removal of methanol, [obtention] *obtaining* of crystals) are repeated (mean: 3 times) until [the obtention of] a constant rotary power *is obtained* ([[a] D20=−110] $[\alpha]_D^{20}$=+*110* (c=0.25; [CHCl3] $CHCl_3$)). The (+)-homoharringtonine thus obtained [present] *has* all the analytical characteristics of the natural homoharringtonine (levogyrous), except its rotatory power which is equal but of opposite sign).

DESCRIPTION AND DEFINITION OF HARRINGTONINES

CEPHALOTAXANES

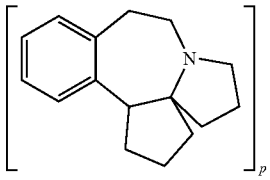

1

EXAMPLES OF HARRINGTONIC ACIDS (R = H), 3
EXAMPLES OF HARRINGTONINES (R = CTX), 4

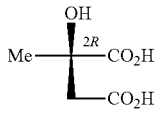

3a
citramalic acid

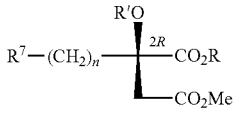

3b
Harringtonic acids R = H

CEPHALOTAXINES

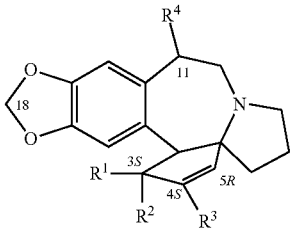

2

| R' | $R^7$ | n | R | |
|---|---|---|---|---|
| | EXAMPLES OF HARRINGTONIC ACIDS (not isolated in the natural form as such) | | | |
| H | $(CH_3)_2C(OH)$— | 2 | H | harringtonic acid |
| H | $(CH_3)_2C(OH)$— | 3 | H | homoharringtonic acid |
| H | $(CH_3)_2C(OH)$— | 1 | H | norharringtonic acid |
| H | $(CH_3)_2CH$— | 2 | H | desoxyharringtonic acid |
| | —C $(CH_3)_2$—O— | 3 | H | anhydrohomoharringtonic acid |
| H | Ph— | 1 | H | neoharringtonic acid |

| Examples of cephalotaxines: | | | | | |
|---|---|---|---|---|---|
| | EXAMPLES OF HARRINGTONINES (natural) | | | | |
| cephalotaxine = CTXOH | H | $(CH_3)_2C(OH)$— | 2 | CTX | Harringtonine: HT |
| 2a | H | $(CH_3)_2C(OH)$— | 3 | CTX | Homoharringtonine: HHT |
| $R^1$ = OH, $R^2$ = $R^4$ = H, $R^3$ = OMe; | H | $(CH_3)_2C(OH)$— | 1 | CTX | Norharringtonine |
| acetylcephalotaxine, 2b | H | $(CH_3)_2CH$— | 2 | CTX | Desoxyharringtonine |
| $R^1$ = Ac, $R^2$ = $R^4$ = H, $R^3$ = OMe; | H | $(CH_3)_2CH$— | 1 | CTX | Nordesoxyharringtonine |
| cephalotaxinone, 2c | H | $(CH_3)_2CH$— | 3 | CTX | Homodesoxyharringtonine |
| $R^1$, $R^2$ = O, $R^3$ = OMe, $R^4$ = H; | H | $(CH_3)_2CH$— | 4 | CTX | Bishomodesoxyharringtonine |
| demethylcephalotaxine, 2d | | —$C(CH_3)_2$—O— | 2 | CTX | Anhydroharringtonine |
| $R^1$ = OH, $R^2$ = $R^4$ = H, $R^3$ = OH; | H | Ph— | 1 | CTX | Neoharringtonine |
| demethylcephalotaxinone, 2e | H | Ph— | 2 | CTX | Homoneoharringtonine |
| $R^1$, $R^2$ = O, $R^3$ = OH, $R^4$ = H; | | | | | |
| 11-hydroxycephalotaxine, | | | | | |
| 2f = 2b + $R^4$ = OH; | | | | | |

ESSENCE OF PRIOR ART

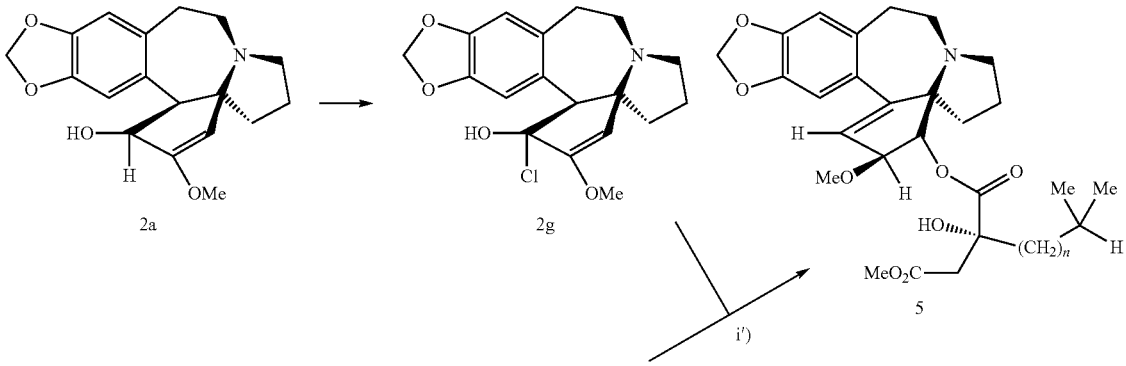

2a

2g

5

-continued

DESCRIPTION AND DEFINITION OF HARRINGTONINES

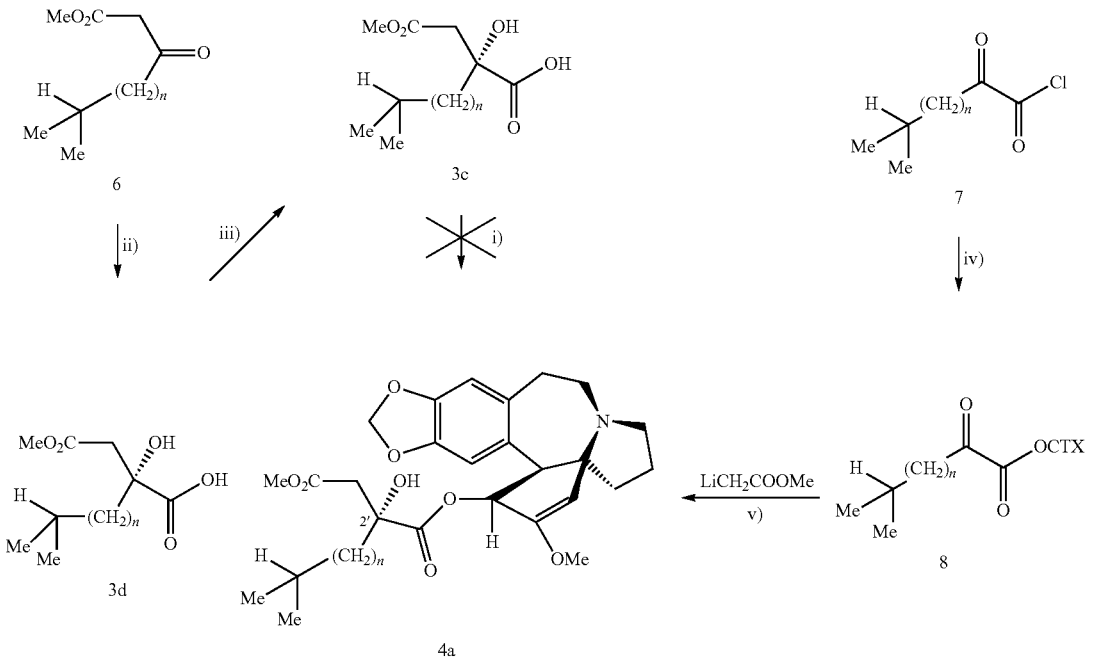

i) Impossible on account of the steric hindrance [K. L. Mikolajczak et coll., Tetrahedron, p. 1995, (1972];

ii) HCN, H+;

iii) MeOH, H+;

i') Silver salt of 3c [K. L. Mikolajczak et coll. J. Med. Chem., p. 63, (1975)];

iv) 2a/pyridine-dichloromethane;

v) according to [T. R. Kelly et coll., Tetrahedron Lett., 3501 (1973)];

ORIGIN of the ANHYDROHARRINGTONINES

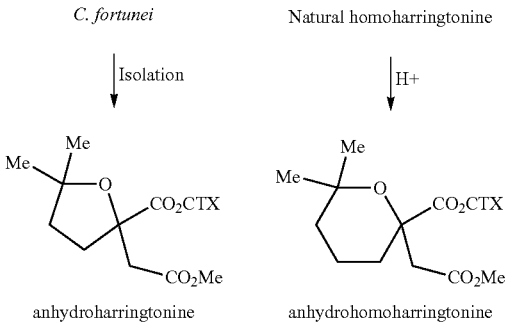

[D. Z. Wang et coll., Yaoxue Xuebao, p. 173, (1992)]

[D. Z. Wang et coll., Yaoxue Xuebao, p. 178, (1992)]

The invention claimed is:

1. [A purified compound of the following formula] *Cephalotaxine, 4-methyl (2'R)-2-hydroxy-2-(4-hydroxy-4-methylpentyl) butanedioate (ester)*:

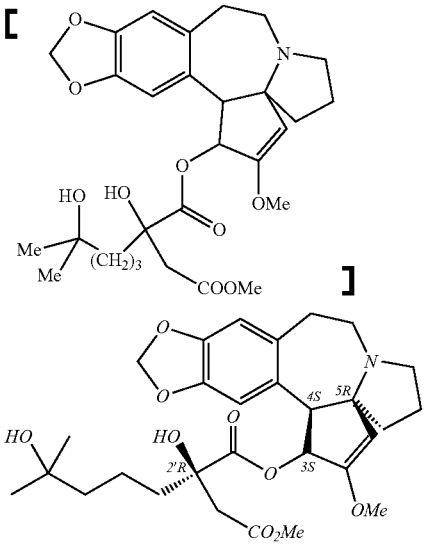

[wherein n=2 or n=3,] having a total content of impurities of lower than 1%[, and/or] *and* having a total content of impurities wherein the major impurity is lower than 0.9%[.] and the chromatographic assay of the [purified compound] *cephalotaxine, 4-methyl (2'R)-2-hydroxy-2-(4-hydroxy-4-methylpentyl) butanedioate (ester)* exhibits a content of the [purified compound] *cephalotaxine, 4-methyl (2'R)-2-hydroxy-2-(4-hydroxy-4-methylpentyl) butanedioate (ester) of* higher than 97.5%, *and/or a salt thereof.*

[2. The purified compound of claim 1, wherein n=3.]

[3. The purified compound of claim 1, wherein n=2.]

[4. A purified crystalline compound of the formula:

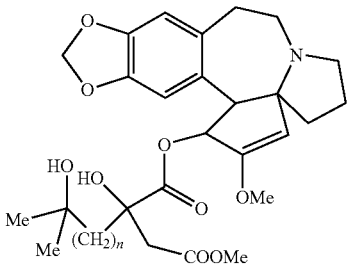

wherein n=2 or n=3, having substantially the same DSC curve as set out in FIG. 1.]

5. [A purified crystalline compound of the formula] *Crystalline cephalotaxine, 4-methyl (2'R)-2-hydroxy-2-(4-hydroxy-4-methylpentyl) butanedioate (ester)*:

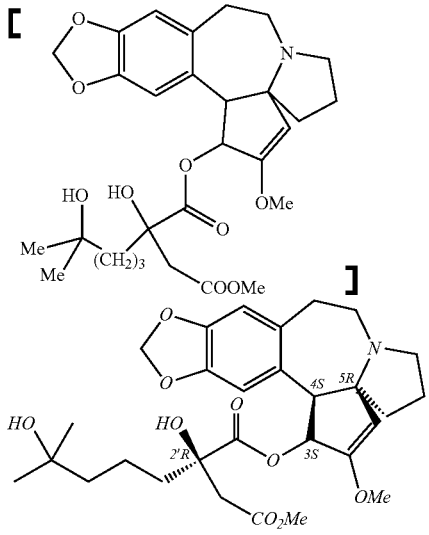

[wherein n=2 or n=3, having substantially the same X-ray diffractogram as set out in FIG. 2, and substantially the same IR spectrum, in KBr, as set out in FIG. 3] *characterized by an X-ray powder diffractogram pattern comprising at least one peak chosen from peaks at approximately 7.9, 9.2, and 10.9 degrees 2-theta and having a total content of impurities of lower than 1%.*

6. [A purified crystalline compound of the formula] *Crystalline cephalotaxine, 4-methyl (2'R)-2-hydroxy-2-(4-hydroxy-4-methylpentyl) butanedioate (ester)*:

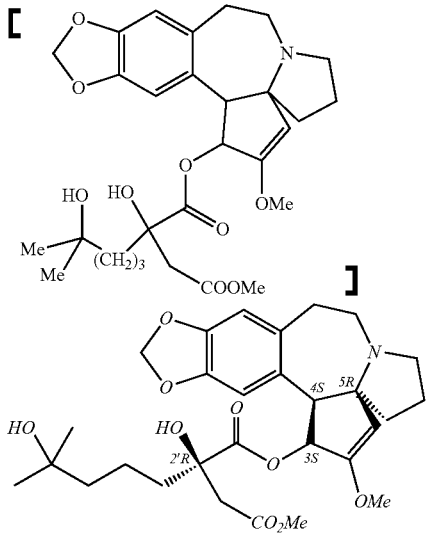

[wherein n=2 or n=3, having substantially the same DSC curve as set out in FIG. 1, substantially the same X-ray diffractogram as set out in FIG. 2, and substantially the same IR spectrum, in KBr, as set out in FIG. 3] *characterized by an X-ray powder diffractogram pattern comprising at least one peak chosen from peaks at approximately 7.9, 9.2, and 10.9 degrees 2-theta and having a total content of impurities of lower than 1% and having a total content of impurities wherein the major impurity is lower than 0.9%.*

7. [A purified crystalline compound of the formula] *Crystalline cephalotaxine, 4-methyl (2'R)-2-hydroxy-2-(4-hydroxy-4-methylpentyl) butanedioate (ester)*:

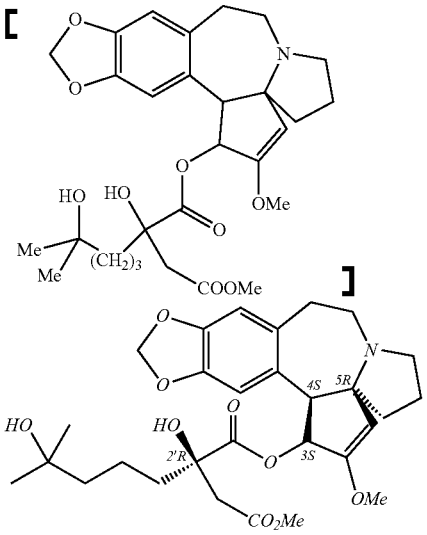

[wherein n=2 or n=3, having substantially the same DSC curve as set out in FIG. 4] *according to claim 6 containing greater than 97.5% of cephalotaxine, 4-methyl (2'R)-2-hydroxy-2-(4-hydroxy-4-methylpentyl) butanedioate (ester) by analytical HPLC assay.*

[8. A purified crystalline compound of the formula:

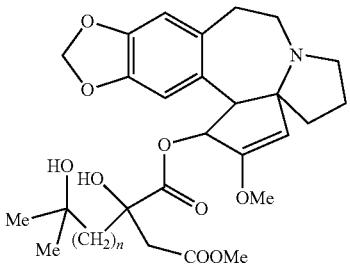

wherein n=2 or n=3, having substantially the same IR spectrum, in KBr, as set out in FIG. 5.]

[9. A purified crystalline compound of the formula:

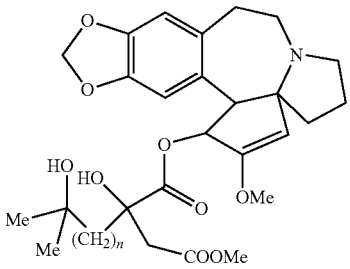

wherein n=2 or n=3, having substantially the same DSC curve as set out in FIG. 4, and substantially the same IR spectrum, in KBr, as set out in FIG. 5.]

[10. The purified compound of claim 1, wherein said purified compound is present in tautomeric forms and salts thereof.]

[11. The purified compound of claim 1, wherein said purified compound is an enantiomer and the total content of impurities includes the other enantiomeric forms.]

12. A pharmaceutical composition comprising [an effective amount of one or more purified compounds according to claim 1, together with] *cephalotaxine, 4-methyl (2'R)-2-hydroxy-2-(4-hydroxy-4-methylpentyl) butanedioate (ester)*:

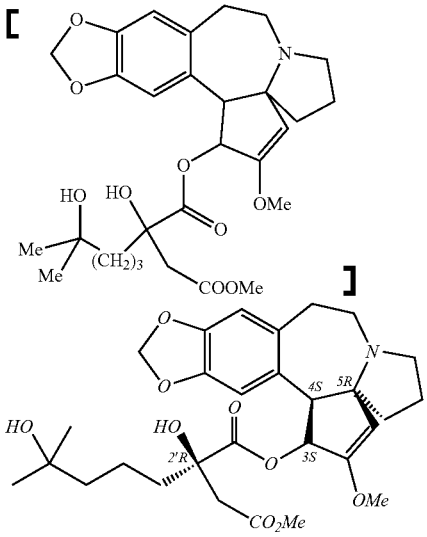

*having a total content of impurities of lower than 1% and having a total content of impurities wherein the major impurity is lower than 0.9% and containing greater than 97.5% of cephalotaxine, 4-methyl (2'R)-2-hydroxy-2-(4-hydroxy-4-methylpentyl) butanedioate (ester) by analytical HPLC assay and/or a pharmaceutically acceptable salt thereof,* [together with] *and at least* one [or more] pharmaceutically acceptable inactive component *chosen from carriers, excipients, adjuvants, and diluents.*

[13. The pharmaceutical composition of claim 12, wherein said pharmaceutically acceptable inactive component is selected from the group consisting of carriers, excipients, adjuvants and diluents.]

[14. A pharmaceutical composition comprising an effective amount of one or more purified compounds according to claim 2, together with one or more pharmaceutically acceptable inactive components.]

[15. A pharmaceutical composition comprising an effective amount of one or more purified compounds according to claim 3, together with one or more pharmaceutically acceptable inactive components.]

[16. A pharmaceutical composition comprising an effective amount of one or more purified crystalline compounds according to claim 5, together with one or more pharmaceutically acceptable inactive components.]

[17. A pharmaceutical composition comprising an effective amount of one or more purified crystalline compounds according to claim 6, together with one or more pharmaceutically acceptable inactive components.]

[18. A pharmaceutical composition comprising an effective amount of one or more purified crystalline compounds according to claim 9, together with one or more pharmaceutically acceptable inactive components.]

[19. A method for treatment of a mammalian parasitic disease comprising administering to a patient in need of such treatment an effective amount of a purified compound as defined in claim 1 for treatment of said parasitic disease.]

[20. A method for immunosuppressive therapy comprising administering to a patient in need of such therapy an effective amount of a purified compound as defined in claim 1 for said immunosuppressive therapy.]

21. A method for *the* treatment of leukemia comprising administering to a patient in *recognized* need of such therapy [an effective amount of a purified compound as defined in claim 1 for treatment of said leukemia] *cephalotaxine, 4-methyl (2'R)-2-hydroxy-2-(4-hydroxy-4-methylpentyl) butanedioate (ester):*

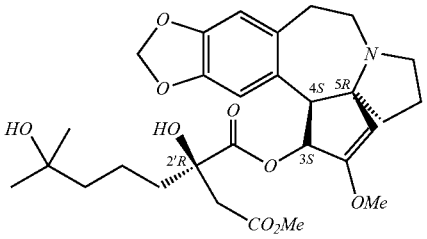

*having a total content of impurities of lower than 1% and having a total content of impurities wherein the major impurity is lower than 0.9% and containing greater than 97.5% of cephalotaxine, 4-methyl (2'R)-2-hydroxy-2-(4-hydroxy-4-methylpentyl) butanedioate (ester) by analytical HPLC assay, and/or a pharmaceutically acceptable salt thereof.*

22. [The] *A* method [according to claim 21, wherein said leukemia is selected from the group consisting of] *for the treatment of* acute myeloid leukemia (AML), myelodysplastic syndrome (MDS) [and], *and/or* myeloproliferative disorders *comprising administering to a patient in recognized need of such treatment cephalotaxine, 4-methyl (2'R)-2-hydroxy-2-(4-hydroxy-4-methylpentyl) butanedioate (ester):*

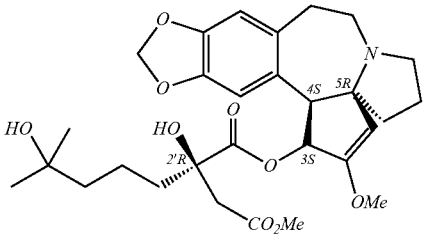

*having a total content of impurities of lower than 1% and having a total content of impurities wherein the major impurity is lower than 0.9% and containing greater than 97.5% of cephalotaxine, 4-methyl (2'R)-2-hydroxy-2-(4-hydroxy-4-methylpentyl) butanedioate (ester) by analytical HPLC assay, and/or a pharmaceutically acceptable salt thereof.*

23. [The] *A* method [according to claim 22, wherein said myeloproliferative disorder is] *for the treatment of* chronic myelogenous leukemia *comprising administering to a patient in recognized need of such treatment cephalotaxine, 4-methyl (2'R)-2-hydroxy-2-(4-hydroxy-4-methylpentyl) butanedioate (ester):*

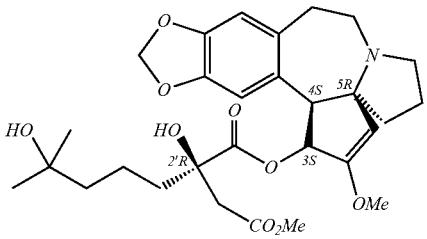

*having a total content of impurities of lower than 1% and having a total content of impurities wherein the major impurity is lower than 0.9% and containing greater than 97.5% of cephalotaxine, 4-methyl (2'R)-2-hydroxy-2-(4-hydroxy-4-methylpentyl) butanedioate (ester) by analytical HPLC assay, and/or a pharmaceutically acceptable salt thereof.*

[24. The method according to claim 21, wherein said purified compound is administered as an adjuvent therapy of resistance to other chemotherapeutic agents.]

25. The method according to claim [21] *23*, wherein said [purified compound] *cephalotaxine, 4-methyl (2'R)-2-hydroxy-2-(4-hydroxy-4-methylpentyl) butanedioate (ester), and/or pharmaceutically acceptable salt thereof,* is administered by a parenteral mode of administration.

[26. The method according to claim 21, wherein said purified compound is administered by an oral mode of administration.]

[27. The method according to claim 21, wherein said purified compound is administered by an anal administration.]

[28. The method according to claim 21, wherein said purified compound is administered by a topical mode of administration.]

29. The method according to claim 26, wherein said parenteral mode of administration is subcutaneous.

*30. The cephalotaxine, 4-methyl (2'R)-2-hydroxy-2-(4-hydroxy-4-methylpentyl) butanedioate (ester):*

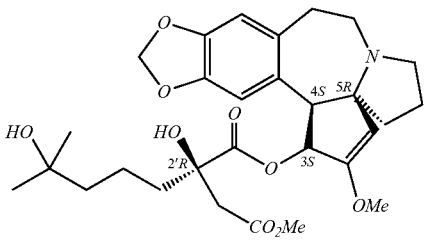

*and/or salt thereof according to claim 1 wherein said cephalotaxine, 4-methyl (2'R)-2-hydroxy-2-(4-hydroxy-4-methylpentyl) butanedioate (ester) and/or salt thereof is semi-synthetic or synthetic.*

*31. A pharmaceutical composition comprising semi-synthetic and/or synthetic cephalotaxine, 4-methyl (2'R)-2-hydroxy-2-(4-hydroxy-4-methylpentyl) butanedioate (ester):*

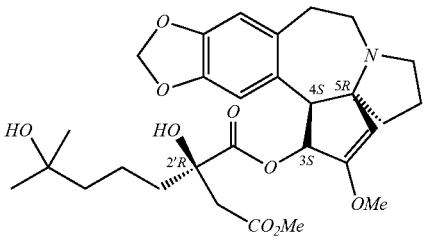

*having a total content of impurities wherein the major impurity is lower than 0.9%, and/or a pharmaceutically acceptable salt thereof, and at least one pharmaceutically acceptable inactive component selected from carriers, excipients, adjuvants, and diluents.*

*32. The cephalotaxine, 4-methyl (2'R)-2-hydroxy-2-(4-hydroxy-4-methylpentyl) butanedioate (ester) according to claim 5 wherein said cephalotaxine, 4-methyl (2'R)-2-hydroxy-2-(4-hydroxy-4-methylpentyl) butanedioate (ester) is semi-synthetic.*

*33. A salt of cephalotaxine, 4-methyl (2'R)-2-hydroxy-2-(4-hydroxy-4-methylpentyl) butanedioate (ester):*

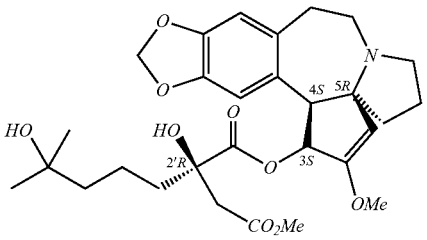

*comprising cephalotaxine, 4-methyl (2'R)-2-hydroxy-2-(4-hydroxy-4-methylpentyl) butanedioate (ester) having a total content of impurities of lower than 1% and/or having a total content of impurities wherein the major impurity is lower than 0.9%.*

*34. A pharmaceutical composition comprising semi-synthetic and/or synthetic cephalotaxine, 4-methyl (2'R)-2-hydroxy-2-(4-hydroxy-4-methylpentyl) butanedioate (ester):*

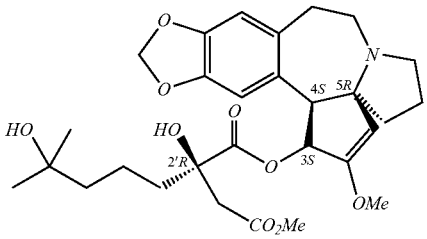

*having a total content of impurities of lower than about 1%, and/or a pharmaceutically acceptable salt thereof, and at least one pharmaceutically acceptable inactive component selected from carriers, excipients, adjuvants, and diluents.*

*35. A pharmaceutical composition comprising cephalotaxine, 4-methyl (2'R)-2-hydroxy-2-(4-hydroxy-4-methylpentyl) butanedioate (ester):*

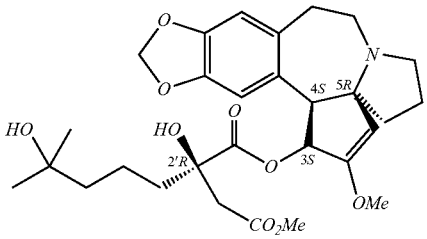

*having a total content of impurities of lower than 1% and having a total content of impurities wherein the major impurity is lower than 0.9%, and/or a pharmaceutically acceptable salt thereof, and at least one pharmaceutically acceptable inactive component selected from carriers, excipients, adjuvants, and diluents.*

* * * * *

UNITED STATES PATENT AND TRADEMARK OFFICE

CERTIFICATE OF CORRECTION

PATENT NO. : RE45,128 E
APPLICATION NO. : 13/661677
DATED : September 9, 2014
INVENTOR(S) : Jean-Pierre Robin et al.

It is certified that error appears in the above-identified patent and that said Letters Patent is hereby corrected as shown below:

In the Claims

Column 106, line 41, claim 29, change "claim 26" to --claim 25--.

Signed and Sealed this
Twenty-third Day of December, 2014

Michelle K. Lee

Michelle K. Lee
*Deputy Director of the United States Patent and Trademark Office*